United States Patent [19]
Fourtillan et al.

[11] Patent Number: 6,048,868
[45] Date of Patent: Apr. 11, 2000

[54] MELATONIN-ANTAGONIST β-CARBOLINE DERIVATIVES AND ANALOGUES THEREOF CONTAINING NAPHTHALENIC STRUCTURE, PROCESS FOR THEIR PREPARATION AND THEIR USE AS MEDICINAL PRODUCTS

[75] Inventors: J-Bernard Fourtillan; Marianne Fourtillan, both of Migne-Auxances; Jean-Claude Jacquesy, Bruxerolles; Marie-Paule Jouannetaud, Poitiers; Bruno Violeau, Marcay; Omar Karam, Poitiers, all of France

[73] Assignees: Cemaf, Migne-Auxances; Laboratories Besins Iscovesco, Paris, both of France

[21] Appl. No.: 09/042,990

[22] Filed: Mar. 17, 1998

Related U.S. Application Data

[63] Continuation-in-part of application No. 08/809,112, filed as application No. PCT/FR95/01179, Sep. 14, 1995, abandoned.

[30] Foreign Application Priority Data

Sep. 14, 1994 [FR] France ................................. 94 10964

[51] Int. Cl.$^7$ ........................ A61K 31/435; C07D 471/04
[52] U.S. Cl. ............................................. 514/285; 546/70
[58] Field of Search ............................... 514/285; 546/70

[56] References Cited

U.S. PATENT DOCUMENTS

| | | | |
|---|---|---|---|
| 3,718,657 | 2/1973 | Garmaise et al. | 546/85 |
| 4,336,260 | 6/1982 | Payne et al. | 514/292 |
| 5,093,352 | 3/1992 | Dubovich | 514/219 |
| 5,206,377 | 4/1993 | McAfee | 548/253 |
| 5,283,343 | 2/1994 | Dubovich et al. | 548/496 |

FOREIGN PATENT DOCUMENTS

| | | |
|---|---|---|
| 0 017 727 | 10/1980 | European Pat. Off. . |
| 0 466 548 | 1/1992 | European Pat. Off. . |
| 1825 | 12/1963 | France . |
| 3395 | 12/1965 | France . |
| 1453532 | 9/1966 | France . |
| 1524953 | 5/1968 | France . |
| 2 455 044 | 11/1980 | France . |
| 3621413 | 1/1988 | Germany . |
| 4104257 | 8/1992 | Germany . |
| 9608490 | 3/1996 | WIPO ................................... 514/285 |

OTHER PUBLICATIONS

Danieli, B. et al.: A one–pot synthesis of 2,6,7,12–tetrahydroindolo[2,3–alpha]–quinolizin–4 (3H)–ones. Synthesis, pp. 353–356, 1984.

Danieli, B. et al.: Efficient synthesis of 1–ethyl–2,3,4,6,7, 12–hexahydroindolo[2,3–alpha]quinolizine. J.C.S. Chem. Comm., p. 109, 1980.

Wasserman, H. et al.: Oxidation of Ylide precursors to vicinal tricarbonyls. Tetrahedron, vol. 48, pp. 7071–7082, 1992.

Siddiqui, S., et al., "Some new derivatives of harmaline and their antibacterial activity," *Fitoterapia*, LXI, No. 5, pp. 425–433 (1990).

Laronze, J., et al., "Nouveaux aspects de la synthése de la nauclèfine," *Bull. Soc. Chim. Fr.* 129:303–307 (1992).

Grigg, R., et al., "The Synthesis of Fused Ring Nitrogen Heterocycles Via Regiospecific Intramolecular Heck Reactions," *Tetrahedron* 46(11):4003–4018 (1990).

Bobowski, G., "2,3,4,9–Tetrahydro–1H–pyrido[3,4–b]indoles. II[1]. Reversible Transformation of 1–Alkyl–2–(4, 9–dihydro–3H–pyrido[3,4–b]indol–1–yl)cyclohexanol into 1–Alkylidene–2,3,4,9–tetrahydro–1H–pyrido[3,4–b]indoles," *J. Heterocyclic Chem.* 24:473–79 (1987).

Finch, N., et al., "Synthesis of 1,3,4,5,6,7,8, 8a–Octahydro–2–methyl–4a–phenylisoquinolin–6–ols. Novel Fragments of the Morphine Molecule," *J. Org. Chem.* 39(8):1118–1124 (1974).

Weller, D., et al., "Synthesis of cis– and–trans–4a–Phenyldecahdydroisoquinolines," *J. Am. Chem. Soc.* 98–21:6650–6657 (Oct. 13, 1976).

Benito, Y., et al., "Synthesis of 1'–Methylspiro[3H–indole–3,n'–piperidines] from 1–Methyl–n–piperidinecarbaldehydes," *J. Heterocyclic Chem.* 24:623–628 (1987).

Meyers, A. I., et al., "An Asymmetric Synthesis and Absolute Configuration of (S)–(–)–Deplancheine," *J. Org. Chem.* 51:3108–3112 (1986).

Yamada, S., et al., "A New Entry into Cinchona Alkaloids via a Biomimetic Pathway," *Tetrahedron Letters* 19:1605–1608 (1976).

Gomez–Pardo, D., et al., "New Approaches to Corynanthe Alkaloids Involving the Conjugate Addition of Dialkyl Malonates to Unsaturated Thiolactams: Synthesis of (±)–3–epi–Dihydrocorynantheol," *Tetrahedron Letters* 33(44):6633–6636 (1992).

Mandal, S.B., et al., "Reduction of Lactams and Thiolactams by Sodium Borohydride: Application in the Synthesis of Some Alkaloids," *J. Org. Chem.* 53:4236–4241 (1988).

Meyer, H., "Pyrrole durch cyclisierende Michael–Addition von Enaminen," *Liebigs Ann. Chem.,* pp. 1534–1544 (1981).

Sainsbury, M., et al., "Synthesis of the Indolo[2',3':3,4] pyrido[1,2–b][2,7]naphthyridinone Alkaloid Nauclefine and its Ring–E Isomers," *J. Chem. Soc., Perkin Trans.* I, pp. 2416–2418 (1976).

(List continued on next page.)

*Primary Examiner*—John Kight
*Assistant Examiner*—Charanjit S. Aulakh
*Attorney, Agent, or Firm*—Finnegan, Henderson, Farabow, Garrett & Dunner, L.L.P.

[57] ABSTRACT

The present invention provides β-carboline derivatives useful as components of cosmetic, medicinal, and pharmaceutical compositions. The medicinal and pharmaceutical compositions can be used to induce hypnotic activity in a subject. Methods of producing the β-carboline derivatives are provided as well.

26 Claims, No Drawings

OTHER PUBLICATIONS

Naito, T., et al., "A Novel Total Synthesis of (±)Ajmalicine," *Heterocycles* 24(8):2117–2120 (1986).

Brandi, A., et al., "Rearrangement of Isoxazoline–5–spiro Derivatives. 2. Synthesis and Rearrangement of Tetrahydroisoxazole–5–spirocyclopropanes. Preparation of Precursors of Quinolizine, Isoquinoline, and Indole Alkaloids," *J. Org. Chem.* 53:2430–2434 (1988).

Blaskó, G., "Pyrimido [1,6–a]pyrido[3,4–b]indoles as new platelet inhibiting agents," *Eur. J. Med. Chem.–Chim. Ther.* 21(2):91–95 (1986).

Atta–ur–Rahman, et al., "Synthesis of Gambirtannine Derivatives by Photocyclization of Enamine Intermediates," *J. Chem. Soc., Perkin Trans.* 1, pp. 59–62 (1982).

Torisawa, Y., et al., "A Total Synthesis of Manzamine C and Its Geometrical Isomer," *Tetrahedron* 47(38):8067–8078 (1991).

Grigg, R., et al., "Palladuim(II) Catalysed Construction of Tetrasubstituted Carbon Centres, and Spiro–and Bridged–ring Compounds from Enamides of 2–Iodobenzoic Acids," *J. Chem. Soc., Chem. Commun.,* 86(23):1697–1699 (1986) [missing pp. 1698–1699].

Atta–ur–Rahman, "Reactions of Harmaline (4,9–Dihydro–7–methoxy–1–methyl–3H–pyrido–[3,4,–b] indole) and its Derivatives. Part II. Reinvestigation of Acetyl–harmaline," *J. Chem. Soc. Perkin Trans I,* pp. 736–738 (1972).

Yamada, F., et al., "Structural Determination of a Natural Alkaloid, 5–Methoxy–1–Oxo–1,2,3, 4–Tetrahydro–β–Carboline and the Synthesis of the Corresponding 8–Methoxy Compound," *Heterocycles* 24(9):2619–2627 (1986).

Naito, T., et al., "First Total Synthesis of (±)–Hirsuteine," *Heterocycles* 26(7):1739–1742 (1987).

Abou–Gharbia, M., et al., "Psychotropic Agents: Synthesis and Antipsychotic Activity of Substituted β–Carbolines," *J. Med. Chem.* 30:1100–1105 (1987).

Nelson, N.A., et al., "Steroidal Hormone Analogs. IX. Bisdehydrodoisynolic Acid Analogs Possessing the 1,2,3, 4–Tetrahydrobenz[f]isoquinoline Nucleus," *J. Org. Chem.* 26:3086–3090 (1961).

Siddiqui, S., et al., "Reaction of Harmidine/Harmaline with BrCN—a Facile Mono—and Di–Bromination at α–Carbon of the Imine Tautomer," *Zeit. Natur., Teil B: Anorg. Chem., Org. Chem.* 40B:1747–1748 (1985).

Glushkov, R.G., *Chem. Abstr.* 72(21):390, No. 111322n (1970).

Bailey, A., *Chem Abstr.* 93(25):841, No. 239278d (1980).

Tokmakov, G.P., et al., *Chem. Abstr.* 111(13):653, No. 115071b (1989).

Fernandez, M., *Chem. Abstr.* 109(9):721, No. 73711m (1988).

Kessar, S.V., et al., *Chem. Abstr.* 81(17):561, No. 105786m (1974).

Kessar, S.V., et al., *Chem. Abstr.* 98(21):695, No. 179750t (1983).

Kametani, T. et al., *Chemical Abstract,* Abstract No. 98:89717, a chemical with registry number 84576–15–8 (1983).

Hamaguchi, F. et al., *Chemical Abstract,* Abstract No. 91:193208, a chemical with registry number 69954–55–8 (1979).

Sanisbury, M. et al., *Chemical Abstract,* Abstract No. 88:62504 (1978).

Bobowski, G., *Chemical Abstract,* Abstract No. 108:55913 (1988).

*Derwent World Patent Index,* No. 92–285369 (1992).

Yamada, F. et al., *Chemical Abstract,* Abstract No. 107:59308, chemicals with registry numbers 109021–57–0 and 109021–62–7 (1987).

MELATONIN-ANTAGONIST β-CARBOLINE DERIVATIVES AND ANALOGUES THEREOF CONTAINING NAPHTHALENIC STRUCTURE, PROCESS FOR THEIR PREPARATION AND THEIR USE AS MEDICINAL PRODUCTS

This application relies on, and is a Continuation-In-Part application of, U.S. application Ser. No. 08/809,112, filed May 8, 1997, now abandoned, filed as PCT/FR95/001179, Sep. 14, 1995, the disclosure of which is hereby incorporated in its entirety.

The present invention relates to novel β-carboline derivatives, which are melatonin agonists, and to analogues of naphthalenic structure, to a process for their preparation and to their use as medicinal products.

Melatonin, N-acetyl-5-methoxytryptamine, is a hormone from the pineal gland, isolated by Lerner & al. (J. Am. Chem. Soc., 80, 1958, 2587), which has formed the subject of numerous studies for its circadian activity, in the rhythm of sleep, for its effects on the production of testosterone, for its activity on the hypothalamus and in psychiatric disorders.

It has thus been envisaged to employ melatonin and analogues thereof especially for the treatment of depression and psychiatric disorders, in particular stress, anxiety, depression, insomnia, schizophrenia, psychoses and epilepsy, and also for the treatment of sleeping disorders associated with travelling ("jet lag"), neurodegenerative diseases of the central nervous system such as Parkinson's disease or Alzheimer's disease, for the treatment of cancers or, alternatively, as a contraceptive or as an analgesic.

However, the direct use of melatonin in vivo has not proved to be very satisfactory, on account of the fact that the first passage through the liver extracts more than 90% of the active principle.

Various melatonin analogues have been described, demonstrating two research routes which relate either to melatonin substituents (WO-A-89/01472, U.S. Pat. No. 5,283,343, U.S. Pat. No. 5,093,352 and WO-A-93/11761) or to the aromatic ring by replacing the indolyl group by a naphthyl group (FR-A-2 658 818, FR-A-2 689 124).

The present patent application proposes a novel route for the development of melatonin analogues having improved activity.

The present invention thus relates to novel carboline derivatives of general formula I

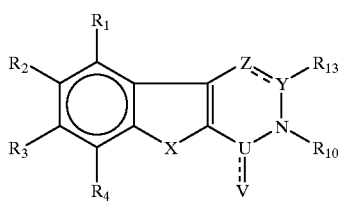

in which
—X— represents a divalent radical of formula
>N—R, or —R$_6$C=CR$_7$—
>U----V represents a divalent radical of formula

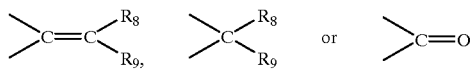

—Z----Y represents a saturated or unsaturated alkylene radical containing 1, 2 or 3 carbons, $R_1$, $R_2$, $R_3$ and $R_4$ represent, independently of each other, a hydrogen atom, a hydroxyl radical, a lower alkyl, cycloalkyl, lower alkoxy, aryloxy, lower aralkoxy, halo or nitro radical or an unsaturated aliphatic chain, formyl, (lower) alkylcarbonyl, (lower)alkyl-carbonyloxy, halo (lower)alkylcarbonyl, halo(lower) alkyl-carbonyloxy, (lower) halogenoalkyl, (lower) halogenoalkyloxy, (lower) alkyloxycarbonyl, carboxyl, optionally substituted carboxamide, two adjacent radicals $R_1$, $R_2$, $R_3$ or $R_4$ being able to form together a 2,3-dihydro-pyranyl group which is possibly bearing an oxo group, $R_5$ represents a hydrogen atom, a lower alkyl cycloalkyl, aryl, lower aralkyl, lower alkoxy, (lower)alkylcarbonyl, halo (lower)alkylcarbonyl, lower alkyloxycarbonyl, amino, alkylamino, dialkylamino, alkylarylamino, diarylamino, (lower) halogenoalkylsulfonyl, alkylsulphonyl or arylsulphonyl radical, $R_6$, $R_7$, $R_8$ and $R_9$ represent, independently of each other, a hydrogen atom, a hydroxyl, a lower alkyl, (lower) halogenoalkyl, a lower hydroxyalkyl, cycloalkyl, aryl or lower aralkyl radical, or an unsaturated aliphatic chain, each optionally substituted with one or more halogens, an amino, (lower) alkylamino, (lower) dialkylamino, arylamino, diarylamino, aralkylamino, arylalkylamino, (lower) halogenoalkyloxy arylcarbonyl, alkylcarbonyl, alkoxycarbonyl, lower alkoxy, (lower)aralkyl-carbonyl, alkoxyalkyl, formyl, (lower)alkyl-carbonyl, (lower)alkylcarbonyloxy, halo (lower)alkyl-carbonyl, halo(lower)alkyl-carbonyloxy, (lower)alkyloxycarbonyl, carboxyl, halo, optionally substituted carbonamide, alkylsulphonyl or an arylsulphonyl radical, (lower) halogenoalkylsulfonyl.

$R_6$ and $R_7$, $R_5$ and $R_6$, and $R_8$ and $R_9$ may be joined to form a ring, $R_{10}$ represents a hydrogen atom, a lower alkyl radical, an aryl radical, an alkylsulphonyl, arylsulphonyl or a haloalkylsulfonyl, an unsaturated aliphatic chain, an aralkyl radical or a radical of formula

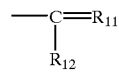

$R_{11}$ represents an oxygen atom, a sulphur atom or a radical N—$R_{14}$, $R_{12}$ represents, a hydrogen atom, a lower alkyl, (lower) halogenoalkyl, a lower hydroxyalkyl, cycloalkyl, aryl or lower aralkyl radical, or an unsaturated aliphatic chain, each optionally substituted with one or more halogens, an amino, (lower)alkylamino, (lower)dialkylamino, arylamino, diarylamino, aralkylamino, arylalkylamino, arylcarbonyl, alkylcarbonyl, alkoxycarbonyl, lower alkoxy, (lower) halogenoalkyloxy, (lower)aralkyl-carbonyl, alkoxyalkyl, formyl, (lower)alkyl-carbonyl, (lower) alkylcarbonyloxy, halo (lower) alkyl-carbonyl, halo(lower)alkylcarbonyloxy, (lower)alkyloxycarbonyl, carboxyl, halo, optionally substituted carbonamide, alkylsulphonyl or an arylsulphonyl radical, $R_{13}$ represents a hydrogen atom, a lower alkyl, cycloalkyl, carboxyl, (lower)alkyloxycarbonyl or optionally substituted carbonamide radical, or an unsaturated aliphatic chain, $R_{14}$ represents a hydrogen atom, a lower alkyl radical, an unsaturated aliphatic chain, lower aralkyl or aryl, it being possible for $R_1$–$R_2$, $R_2$–$R_3$ and $R_3$–$R_4$ to form part of another aromatic or non-aromatic ring with or without a hetero atom and optionally bearing a carbonyl or thiocarbonyl group, it being possible for $R_9$ and $R_{12}$ to be joined to form a saturated or unsaturated ring containing at least 5 atoms and preferably 6, it being possible for this ring to contain several hetero atoms, one or more carbonyl or thiocarbonyl radicals, and to be substituted with one or more groups which may be, independently of each other, a hydroxyl radical, lower hydroxyalkyl, cycloalkyl, (lower) halogenoalkyl, formyl, (lower) alkylcarbonyl, (lower) alkylcarbonyloxy, (lower) alkyloxycarbonyl, (lower) halogenoalkylcarbonyl, (lower) halogenoalkylcarbonyloxy, (lower) halogenoalkyoxycarbonyl, carboxyl, or a optionally substituted carbonamide group, alkylsulfonyl, arylsulfonyl, halogeroalkylsulfonyl, a lower alkyl, lower alkoxy, aryloxy, lower aralkoxy, halo, nitro amino, lower alkylamino, (lower) dialkylamino radical or an unsaturated aliphatic chain, the racemic mixtures thereof, the pure enantiomers therof or the mixtures thereof in all proportions, and the therapeutically acceptable salts thereof.

The expressions lower alkyl, lower alkoxy or perhalo (lower)alkyl are generally understood to refer to radicals whose alkyl residue comprises between 1 and 6 carbon atoms.

These are preferably linear or branched $C_1$–$C_4$ alkyl residues chosen more particularly from methyl, ethyl, n-propyl, i-propyl, n-butyl and t-butyl groups.

The expression unsaturated aliphatic chain is preferably understood to refer to an unsaturated $C_2$–$C_6$ hydrocarbon chain.

The term aryl generally denotes aromatic and heteroaromatic groups, in particular aryls chosen from phenyl, thienyl, furanyl, pyridyl and naphthyl groups.

The aryl radicals may also be substituted with one or more substituents chosen in particular from the lower alkyl, (lower) halogenoalkyl, hydroxyl, aryloxy, aralkoxy, nitro, amino, alkylamino, dialkylamino, formyl, (lower) alkylcarbonyl, (lower)alkylcarbonyloxy, (lower) alkyloxycarbonyl, (lower)halogenoalkylcarbonyl, (lower) halogenoalkylcarbonyloxy, (lower) halogenoalkyloxycarbonyl, carboxyl, lower alkoxy or halo radicals defined above.

The expressions lower aralkyl will be understood to refer to the combination of a lower alkyl and an aryl as defined above. This will preferably be the benzyl radical, which is optionally substituted.

The halo radicals are preferably chosen from fluorine, chlorine, bromine and iodine atoms.

The perhalo radicals are preferably perfluoro radicals.

When $R_1$–$R_2$, $R_2$–$R_3$, and $R_3$–$R_4$ form part of another aromatic ring, with or without a hetero atom, this is preferably another benzene ring, which is optionally substituted, or a pyridyl ring, which is optionally substituted.

When $R_1$, $R_2$, $R_2$–$R_3$, and $R_3$–$R_4$ form part of another non-aromatic ring, they preferably form together a divalent radical of formula —O—$(CH_2)_m$—, m being equal to 2 or 3, which is optionally substituted, or a divalent radical of formula —O—$(CH_2)_p$—O—, p being equal to 1 or 2, which is optionally substituted.

When the derivatives comprise at least 1 asymmetric carbon, the present invention relates to the corresponding racemic mixtures, as well as to the pure enantiomers thereof or the mixtures thereof in all proportions.

The therapeutically acceptable salts of the derivatives according to the invention are the usual organic or inorganic salts of the art, in particular the hydrochlorides, the tosylates, the mesylates and the citrates, as well as solvates such as the hydrates or hemihydrates of the compounds of general formula I.

The present invention relates more particularly to the derivatives of general formula I for which $R_{10}$ preferably represents a radical of formula

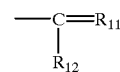

and $R_{11}$, represents an oxygen atom or a sulfur atom, or $R_{10}$ represents an alkylsulfonyl, halogenoalkylsulfonyl, arylsulfonyl.

Advantageously, at least one of the substituents $R_2$ or $R_3$ is other than a hydrogen atom and preferably represents a hydroxyl or lower alkoxy radical, in particular methoxy.

$R_1$, $R_4$, $R_6$ and $R_7$ preferably represent a hydrogen atom.

Among the preferred derivatives according to the invention, $R_{13}$ represents a hydrogen atom and $R_{12}$ is advantageously a lower alkyl radical, optionally linked to $R_9$ in order to form a ring, a methyl, an ethyl, an n-porpyl, a cyclopropyl, an aryl, an aralkyl, a perfluoromethyl, perfluoromethyl or perfluoropropyl radical or an arylamino radical.

More particularly, the present invention is concerned with carboline derivatives of general formula Iα.

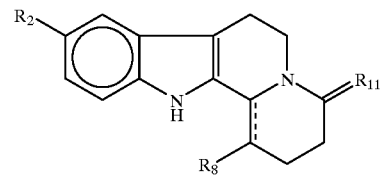

in which $R_2$ represents a lower alkoxy radical, $R_{11}$ represents an oxygen or a sulphur atom, $R_8$ as defined above.

The present invention also relates to the process for the preparation of the derivatives of general formula I as defined above.

In the particular case where $R_{11}$ represents an oxygen atom,

—Z----Y— represents a radical of the form —$(CH_2)_n$—CH< with n equal to 1 or 2, $R_9$ and $R_{12}$ do not form a ring and where $R_8$ and $R_9$ do not represent a (lower) alkyloxycarbonyl radical, the derivatives of formula I may be obtained directly by reacting the compounds of general formula IIa or IIb,

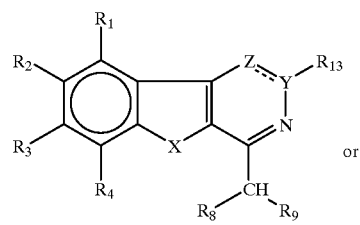

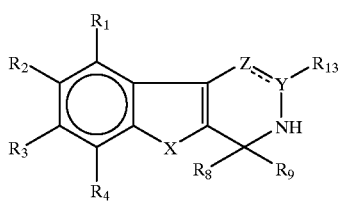

IIb for which $R_1$, $R_2$, $R_3$, $R_4$, $R_5$, $R_6$, $R_9$, $R_{13}$, X, Y and Z are defined above, with an acylating agent (acid chloride, acid anhydride, chloroformate or isocyanate) or by exchange with an ester in an intramolecular or intermolecular reaction, the derivatives of formula I'a

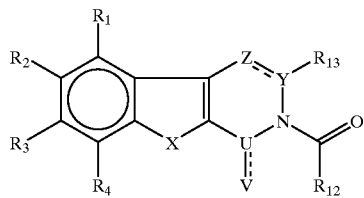

I'a in which $R_1$, $R_2$, $R_3$, $R_4$, $R_5$, $R_{12}$, $R_{13}$, U, V, X, Y and Z are defined above, are thus obtained.

In order to obtain the derivatives of general formula IIa, a Bischler-Napieralski reaction is carried out by reacting the compounds of general formula IIIa

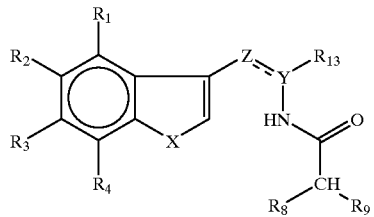

IIIa in which $R_1$, $R_2$, $R_3$, $R_4$, $R_5$, $R_8$, $R_9$, $R_{13}$, X, Y, and Z are defined above, with phosphorus pentoxide ($P_2O_5$) or phosphorus oxychloride ($POCl_3$), in a suitable solvent, for example toluene or xylene. These derivatives may also be prepared by permanganic oxidation of the derivatives of general formula IIb.

In order to obtain the derivatives of general formula IIa, in which X has the formula —$CR_6$=$CR_7$—, the derivatives of general formula IIb are oxidized.

In order to obtain the derivatives of general formula IIb, a Pictet-Spengler reaction is carried out by reacting the derivatives of general formula IIIb

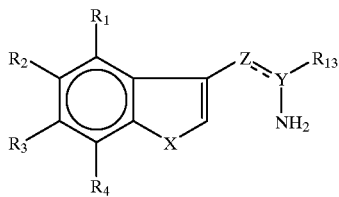

IIIb for which $R_1$, $R_2$, $R_3$, $R_4$, $R_5$, $R_{13}$, X, Y, and Z are defined above; with the compounds of formula $R_8$—CO—$R_9$ or chemical equivalents thereof such a as a ketal, an acetal or an enol ether, an enol ester or a nitrile $R_8CN$ under reducing conditions for which $R_8$ and $R_9$ are defined above.

In the particular case in which the acylating agent is trifluoroacetic anhydride (($CF_3CO)_2O$), the acylation reaction of the compounds of general formula IIa leads, besides I'a to compounds of general formula I'b (Z and E isomers)

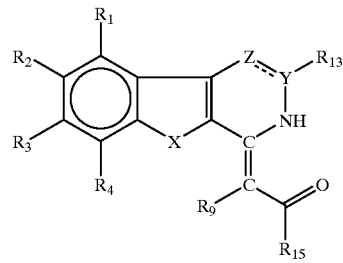

I'b for which $R_1$, $R_2$, $R_3$, $R_4$, $R_9$, $R_{13}$, X, Y, and Z are defined above and $R_{15}$ represents a $CF_3$ group.

In the particular case in which $R_8$ or $R_9$ represents a (lower)alkyloxycarbonyl group, the Bischler-Napieralski reaction leads directly to a compound of formula I'b where $R_{15}$ is a lower alkoxy radical.

The derivatives of general formula I for which $R_9$ and $R_{12}$ are linked in order to form a ring, are obtained by carrying out a Bischler-Napieralski reaction, under the conditions described above, on a cyclic imide of general formula IIIc

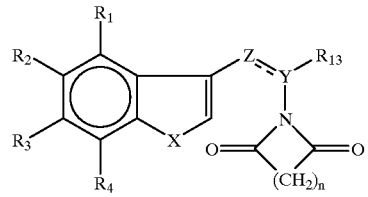

IIIc for which $R_1$, $R_2$, $R_3$, $R_4$, $R_{13}$, X, Y and Z are defined above and n is equal to 2, 3, 4 or 5 or by derivatives of formula IIa with a carboxylic acid (such as acrylic acid) in the presence or not of diphenylphosphorylazide, or with the acrylonitrile or with an acid chloride and the derivative of general formula I'c

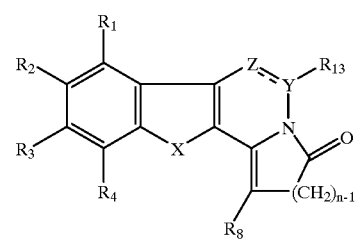

I'c for which $R_1$, $R_2$, $R_3$, $R_4$, $R_8$, $R_{13}$, X, Y, Z and n are defined above, is thus obtained.

The starting materials of formula II, such as the 10-methoxyharmalan, and of formula III, such as the 3nelatonin, tryptamine, 5-methoxytryptamine and 4-methoxy-phenylhydrazine, are commercially available or are described in Chim. Ther., 1966, 57 for the derivatives of the naphthyl series, or may be prepared from these derivatives.

The present invention also relates to the derivatives of formulae IIIa, IIIb and IIIc, as well as to the intermediates of formulae IIa and IIb, which are useful in particular for the preparation of derivatives of general formula I.

The enantiomers of the derivatives of formula I and the mixtures thereof in all proportions may be obtained by the usual methods for the resolution of racemic mixtures, in particular by selective crystallization in the presence of an acid.

The following examples of preparations of derivatives according to the invention make it possible to illustrate the present invention without, however, seeking to limit the scope thereof.

Examples of derivatives of formula I'a for which $R_1$, $R_4$ and $R_{13}$ represent hydrogen atoms, $R_{11}$ represents an oxygen atom,
—Z----Y— represents a radical of the form —$(CH_2)_n$—CH<,
>U----V represents a radical of formula >C=$CH_2$,
—X— represents a divalent radical of formula >N—$R_5$, are reported in Table I below:

TABLE I

| Example | n | $R_2$ | $R_3$ | $R_5$ | $R_{12}$ | Code |
|---|---|---|---|---|---|---|
| 1 | 1 | $OCH_3$ | H | H | $C_2F_5$ | CARBO3 |
| 2 | 1 | $OCH_3$ | H | H | $CF_3$ | CARBO4 |
| 3 | 1 | $OCH_3$ | H | H | H | CARBO16 |
| 4 | 1 | $OCH_3$ | H | H | $CH_3$ | CARBO2 |
| 5 | 1 | $OCH_3$ | H | H | $CH_2CH_3$ | CARBO2A |
| 6 | 1 | $OCH_3$ | H | H | $CH_2CH_2CH_3$ | CARBO2B |
| 7 | 1 | $OCH_3$ | H | H | cyclopropyl | CARBO11 |
| 8 | 1 | $OCH_3$ | H | H | phenyl | CARBO15 |
| 9 | 1 | $OCH_3$ | H | H | $OCH_2CH_3$ | CARBO5 |
| 10 | 1 | $OCH_3$ | H | H | $NH-C_6H_5$ | CARBO8 |
| 11 | 1 | $OCH_3$ | H | $CH_3$ | $CH_3$ | 1MCARBO2 |
| 12 | 1 | $OCH_3$ | $OCH_3$ | H | $CH_3$ | DMCARBO2 |
| 13 | 1 | H | $OCH_3$ | H | $CH_3$ | CARBO1 |
| 14 | 1 | H | H | H | $CH_3$ | CARBOTRYP1 |
| 15 | 2 | $OCH_3$ | H | H | $CH_3$ | HOMOCARBO2 |

Examples of derivatives of formula I'a for which $R_1$, $R_4$ and $R_{13}$ represent hydrogen atoms, $R_{11}$ represents an oxygen atom,
—Z----Y— represents a radical of the form —$CH_2$—CH<,
>U----V represents a radical of formula C=$CH_2$,
—X— represents a divalent radical of formula
—CH=CH— are reported in Table II below:

TABLE II

| Example | $R_2$ | $R_3$ | $R_{12}$ | Code |
|---|---|---|---|---|
| 16 | $OCH_3$ | H | $CH_3$ | NAPH2 |
| 17 | H | $OCH_3$ | $CH_3$ | NAPH3 |

Examples of derivatives of formula I'a for which $R_1$, $R_3$, $R_4$, $R_5$ and $R_{13}$ represent hydrogen atoms, $R_{11}$ represents an oxygen atom,
—Z----Y— represents a radical of the form —$CH_2$—CH<,
>U----V represents a radical of formula

—X— represents a divalent radical of formula >N—$R_5$, are reported in Table III below:

TABLE III

| Example | $R_2$ | $R_8$ | $R_9$ | $R_{12}$ | Code |
|---|---|---|---|---|---|
| 18 | $OCH_3$ | H | $CH_3$ | $CH_3$ | CARBO17 |
| 19 | $OCH_3$ | H | $CH_2OCH_3$ | $CH_3$ | CARBO18 |

Examples of derivatives of formula I'b, for which $R_1$, $R_3$, $R_4$, $R_5$, $R_9$ and $R_{13}$ represent hydrogen atoms, —Z----Y— represents a radical of the form —$CH_2$—CH<, —X— represents a divalent radical of formula >N—$R_5$, are reported in Table IV below:

TABLE IV

| Example | $R_2$ | $R_{15}$ | Code |
|---|---|---|---|
| 20 | $OCH_3$ | $CF_3$ | ENA1 |
| 21 | $OCH_3$ | $OCH_2CH_3$ | ENA2 |

Examples of derivatives of formula I'c, for which $R_1$, $R_3$, $R_4$, $R_5$, and $R_{13}$ represent hydrogen atoms, —Z----Y— represents a radical of the form —$CH_2$—CH<, —X— represents a divalent radical of formula >N—$R_5$, and n is equal to 3, are reported in Table V below:

TABLE V

| Example | $R_2$ | Code |
|---|---|---|
| 22 | $OCH_3$ | CARB07 |
| 23 | H | CARBOTRYP2 |

An example of derivatives of formula I, for which $R_1$, $R_3$, $R_4$, $R_5$ and $R_{13}$, represent hydrogen atoms, $R_{10}$ represents the —$COCH_3$ radical, —Z----Y— represents a radical of the form —$(CH_2)_n$—CH<, >U----V represents a radical of formula >C=O, —X— represents a divalent radical of formula >N—$R_5$, is reported in Table VI below:

TABLE VI

| Example | $R_2$ | Code |
|---|---|---|
| 24 | $OCH_3$ | CARBO6 |

The synthesis of the products of general formulae I, reported in Tables I to V, is presented in detail below.

EXAMPLE 1

1-Methylene-2-pentafluoropropionyl-6-methoxy-1,2,',4-tetrahydro-β-carboline

Formula: $C_{16}H_{13}N_2O_2F_5$ M=360.28 g.mol$^{-1}$

To a solution of 10-methoxyharmalan (150 mg) in pyridine (2 ml) is added PFPA (1.1 eq). After reaction for 5 min., the mixture is hydrolysed and extracted with $CH_2Cl_2$. The crude product is then flash-chromatographed (eluent: pet. ether/EtOAc; 50/50). 1-Methylene-2-pentafluoropropionyl-6-methoxy-1,2,3,4-tetrahydro-β-carboline is recovered (85 mg, yield 35%).

Melting point 148–50° C.

NMR: $^1$H (CD$_3$COCD$_3$): 2.98 (t, 6 Hz, 2H, H-4); 3.80 (s, 3H, OCH$_3$); 4.18 (t, 6 Hz, H-3); 5.39 (broad s, 1H, H vin.); 5.71 (s, 1H, H vin.); 6.83 (dd, 8.8 and 3 Hz, H-8); 7.01 (d, 3 Hz, 1H, H-5); 7.26 (d, 8.8 Hz, 1H, H-7); 8.47 (broad s, 1H, N-H).

$^{13}$C (CDCl$_3$): 22.3 (C-4); 46.4 (t 3 Hz, C-3); 56.0 (OCH$_3$); 101.1 and 103.3 (C vin. and C-5); 112.1 and 114.1 (C-7 and C-8); 112.2 (C-4a); 127.1 and 132.3 (C-5a and C-8a); 129.8 (C-1a); 134.7 (C-1); 154.8 (C-6).

Mass spectrum: m/z: 360 (M$^+$), 241, 213
Exact mass: calculated: 360.0897 found: 360.0888

EXAMPLE 2

1-Methylene-2-trifluoroacetyl-6-methoxy-1,2,3,4-tetra-hydro-β-carboline

Formula: $C_{15}H_{13}N_2F_3$ M=310.28 g.mol$^{-1}$

To a solution of 10-methoxyharmalan (40 mg) in triethylamine (1 ml) is added TFA (2.2 eq). After reaction for 15 min. at 0° C., the mixture is hydrolysed and extracted with $CH_2Cl_2$. The crude product is then chromatographed on a preparative plate (eluent: $CH_2Cl_2$). 1-Methylene-2-trifluoroacetyl-6-methoxy-1,2,3,4-tetra-hydro-β-carboline is recovered (yield: 20%).

Melting point 184° C.

NMR: $^1$H (CD$_3$COCD$_3$): 2.97 (t, 5.1 Hz, 2H, H-4); 3.80 (s, 3H,OCH$_3$); 4.14 (t, 5.1 Hz, H-3); 5.37 (broad s, 1H, H vin.); 5.70 (s, 1H, H vin.); 6.84 (dd, 9.5 and 2.9 Hz, H-8); 7.01 (d, 2.9 Hz, 1H, H-5); 7.26 (d, 9.5 Hz, 1H, H-7); 10.41 (broad s, 1H, N-H).

$^{13}$C (CDCl$_3$): 22.1 (C-4); 46.4 (C-3); 56.0 (OCH$_3$) 101.1 and 103.6 (C vin. and C-5); 112.1 and 114.5 (C-7 and C-8); 112.2 (c-4a); 127.2 and 132.2 (C-5a and C-8a); 129.8 (C-la); 136.4 (C-1); 154.8 (C-6).

Mass spectrum: m/z: 310 (M$^+$), 213, 185
Exact mass: calculated: 310.0929 found: 310.0924

EXAMPLE 3

1-Methylene-2-formyl-6-methoxy-1,2,3,4-tetrahydro-β-carboline

Formula: $C_{14}H_{14}N_2O_2$ M=242.27 g.mol$^{-1}$

To acetic anhydride (1 ml) cooled to 0° C. is added dropwise formic acid (0.5 ml). The mixture is heated for 15 min. at 50° C. After cooling rapidly to 0° C., 10-methoxyharmalan (200 mg) is added slowly and portionwise and the medium is left stirring for 2 h. The crude product is then taken to dryness and, after separation by chromatography (eluent: EtOAc/pet. ether; 50/50), 1-methylene-2-formyl-6-methoxy-1,2,3,4-tetrahydro-β-carboline is obtained.

Melting point 180–1° C.

NMR: $^1$H (CDCl$_3$): 2.89 (t, 2H, H-4); 3.84 (s, 3H, OCH$_3$); 4.06 (t, H-3); 4.84 and 4.89 (2s, 2H, H vin.); 6.91 (d, 1H, H-7); 6.91 (s, 1H, H-5); 7.21 (d, 1H, H-8); 8.27 (broad s, 1H, N-H), 8.7 (s, 1H, H formyl)

Mass spectrum: m/z: 242 (M$^+$), 213 (100), 199, 170.

EXAMPLE 4

1-Methylene-2-acetyl-6-methoxy-1,2,3,4-tetrahydro-β-carboline

Formula: $C_{15}H_{16}N_2O_2$ M=256.30 g.mol$^{-1}$

To a solution of 10-methoxyharmalan (1 mmol) in pyridine (2 ml) is added acetic anhydride (1.1 eq) . After acid hydrolysis and extraction with ethyl acetate, the crude product is flash-chromatographed (eluent: EtOAc/pet. ether; 50/50). The 1-methylene-2-acetyl-6-methoxy-1,2,3,4-tetrahydro-β-carboline elutes off first.

Melting point 196–8° C.

NMR: $^1$H (CDCl$_1$): 2.29 (s, 3H, NCOCH$_3$); 2.85 (t, 6 Hz, 2H, H-4); 3.85 (s, 3H, OCH$_3$); 4.12 (t, 6 Hz, H-3); 4.97 (broad s, 1H, H vin.); 5.35 (s, 1H, H vin.); 6.89 (dd, 8 and 2 Hz, H-7); 6.91 (s, 1H, H-5); 7.22 (d, 8.6 Hz, 1H, H-6); 8.47 (broad s, 1H, N-H).

$^{13}$C (CDCl$_1$): 17.6 and 22.9 (C-4 and CH$_3$ amide); 43.6 (C-3); 56.0 (OCH$_3$); 101.1 and 101.3 (C vin. and C-5); 111.9 and 114.1 (C-7 and C-8); 113.9 (C-4a); 127.3 and 132.3 (C-5a and C-8a); 130.5 (C-1a); 138.1 (C-1); 154.6 (C-6); 170.2 (C=O).

Mass spectrum: m/z: 256 (M$^+$), 213 (M—COCH$_3$), 185, 170.
Exact mass: calculated: 256.1212 found: 256.1208

EXAMPLE 5

1-ethylene-2-propionyl-6-methoxy-1,2,3,4-tetrahydro-β-carboline

Formula: $C_{16}H_{18}N_2O_2$ M=270.33 g.mol$^{-1}$

To a solution of 10-methoxyharmalan in pyridine is added propionic anhydride. After acid hydrolysis and extraction with ethyl acetate, the crude product is then flash-chromatographed (eluent: EtOAc/pet. ether; 50/50). The 1-methylene-2-propionyl-6-methoxy-1,2,3,4-tetrahydro-β-carboline elutes off first.

Melting point: 174–75° C.

NMR: $^1$H (CDCl$_3$): 1.96 (t, 3H, CH$_3$ ethyl); 2.63 (q, 2H, CH$_3$ ethyl); 2.83 (t, 2H, H-4); 3.85 (s, 3H, OCH$_3$); 4.12 (t, 2H, H-3); 5.01 (broad 8, 1H, H vin.); 5.37 (s, 1H, H vin.); 6.88 (dd, H-7); 6.91 (s, 1H, H-5); 7.22 (d, 1H, H-8); 8.53 (broad s, 1H, N-H).

$^{13}$C (CDCl$_3$): 10.1 (CH$_3$ ethyl); 21.7 (C-4); 27.6 (CH$_3$ ethyl); 43.9 (C-3); 56.0 (OCH$_3$); 100.9 and 101.0 (C vin. and C-5); 112.0 and 114.1 (C-7 and C-8); 113.0 (C-4a); 127.0, 130.0 and 132.0 (C-5a, C-8a, C-1a); 137.0 (C-1); 154.5 (C-6); 174.0 (C=O).

Mass spectrum: m/z: 270 (M$^+$), 213 (100), 170.
Exact mass: calculated: 270.1368 found: 270.1364

EXAMPLE 6

1-Methylene-2-butyryl-6-methoxy-1,2,3,4-tetrahydro-β-carboline

Formula: $C_{17}H_{20}N_2O_2$ M=284.35 g.mol$^{-1}$

To a solution of 10-methoxyharinalan (1 mmol) in pyridine (2 ml) is added butyric anhydride (1.1 eq). After acid hydrolysis and extraction with ethyl acetate, the crude product is then flash-chromatographed (eluent: EtOAc/pet. ether; 50/50). The 1-methylene-2-butyryl-6-methoxy-1,2,3,4-tetrahydro-β-carboline elutes off first.

Melting point 188–190° C.

NMR: $^1$H (CDCl$_3$): 0.91 (t, 3H, CH$_3$ propyl); 1.69 (m, 2H, CH$_2$ ethyl); 2.58 (m, 2H, CH$_2$—CO); 2.83 (t, 2H, H-4); 3.85 (s, 3H, OCH$_3$); 4.13 (t, 2H, H-3); 5.01 (broad s, 1H, H vin. ); 5.35 (s, 1H, H vin.); 6.88 (dd, H-7); 6.91 (s, 1H, H-5); 7.23 (d, 1H, H-8); 8.46 (broad s, 1H, N-H).

$^{13}$C (CDCl$_3$): 13.8 (CH$_3$ propyl); 19.3 (CH$_2$CH$_3$); 21.8 (C-4); 36.2 (CH$_2$CON); 43.9 (C-3); 55.9 (OCH$_3$); 101 and 101.6 (C vin. and C-5); 112 and 114 (C-7 and C-8); 113.5 (C-4a); 127.3, 130.7 and 132.2 (C-5a, C-8a, C-1a); 137.8 (C-1); 154.5 (C-6); 173.2 (C=O)

Mass spectrum: m/z: 284 (M$^+$), 270, 213 (100), 170.
Exact mass: calculated: 284.1525 found: 284.1522

EXAMPLE 7

1-Methylene-2-cyclopropylcarbonyl-6-methoxy-1,2,3,4-tetrahydro-β-carboline

Formula: $C_{17}H_{18}N_2O_2$ M=282.34 g.mol$^-$

To a solution of 10-methoxyharmalan in anhydrous dichloromethane is added cyclopropylcarbonyl chloride. The solution becomes clear and is left to stir for 1 h at 0° C. After evaporation of the dichloromethane, the 1-methylene-2-cyclopropylcarbonyl-6-methoxy-1,2,3,4-tetrahydro-β-carboline is recovered by chromatography on silica (pet. ether/EtOAc; 50/50). (The product turns yellow in the light).

Melting point 162–3° C.

NMR: $^1$H (CDCl$_3$): 0.78 and 1.10 (2 m, 2Y. and 2H, 2 x methylene of the cyclopropane), 2.27 (m, 1H, CH of the cyclopropane); 2.85 (t, 2H, H-4); 3.86 (s, 3H, OCH$_3$); 4.16

(t, H-3); 5.16 (broad s, 1H, H vin.) ; 5.30 (s, 1H, H vin.); 6.86 (dd, H-7); 6.92 (d, 1H, H-5);. 7.24 (d, 1H, H-8); 8.09 (broad s, 1H, N-H).

$^{13}$C (CDCl$_3$) 8.9, 13.3 and 14.1. (cyclopropyl); 21.7 (C-4); 43.7 (C-3); 55.9 (OCH$_3$); 100.8 and 101.0 (C vin. and C-5); 111.9 and 113.9 (C-7 and C-8); 113.3 (C-4a); 127.3 and 132.4 (C-5a and C-8a); 130.7 (C-1a); 137.8 (C-1); 154.4 (C-6); 173.6 (C=O).

Mass spectrum: m/z: 282 (M$^+$), 267, 213.

Exact mass: calculated: 282.1368 found: 282.1370

EXAMPLE 8

1-Methylene-2-benzoyl-6-methoxy-1,2,3,4-tetrahydro-β-carboline

Formula: C$_{20}$H$_{18}$N$_2$O$_2$ M=318.37 g.mol$^{-1}$

To a solution of 10-methoxyharmalan in pyridine is added benzoic anhydride. After acid hydrolysis and extraction with ethyl acetate, the crude product is then flash-chromatographed (eluent: EtOAc/pet. ether; 50/50). The 1-methylene-2-benzoyl-6-methoxy-1,2,3,4-tetrahydro-β-carboline elutes off first.

Melting point 192–3° C.

NMR: $^1$H (CDCl$_3$): 2.95 (t, 6 Hz, 2H, H-4); 3.86 (s, 3H, OCH$_3$); 4.20 (t 6 Hz, H-3); 4.43 (broad s, liH, HO vin.); 5.06 (s, 1H, H vin.); 6.87 (dd, H-7); 6.95 (d, 1H, H-5); 7.15 (d, 1H, H-8); 7.30–7.45 (m, 5H, aromatic H of COC$_6$H$_5$); 8.33 (broad s, 1H, N-H).

Mass spectrum: m/z: 318 (M.), 289, (100), 213 (M—COC$_6$H$_5$), 170.

Exact mass: calculated: 318.1368 found: 318.1370

EXAMPLE 9

1-Methylene-2-ethoxycarbonyl-6 -methoxy-1,2,3,4-tetrahydro-β-carboline

Formula: C$_{16}$H$_{18}$N$_2$O$_3$ M=286.33 g.mol$^{-1}$

To a solution of 10-methoxyharmalan in dichloromethane is added triethylamine (1.5 eq) and the mixture is cooled to 0° C. A solution (1/5 v/v) of ethyl chloro-formate in dichloromethane is then added dropwise. The mixture is stirred at 0° C. until the starting material disappears (2 h). After evaporation of the solvent, the crude product is separated out on a chromatography plate (eluent: EtOAc/pet. ether; 50/50).

Melting point 130–4° C.

NMR: $^1$H (CDCl$_3$): 1.27 (t, 3H, CH$_3$ of the ethyl); 2.81 (t, 2H, H-4); 3.80 (s, 3H, OCH$_3$); 4.01 (t, 2II, H-3); 4.20 (q, 2H, H-3); 5.34 (s, 1H, H vin.); 5.48 (s, 1H, H vin.); 6.79 (dd, H-7); 6.99 (d, 1H, H-5); 7.22 (d, 1H, H-8); 10.22 (broad s, 1H, N-H).

EXAMPLE 10

1-Methylene-2-(N-phenyl)carbamoyl-6-methoxy-1,2,3,4-tetrahydro-β-carboline

Formula: C$_{20}$H$_{19}$N$_3$O$_2$ M=333.38 g.mol$^{-1}$

To a solution of 10-methoxyharmalan in anhydrous ether is added phenyl isocyanate. The mixture is stirred for 1 h 30 and then heated at 45° C. for 30 min. The 1-methylene-2-(N-plienyl)carbamoyl-6-methoxy-1,2,3,4-tetrahydro-β-carboline is recovered by filtration and then washed with ether.

Melting point 151–4° C.

NMR: $^1$H (DMSO/CDCl$_3$, 2/1): 2.80 (m, 2H, H-6); 3.77 (s, 3H, OCH$_3$); 3.96 (m, H-7); 5.09 and 5.61 (2s, 2H, H-vin.); 6.86 (m, 1H, H-7); 7.29 (d, 1H, H-5); 7.48 (d, 1H, H-8); 8.48 and 11.09 (2 broad 5, 2H, 2N-H).

Mass spectrum: m/z: 213 (M-120 CONHC$_6$H$_5$), 170, 119.

EXAMPLE 11

1-Methylene-2-acetyl-6-methoxy-9-methyl-1,2,3,4-tetrahydro-β-carboline

Formula: C$_{16}$H$_{18}$N$_2$O$_2$ M=270.33 g.mol$^{-1}$

Melatonin (600 mg) is dissolved in DMSO (2 ml) in a 25 ml round-bottomed flask, and potassium hydroxide (6 pellets, ≈300 mg) is then added. After stirring for 15 min., methyl iodide (0.6 ml) is added. The mixture is stirred overnight, diluted with water and then acidified with 2N hydrochloric acid. After extraction (dichloromethane 3 times), washing with acidic water, drying over magnesium sulphate and evaporation of the solvent, N-2-[(5-methoxy-1-methyl)indol-3-yl]ethylacetamide is obtained; FAB m/z 334 (MH$^{+}$).

A Bischler-Napieralski reaction is carried out on this product, with POCl$_3$ in toluene, in order to obtain 1-methyl-10-methoxyharmalan.

To a solution of 1-methyl-10-methoxyharmalan in pyridine is added acetic anhydride. After acid hydrolysis and extraction with ethyl acetate, the crude product is flash-chromatographed (eluent: EtOAc/pet. ether; 50/50). The 1-methylene-2-acetyl-6-methoxy-9-methyl-1,2,3,4-tetrahydro-β-carboline elutes off first.

Melting point 142–3° C.

NMR: $^1$H (CDCl$_3$): 2.14 (s, 3H, NCOCH$_3$); 2.79 (t, 2H, H-4) 3.80 (s, 3H, NCH$_3$); 3.88 (s, 3H, OCH$_3$); 4.02 (t, 6 Hz, H-3); 5.27 (s, 1H, H vin.); 5.69 (s, 1H, H vin.); 6.89 (dd, H-7); 6.99 (s, 1H, H-5); 7.34 (d, 8.6 Hz, 1H, H-8).

$^{13}$C (CDCl$_3$): 21.6 and 22.4 (C-4 and CH$_3$ amide); 32.4 (CH$_3$-N); 43.3 (C-3); 56.0 (OCH$_3$); 101 and 107.0 (C vin. and C-5); 110.3 and 114.0 (C-7 and C-8); 113.5 (C-4a); 126 and 131.5 and 134.9 (C-5a, C-8a and C-1a); 138.9 (C-1); 155 (C-6); 169.7 (C=O).

Mass spectrum: m/z: 270 (M$^+$), 255, 227 (100), 213.

Exact mass: calculated: 270.1368 found: 270.1370

EXAMPLE 12

1-Methylene-2-acetyl-6,7-dimethoxy-1,2,3,4-tetrahydro-β-carboline

Formula: C$_{16}$H$_{18}$N$_2$O$_3$ M=286.33 g.mol$^{-1}$

To a solution of 10,11-dimethoxyharmalan in pyridine is added acetic anhydride. After acid hydrolysis and extraction with ethyl acetate, the crude product is flash-chromatographed (eluent: EtOAc/pet. ether; 50/50). The 1-methylene-2-acetyl-6,7-dimethoxy-1,2,3,4-tetrahydro-β-carboline elutes off first.

NMR: $^1$H (CDCl$_3$): 2.27, (8, 3H, NCOCH$_3$); 2.82 (t, 6 Hz, 2H, H-4); 3.92 (s, 6H, 2OCH$_3$); 4.11 (t, 6 Hz, H-3); 4.90 (broad s, 1H, H vin.); 5.20 (s, 1H, H vin.); 6.85 and 6.89 (2s, 2H, H-5 and H-B); 7.95 (broad s, 1H, N-H).

Mass spectrum: m/z: 286 (M$^+$), 243, 229

Exact mass: calculated: 286.1317 found: 286.1320

EXAMPLE 13

1-Methylene-2-acetyl-7-.methoxy-1,2,3,4-tetrahydro-β-carboline

Formula: C$_{15}$H$_{16}$N$_2$O$_2$ M=256.30 g.mol$^{-1}$

To a solution of harmaline (200 mg) in dichloromethane (30 ml) is added acetyl chloride (1.2 eq). After reaction for 30 min., triethylamine (1.5 eq) is added. After 5 min., the mixture is-hydrolysed and extracted with CH$_2$Cl$_2$. The crude product is then flash-chromatographed (eluent: EtOAc/pet. ether; 60/40). The 1-methylene-2-acetyl-7-methoxy-1,2,3,4 -tetrahydro-β-carboline[1] elutes off first (yield: 50%).

[1] O. Fisher, Ber, 1897, 30, 2481

Melting point 197–8° C.

NMR: $^1$H (CDCl$_3$): 2.21 (s, 3H, NCOCH$_3$); 2.77 (t, 6 Hz, 2H, H-4); 3.80 (s, 3H, OCH$_3$); 4.03 (t, 6 Hz, H-3); 5.03 (s,

1H, H vin.); 5.49 (s, 1H, H vin.); 6.70 (dd, 8.6 and 2 Hz, H-6); 6.87 (broad s, 1H, H-8); 7.36 (d, 8.6 Hz, 1H, H-5); 10.25 (broad s, 1H, N-H).

$^{13}$C (CD$_3$COCl$_3$): 22.3 and 23.2 (C-4 and CH$_3$ amide); 44.4 (C-3); 56.0 (OCH$_3$); 95.3 (C-8); 101.1 (C vin.); 110.6 (C-6); 113.9 (C-4a); 120.5 (C-5); 122.4 (C-5a); 130.3 (C-1a); 139.4 and 139.6 (C-8a and C-1); 158.7 (C-7); 170.1 (C=O).

Mass spectrum: m/z: 256 (M$^+$), 213 (M-COCH$_3$), 186, 170.

EXAMPLE 14

1-Methylene-2-acetyl-1,2,3,4-tetrahydro-β-carboline
Formula: $C_{14}H_{14}N_2O$ M=226.27 g.mol$^{-1}$ To a solution of harmalan (1 mmol) in pyridine (2 ml) is added acetic anhydride (1.1 eq). After acid hydrolysis and extraction with ethyl acetate, the crude product is flash-chromatographed (eluent: EtOAc/pet. ether; 50/50). The 1-methylene-2-acetyl-1,2,3,4-tetrahydro-β-carboline elutes off first.

Melting point 220–2° C.

NMR: $^1$H (CDCl$_3$): 2.29 (s, 3H, NCOCH$_3$); 2.85 (t, 6 Hz, 2H, H-4); 4.12 (t, 6 Hz, H-3); 4.97 (broad s, 1H, H vin.); 5.35 (s, 1H, H vin.); 6.9–7.5 (m, 4H, aromatic H); 8.4.(broad s, 1H; N-H).

EXAMPLE 15

1-Methylene-2-acetyl-7-methoxy-1,2,3,4, 5,10-hexahydroindol[2,3-c]azepine
Formula: $C_{15}H_{16}N_2O_2$ M=270.33 g.mol$^{-1}$
a: Fisher reaction followed by substitution of the OH with a Cl (PPh$_3$, CCl$_4$);
b: nucleophilic substitution, KCN, 18-C-6;
c: reduction of the nitrile, LiAlH$_4$, H$_2$SO$_4$;
d: acylation, acetic anhydride/pyridine;
e: Bischler-Napieralski reaction;
f: acylation, apetic anhydride/pyridine.

Melting point 190–3.° C.

NMR: $^1$H (CDCl$_3$): 2.14 (m, 2H, H-4); 2.19 (s, 3H, NCOCH$_3$); 2.78 (t, 2H, H-4); 3.78 (t, 2H, H-3); 3.86 (5, 3H, OCH$_3$); 5.03 (s, 1H, H vin.); 5.34 (s, 1H, H vin.);

6.89 (d, 1H, H-8); 6.97 (s, 1H, H-6); 7.20 (d, 1H, H-9); 8.47 (broad s, 1H, N-H).

EXAMPLE 16

6-Methoxy-l-methylene-2-acetyl-2-aza-1,2,3,4-tetrahydrophenanthrene 2-(7-Methoxynaphth-1-yl)ethylamine (1.35mmol) is dissolved in aqueous hydrochloric acid solution (10 ml 0.1 N HCl). 71 pl of ethanal are then added. The mixture is heated at 70° C. for 3 hours. After cooling, the medium is diluted with 10 ml of water and then washed with ether (10 ml). The aqueous phase is basified by addition of 20 ml of 20% sodium hydroxide, and extracted with dichloromethane. The crude product obtained by evaporation of the. dichloromethane is dissolved in anhydrous THF. To the mixture, cooled to 0° C., is added KMnO$_4$ (3.34 g). portionwise over 35 minutes. The mixture is stirred for 1 h and then filtered. After evaporation of the solvent, 6-methoxy-1-methyl-2-aza-3,4-dihydro-phenanthrene is obtained, which product, on acylation (acetic anhydride, pyridine), leads to 6-methoxy-1-methylene-2-acetyl-2.-aza-1,2,3,4-tetrahydrophenanthrene.

Melting, point 171–2° C.

NMR: $^1$H (CDCl$_3$): 2.24 (St .3H, CH$_3$CO); 3.19 (t, 2H, CH$_2$—Ar); 3.92 (s, 3H, OCH$_3$); 4.15 (t, 2H, CH-N); 5.14 and 5.89 (2s, 2H vinylic); 7.17 (d and s, 2H, H-5 and H-7); 7. 60 and 7.51 (2s, 2H, H-9 and H-10) 7.72 (d, 1H, H-8).

MS m/z: 267 (M$^+$), 224, 210, 194, 165, 152.

EXAMPLE 17

7-Methoxy-1-methylene-2-acetyl-2-aza-1,2,3,4-tetrahydrophenanthrene
Formula: $C_{17}H_{17}NO_2$ M=267.32 g.mol$^{-1}$ Synthesis identical to Example 16 starting with 2-(6-methoxynaphth-1-yl)ethylamine.

Melting point 174–5° C.

NMR: $^1$H (CDC 3): 2.23 (s, 3H, CH$_3$CO); 3.22 (t, 2H, CH$_2$—Ar); 3.93 (s, 3H, OCH$_3$); 4.13 (t, 2H, CH$_2$-N); 5.10 and 5.84 (2s, 2H vinylic); 7.13 (d, 1H, H-8); 7.21 (dd, 1H, H-6); 7.63 and 7.67 (2d, 2H, H-9 and H-10); 7.84 (d, 1H, H-5).

MS m/z: 267 (M-), 224, 210, 181, 153.

Exact mass: calculated: 267.1259 found: 267.1260

EXAMPLE 18

1-Methyl-2-acetyl-6-methoxy-1,2, 3,4-tetrahydro-β-carboline
Formula: $C_{15}H_{18}N_2O_2$ M=258.32 g.mol$^{-1}$ Adrenoglomerulotropine[1] (111 mg) is dissolved in anhydrous dichloromethane (3 ml) containing triethylamine (0.08 ml). To the medium, cooled to 0° C., is added dropwise acetyl chloride (0.035 ml) dissolved in dichloromethane (1 ml), and the mixture is left stirring for two hours at room temperature. After evaporation of the solvent, the crude product is chromatographed on a silica plate (eluent: EtOAc/pet. ether; 50/50). 1-methyl-2-acetyl-6-methoxy-1,2,3,4-tetrahydro-β-carboline is thus obtained.

[1] Merck Index 9th Ed. pp. 161.

Melting point 198–200° C.

NMR: $^1$H (CDCl$_3$): 1.45 and 1.51 (2d, 3H, CH$_3$ in position 1); 2.23 (s, 3H, methyl of the amide); 2.76 (m, 2F, H-4); 3.46 and 3.93 (m, 2H, H-3); 3.82 (s, 3H, OCH$_3$); 4.95 and 5.73 (2q, 1H, H-1); 6.83 (dd, H-7); 6.9 (s, 1H, H-5); 7.18 (d, 1H, H-8); 8.5 (broad s, 1H, N-H)

Mass spectrum: m/z: 258 (M.), 243, 215, 201 (100).

Exact mass: calculated: 258.1368 found: 258.1370

EXAMPLE 19

1-(2-Oxa)propyl-2-acetyl-6-methoxy-1,2,3,4-tetrahydro-β-carboline. Formula: $C_1,H_{20}N_2O3$ M=288.34 g.mol$^{-1}$ To 5-methoxytryptamine (256 mg) dissolved in water (9 ml) are successively added hydrochloric acid (0.1 ml) and 1,1,2-trimethoxyethane (0.17 ml). The mixture is heated at reflux for 3 h. The medium is then diluted with hydrochloric acid solution (0.5 N, 40 ml). The aqueous phase is washed with ethyl acetate and then treated with 30% sodium hydroxide solution until the pH is basic. The mixture is then extracted three times with chloroform. After evaporation, 1-(2-oxo)propyl-6-methoxy-1,2,3,4-tetrahydro-β-carboline is obtained.

Treatment of this product with acetyl chloride in dichloromethane in the presence of triethylamine and at 0° C. gives, after chromatographic separation, 1-(2-oxa)-propyl-2-acetyl-6-methbxy-1,2,3,4-tetrahydro-β-carboline.

Melting point 170–1° C.

NMR: $^1$H CDCl$_3$): 2.21 (s, 3H, CH$_3$ amide); 2.75 (m, 2H, H-4); 3.37 (s, 3H, OCH$_3$ on the oxapropyl chain);

3.83 *(s, 3H, OMe at 6); 3.54-4.06 (m, 4H, H-3 and CH$_2$-O); 5.02 and 5.74 (2t, 1H, H-1); 6.83 (dd, H-7);

6.92 (d, 1H, H-5); 7.19 (d, 1H, H-8); 8.53 (broad s, 1H, N-H).

Mass spectrum: m/z: 288 M$^{30}$ ·) , 256, 213, 201 (100).

Exact mass: calculated: 288.1473 found: 288.1470

EXAMPLE 20
1-Trifluoroacetylmethylene-6-methoxy-1,2,3,4-tetrahydro-β-carboline Formula: $C15H_{13}N_2oF_3$ M 310.27 g.mol$^{-1}$ Side product obtained during the preparation of CAFBO4 (1-methylene-2-trifluoroacetyl-6-methoxy-1,2,3,4-tetrahydro-β-carboline).

The 1-trifluoroacetylmethylene-6-methoxy-1,2,3,4-tetrahydro-β-carboline elutes after the 1-methylene-2-trifluoroacetyl6-methoxy-1,2,3,4-tetrahydro-β-carboline.

Melting point 170–4° C.

NMR: $^1$H (CDCl$_3$): 3.10 (t, 2H, H-4); 3.81 (m, 5H, OCH$_3$ and H-3); 5.91 (s, 1H, H vin.); 6.98 (dd, 1H, H-7); 7.14 (d, 1H, H-5); 7.35 (d, 1H, H-8); 10.5 and 10.86 (2 broad s, H-N).

Mass spectrum: m/z: 310 (M$^{30}$ ·), 241 (100), 121.

Exact mass: calculated: 310.0929 found: 310.0927.

EXAMPLE 21
1-(Ethoxycarbonyl)methylene-6-methoxy-1,2,3,4-tetrahydro-β-carboline Formula: $C_{14}H_{18}N_2O_2$ M=286.33 g.mol$^{-1}$ $^{ENA}$2 is, obtained by a Bischler-Napieralski reaction on N-[2-(5-methoxyindol-3-yl)ethyl]ethoxy-carbonylacetamide. This product is obtained by condensation of diethyl malonate with 5-methoxytryptamine.

NMR: $^1$H (CDCl$_3$): 1.29 (t, 3H, CH$_3$ ethoxy); 2.95 (t, 2H, H-4); 3.56 (td, 2H, H-3); 3.86 (s, 3H, OCH$_3$); 4.17 (q, 2H, CH$_2$ ethoxy); 4.88 (broad s, 1H, H vin.); 6.94 (d, H-7); 6.96 (s, 1H, H-5); 7.26 (d, 1H, H-8); 8.04 and 8.30 (2 broad s, 2H, N $^1$H).

Mass spectrum: m/z: 286 (M$^{30}$ ·), 240 (100), 225, 164

EXAMPLE 22
9-Methoxy-2,3,4,6,7,12-hexahydroindolo[2,3-a]quinolizin-4-one

Formula: $C_{16}H_{16}N_2O_2$ M=68.31 g.mol$^{-1}$

A mixture of 5-methoxytryptamine (420 mg) and diethyl glutarate (460 mg) is heated at 175° C. for 18 h. eparation on a column (eluent: EtOAc) gives the amide ster 2. This product is treated with a trace of ara-toluenesulphonic acid in xylene and the water formed is removed using Dean-Stark apparatus. After refluxing for 9 h and separation on a silica plate, N-[2-(5-methoxy)indol-3-ylethyl)]glutarimide is obtained.

To a solution of N-[2-(5-methoxy)indol-3-yl-ethyl)] glutarimide (100 mg) in refluxing xylene is added phosphorus pentoxide (1.5 g) with stirring. After refluxing for 5 hours, the reaction medium is filtered. The solid is taken up in water, basified (KOH, 40%) and then extracted with ethyl acetate. After removal of the solvent, the 9-methoxy-2,3,4, 6,7,12-hexahydroindolo-[2,3-a]quinolizin-4-one is purified on a silica plate (eluent: EtOAc/pet. ether; 50/50).

Melting point 212–4° C.

NMR: $^1$H (CDCl$_3$): 2.46 and 2.63 (2 mn, 1H and 3H, 2H-2 and 2H-3); 2.87 (m, 2H, H-6); 3.85 (s, 3H, OCH$_3$; 4.10 (m, H-7); 5.50 (t, 1H, H-1); 6.87 (m, 1H, H-10); 6.94 (s, 1H, H-8); 7.22 (di 1H, H-11); 11.67 (broad s, 1H, H-12).

Mass spectrum: m/z: 268 M$^{30}$ ·), 216, 187, 173, 159 (100).

Exact mass: calculated: 268.1211 found: 268.1210

EXAMPLE 23
2,3,4,6,7,12$^1$Hexahydroindolo[2,3-a]quinoliziri-4-one

Formula: $C_{15}H_{14}N_2O$ M=238.28 g.mol$^{-1}$

Preparation: Ref. G. C. Morrison, W. Cetenko, J. Shavel Jr.; J. Chem. Soc., 1964, 2771.

NMR: $^1$H (CDCl$_3$): 2.49 and 2.60 (2 m, 4H, H-2 and H-3); 2.91 (t,. 2H, H-6); 4.12 (m, H-7); 5.51 (t, 1H, H-1); 7.12 and 7.26 (2t, 2H, H-9 and H-10); 7.35 and 7.53 (2t, 2H, H-8 and H-11); 8.03 (broad s, 1H, H-12)

Mass spectrum: m/z: 238 (M$^+$·), 223, 209, 195, 167

EXAMPLE 24
2-Acetyl-6-methoxy-1-oxo-1,2,3,4-tetrahydro-β-carboline

Formula: $C_{14}H N_2O$ M=258.27 g.mol$^{-1}$

Ref: I. J. Pachter, R. H. Mohrbacher, D. E. Zacharias, J. Am; Chem. Soc., 83, 635 (1961).

Melting point 215–220° C. NM?: 1H (DMSO-d$_6$): 2.52 (s, 3H, NCOCH$_3$); 2.99 (broad s, 2H, H-4; 3.78 (s, 34, OCE,) 4.22 (broad, H-3) 6.95 (m, 1H, H-7) 7.02 (s, 1H, H-5) 7.31 (c, 1H, H-8); 11.67 (broad s, 1H, N-H)

EXAMPLE 25

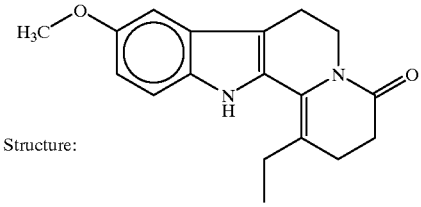

Formula: $C_{18}H_{20}N_2O_2$    M = 296.36g.mol$^{-1}$

Structure:

ETCARBO7: 9-metioxy-1-ethyl-2,3,4,6,7,12-hexahydroindolo[2,3]-quinolizin-4-one

Preparation:

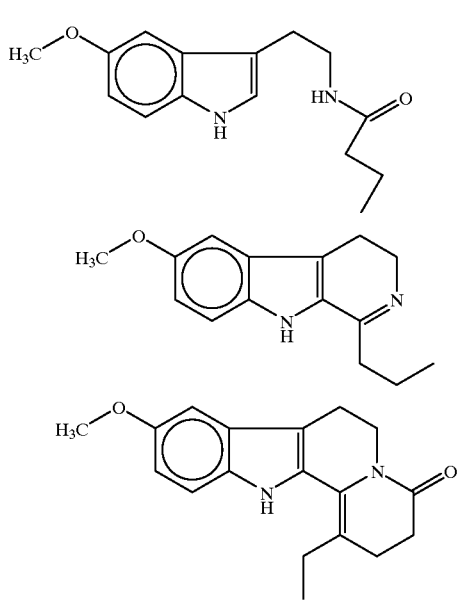

A Bischler-Napieralsk)i reaction on N1-(2-(5-methoxy-1H-3-indolyl)butanamide leads to the carboline 1.

Method 1:

Acrylic acid (0.71 mL, 1.1 eq.) is added to a solution of carboline 1 (2.34) in DMF (20 ml). Diphenylphosphoryl azide (2.1 mL, 1.06 eq.) dissolved in DMF (3 mnL) is then added dropwise, followed by triethylamine (2.85 mL, 2.1 eq.). After recrystallization from ethyl acetate, 9-methoxy-1-ethyl-2,3,3,6,7,12-hexahydroindolo[2,3-a]-quinolizin-4-one is recovered (1.6 g, 56%).

Method 2:

Acrylic acid (1 eq.) dissolved in xylene is added to a solution of catboline 1 in xylenc. The reaction flask is equipped with a wvater separator and the medium is heated to reflux of the xylene for 24 h. The xylene is then distilled off under reduced pressure. The product is purified as above.

NMR: $^1$H (CDCl$_3$): 1.29 (t, 3H); 2.44 and 2.54 (2ni, 61G): 2.86 (t, 924); 3.86 (s, 3H); 4.08 (t, 2H); 6.87 (dd 2.4 and 8.7 Hz, 111); 6.95 (d 2.4 Hz, 111); 7.27 (d 8.7 Hz, 1H); 8.04 (broad s, 1H)

Mass spectrum: m/z: 296(M$^+$), 281(100)
Exact mass: calculated 296.1524 found 296.1545

EXAMPLE 26

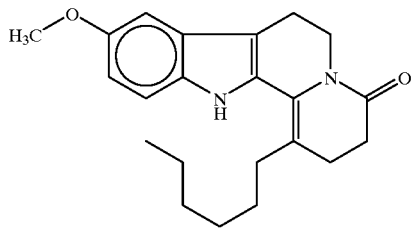

Formula: C$_{22}$H$_{28}$N$_2$O$_2$  M = 352.47 g.mol$^{-1}$
Structure:

HECABO7 9-methoxy-1-hexyl-2,3,4,6,7,12-hexahydroindolo[2,3-a]quinolizin-4-one
Preparation:

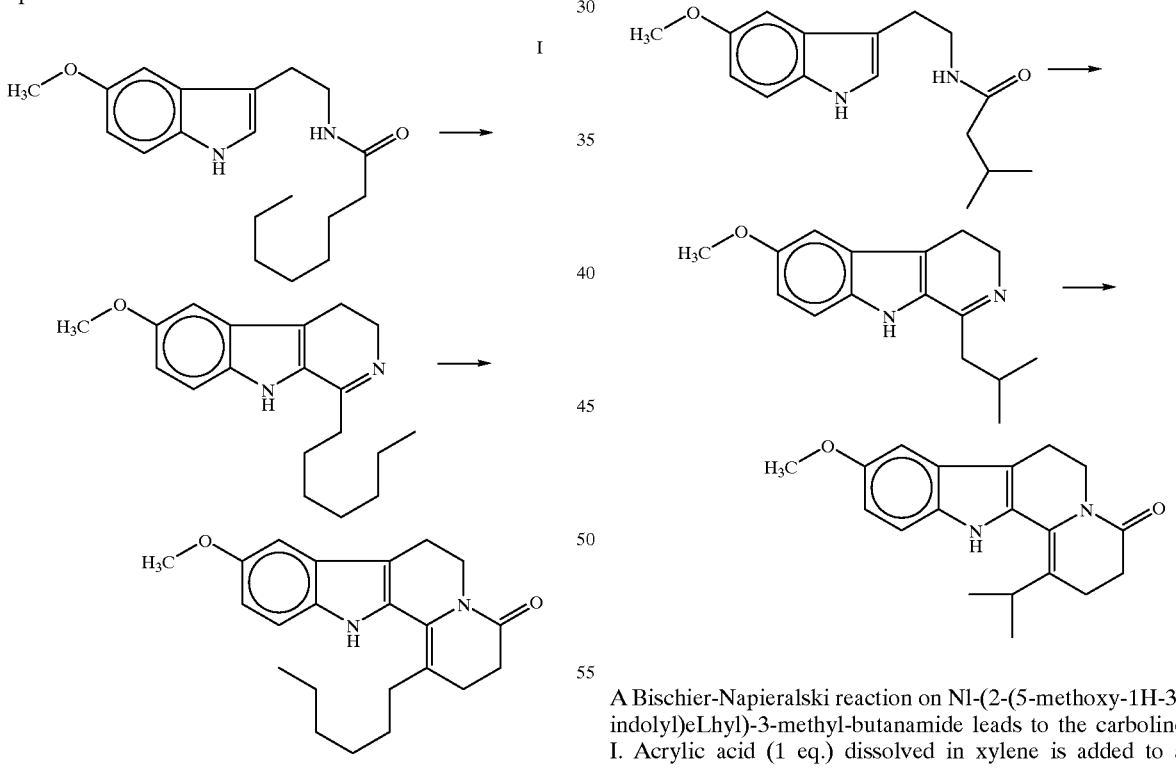

A Bischler-Napieralski reaction on N1-(2-(5-methoxy-IH-3-indolyl)ethyl)octanamide leads to the carboline I. Acrylic acid (1 eq.) dissolved in xylene is added to a solution of carboline 1 in xylene. The reaction flask is equipped ivith a water separator and thc medium is heated to reflux of the xylene for 48 h. The xylene is then distilled off under reduced pressure. The product is recrystallized from ethyl acetate.

NMR: $^1$H (CDCl$_3$): 0.92 (t, 3H); 1.42 (m, 8H); 2.40 (t, 2H); 2.50 (m, 4H); 2.56 (t, 2H); 3.86 (s, 3H); 4.08 (t, 2H); 6.87 (dd 2.4 and 8.7 Hz, H); 6.94 (d 2.4 Hz, 1H); 7.23 (d 8.7 Hz, 1H); 8.04 (broad s, 1H)

Mass spectrum: m/z: 352(M$^{30}$ ·), 281(100)

EXAMPLE 27

IPCARBO7: 9-methoxy-1-isopropyl-2,3,4,6,7,12-hexahydroindolo[2,3-a]quinolizin-4-one
Preparation:

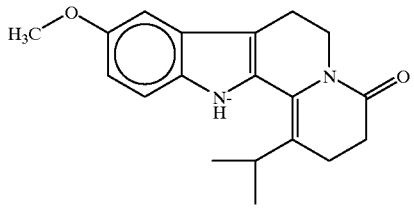

Formula: C$_{19}$H$_{22}$N$_2$O$_2$  M = 310.39 g.mol$^{-1}$
Structure:

IPCARBO7: 9-methoxy-1-isopropyl-2,3,4,6,7,12-hexahydroindolo[2,3-a]quinolizin-4-one
Preparation:

A Bischier-Napieralski reaction on N1-(2-(5-methoxy-1H-3-indolyl)eLhyl)-3-methyl-butanamide leads to the carboline I. Acrylic acid (1 eq.) dissolved in xylene is added to a solution of carboline 1 in xylene. The reaction flask is equipped with a water separator and the medium is heated to reflux of the xylene for 48 h. The xylene is then distilled off under reduced pressure. The product is recrystallized from ethyl acetate.

NMR: $^1$H (CDCl$_3$): 1.20 (d, 6H); 2.35 and 2.47 (2m, 4H); 2.87 (t, 2H); 3.38 (m, 1H); 3.86 (s, 3H); 4.06 (t,2H); 6.87 (dd 2.4 and 9 Hz, 1H); 6.95 (d 2.4 Hz, 1H); 7.32 (d 9 Hz, 1H);

Mass spectrum: m/z: 310(M$^+$), 295(100)

EXAMPLE 28

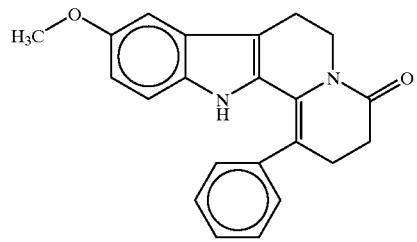

Formula: $C_{22}H_{20}N_2O_2$     M = 344.41 g.mol$^{-1}$
Structure:

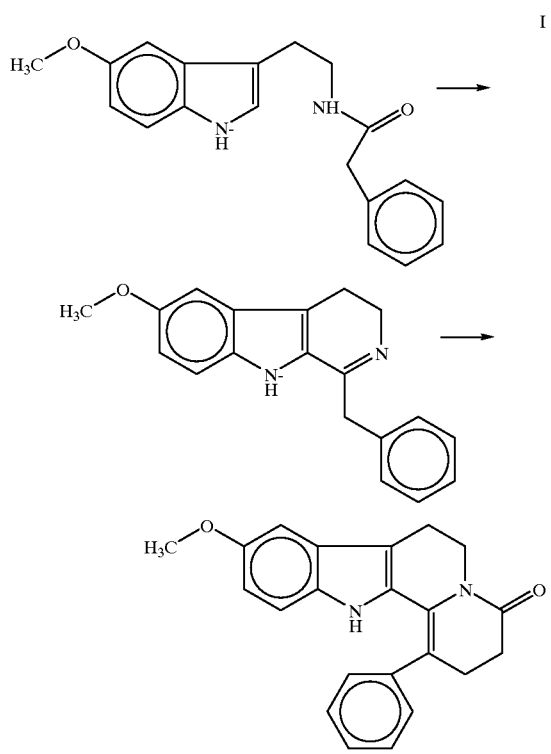

PHCARBO7: 9-methoxy-1-phenyl-2,3,4,6,7,12-hexahydroindolo[2,3-a]quinosizin-4-one
Preparation:

A Bischler-Napieralski reaction on N1-(2-(5-methoxy-1H-3-indolyl)ethyl)-2-phenyl-acetamide leads to the carboline 1. Acrylic acid (0.75 mL, 1.1 eq.) is added to a solution of carboline 1 (2.8 g) in DMF (20 mL). Diphenylphosphoryl azide (2.1 mL, 1.06 eq.) dissolved in DMF (3 mL) is then added dropwise, followed by triethylamine (2.85 mL, 2.1 eq.). After separation on silica gel (chloroformi/methanol eluent), 9-methoxy-1-phenyl-2,3,4,6,7,12-hexahydro-indolo[2,3-a]quinolizin-4-one is recovered (1.6 g, 56%).

NMR: $^1$H (CDCl$_3$): 2.71 (m, 4H); 2.91 (t, 2H); 3.83 (s, 3H); 4.20 (2H); 6.76 (dd 2.4 and 8.7 Hz, 1H); 6.84 (d 8.7 Hz, 1H); 6.90 (d 2.4 Hz, 1H); 6.93 (broad s, 1H); 7.42 and 7.50 (m, 5H)

Mass spectrum: m/z: 344(M$^+$)(100), 253

EXAMPLE 29

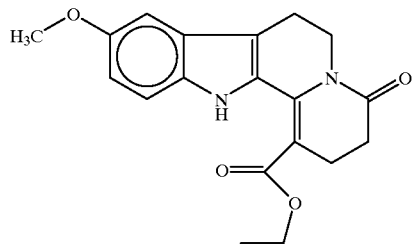

Formula: $C_{19}H_{20}N_2O_4$     M = 340.37 g.mol$^{-1}$
Structure:

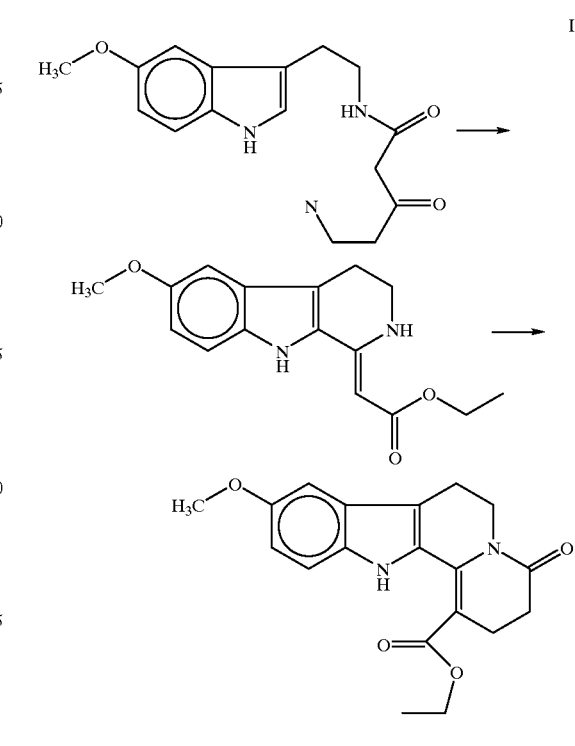

CO2ETCARBO7: 1-carbethoxy-9-methoxy-2,3,4,6,7,12-hexahydroindolo[2,3-a]quinolizin4-one
Preparation:

A Bischler-Napieralski reaction on ethyl 3-((2-(5-methoxy-1H-3-indolyl)ethyl)amino)-3-oxopropanoate leads to the carboline I. Sodium hydroxide solution (1 N, 3 mL) is added to a solution of the carboline I obtained (800 mg) in benzene (10 mL), followed by tetrabutylammonium hydrogen sulphate (0.1 eq.). Acryloyl chloride (0.27 mL) is then added at 0° C. and the mixture is allowed to return to room temperature overnight. The product is separated on silica gel (chloroform/methanol) and 1 -carbethoxy-9-methoxy-2,3,4, 6,7, 1 2-hexahydroindiolo-[2,3-a]quinolizin-4-one is thus obtained.

NMR: $^1$H (CDCl$_3$): 1.42 (t, 3H); 2.60 (t, 2H); 2.85 (t, 2H); 2.97 (t, 2H); 3.89 (s, 3H); 4.30 (t, 2H); 4.35 (q, 2H); 6.96 (d 2.1 Hz, 1H); 7.01 (dd 2.1 and 7.5 Hz, 1H); 7.35 (d 7.5 Hz, 1H);

Mass spectrum: m/z: 340(M$^+$), 294(100)

EXAMPLE 30

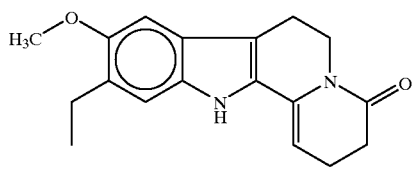

Formula: $C_{20}H_{24}N_2O_2$  M = 324.42 g.mol$^{-1}$
Structure:

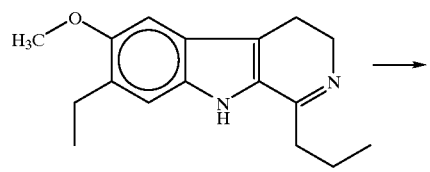

6ETETCARBO7: 9-methoxy-10-diethyl-2,3,4,6,7,12-hexahydroindolo[2,3-a]quinolizin-4-one Preparation:

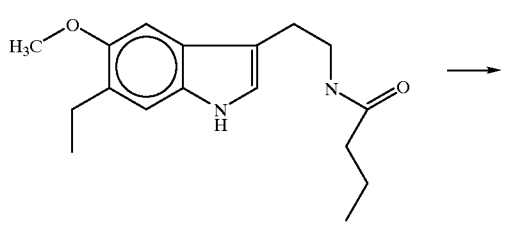

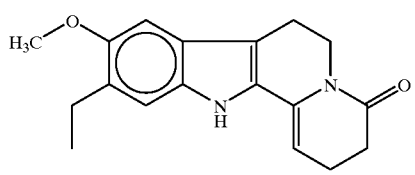

A Bischier-Napieralski reaction on N1-(2-(5-methoxy-6-ethyl- 1H-3-indolyl)ethyl)-butanamide leads to the carboline I. Acrylic acid (0.22 mL, 1.1 eq.) is added to a solution of carboline 1 (764 mg) in DMF (20 mL). Diphenylphosphoryl azide (1.06 eq.) dissolved in DMF (3 mL) is then added dropwise, followed by triethylamine (2.1 eq.). After separation on silica gel (chloroform/methanol eluent) 9-methoxy-1,10-diethyl-2,3,4,6,7,12-hexahydroindoio[2,3-a]-quinolizin-4-one is recovered (28%).

NMR: $^1$H (CDCl$_3$): 1.26 (m, 6H); 2.41 axid 2.58 (2m, 6H); 2.70 (q, 2H); 2.87 (t, 2H); 3.87 (s, 31H); 4.07 (t, 2H); 6.88 (1s, 1H); 7.19 (s, 1H); 8.33 (broad s, 1H).

Mass spectrum: m/z: 324(M$^+$), 309(100)

EXAMPLE 31

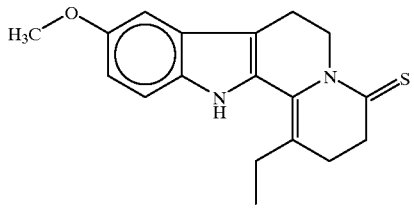

Formula: $C_{18}H_{20}N_2OS$  M = 312.42 g.mol$^{-1}$
Structure:

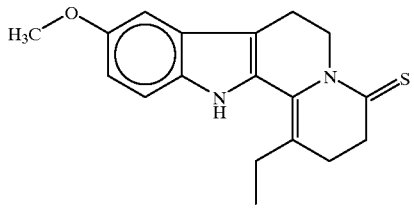

ETCARBO7S: 9-methoxy-1-ethyl-2,3,4,6,7, 1 2-hexahydroindolo[2,3-a]quinolizine-4-thione Preparation:

Lawesson's reagent (0.5 nimol) is added portionwise, at 110° C., to a solution of 9-metlioxy-1-ethyl-2,3,4,6,7,12-hexahydroindolo[2,3-a]quinoIizin-4-one (300 mg, 1.01 mmol) in anhydrous toluene (15 mL). After refluxing for 30 min. and evaporation of the toluene, the product is chromatographed on silica gel (99/1 chloroform/methanol eluent) and 9-methoxy-1-ethyl-2,3,4,6,7,12-hexahydroindolo[2,3-alquinolizine-4-thione is thus recovered (60% yield).

NMR: $^1$H (CDCl$_3$): 1.32 (t, 3H); 2.32 (t, 2H), 2.65 (q, 2H); 2.98 (t, 2H); 3.08 (t, 2H); 3.89 (s, 3H); 4.80 (t, 2H); 6.91 (dd 2.4 and 8.7 Hz, 1H); 6.98 (d 2.4 Hz, 1H); 7.34 (d 8.7 Hz, 1H); 8.11 (broad s, 1H)

Mass spectrum: m/z: 312(M$^+$)(100), 297

EXAMPLE 32

IMCARBO7

Formula: $C_{17}H_{18}N_2O_2$  M = 282.34 g.mol$^{-1}$
Structure:

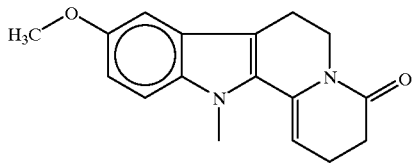

1MCARBO7: 9-methoxy-12-methyl-2,3,4,6,7,12-hexahydroindolo[2,3-a]quinolizin-4-one Preparation:
Method 1:
Acrylic acid (0.37 mL, 1.1 eq.) is added to a solution of I-methyl-I 0-methoxyharmalan (1.11 g) in DMF (20 mL). Diphenylphosphoryl azide (10.6 mL, 1.06 eq.) dissolved in DMF (3 mL) is then added dropwise, followed by triethylamine (1.45 mL, 2.1 eq.). After stirring the mixture for 7 h at room temperature, the DMF is evaporated off and the crude product is chromatographed on silica gel (EtOAc/pet ether eluent). 9-Methoxy-12-methyl-2,3,4,6,7,12-hexahydroindolo[2,3-a]quinolizin-4-one is thus recovered.
Method 2:
Acrylic acid (442 mg) dissolved in xylene (1.5 mL) is added to a solution of 1-methyl-10-methoxyharmalan (1.4 g) in xylene (65 mL). The reaction flask is equipped with a water separator and the medium is heated at the reflux point of xylene for 24 h. The xylene is then distilled off under reduced pressure. The product is purified as above.

NMR: $^1$H (CDCl$_3$): 2.49 and 2.56 (2m, 4H); 2.85 (t, 2H); 3.83 (s, 3H); 3.85 (s, 3H); 4.04 (t, 2H); 5.74 (t, 1H); 6.90 (s and d, 2H); 7.18 (d 8 Hz, 1H);

Mass spectrum: m/z: 282(M$^{30}$·)(100), 267, 253

Exact mass: calculated 282.1368 found 282.1364

EXAMPLE 33

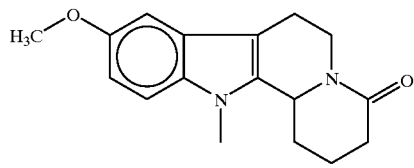

Formula: C$_{17}$H$_{20}$N$_2$O$_2$    M = 284.35 g.mol$^{-1}$
Structure:

1MDHCARBO7: 9-methoxy-12-methyl-1,2,3,4,6,7,12,12b-octahydroindolo[2,3-a]quinolizin4-one Preparation:

Hydrogenation of 9-methoxy-12-methyl-2,3,4,6,7,12-hexahydroindolo[2,3-a]quinolizin-4-one with hydrogen in the presence of palladium-on-charcoal and sodium bicarbonate leadsto9-methoxy-12-methyl-1,2,3,4,6,7,12,12b-octahydroindolo[2,3a]quinolizin-4-one NMR: $^1$H (CDCl$_3$): 1.75–1.9 (m, 2H); 1.97 (m, 2H); 2.5 (m, 2H); 2.8 (m, 2H); 2.87 (m, 1H); 3.72 (s, 3H); 3.85 (s, 3H); 4.79 (m, 1H); 5.15 (m, 1H); 6.84 (dd 2.4 and 8.7 Hz, 1H); 6.95 (d 2.4 Hz, 1H); 7.2 (d 8.7 Hz, 1H)

EXAMPLE 34

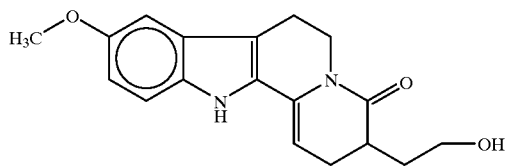

Formula: C$_{18}$H$_{20}$N$_2$O$_3$    M = 312.36 g.mol$^{-1}$
Structure:

ALCARB07: 3-(P-hydroxyethyl)-9-methoxy-2,3,4,6,7,12-hexahydroindolo[2,3-a]quinolizin4-one Preparation:

α-Methylene-γ-butyrolactone (0.18 mL) is added to a solution of 10-methoxyharmalan (404 mg) in acetonitrile. The mixture is refluxed for 5 h and the solvent is then evaporated off. The crude product is chromatographed on silica gel (dichloromethane/methanol). 3-(β-Hydroxyethyl)-9-methoxy-2,3,4,6,7,12-hexahydroindolo[2,3-a]quinolizin-4-one is thus recovered.

NMR: $^1$H (DMSO-d6): 1.50 (m, 1H); 2–2.15 (m, 2H); 2.18–2.51 (mn, 2H); 2.75 (m, 2H); 3.55–3.65 (m, 2H); 3.71 (s, 3H); 4.25 (t, 2H); 5.35 (s, 1H); 5.70 (broad s, 1H); 6.64 (d 7 Hz, H); 6.79 (s, $^1$H); 6.72 (d 7 Hz, ]H); 7.71 (s, 1H)

EXAMPLE 35

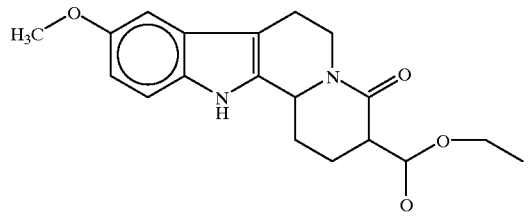

Formula: C$_{19}$H$_{22}$N$_2$O$_4$    M = 342.39 g.mol$^{-1}$
Structure:

CARBO21: ethyl 9-methoxy-4-oxo-1,2,3,4,6,7,12,12b-octahydropyrido[2,1-a]-β-carboline-3-carboxylate Preparation:

4,4-Dicarbethoxybutyronitrile (1.2 g) and palladium-on-charcoal (0.6 g) are successively added to 5-methoxytryptamine (693 mg) dissolved in acetic acid. The mixture is stirred under a hydrogen atmosphere for 48 h. The medium is then filtered and the palladium is washed with a chloroform/methanol mixture. After evaporation of the solvent, the crude product obtained, dissolved in toluene, is refluxed overnight. The ethyl 9-methoxy-4-oxo-1,2,3,4,6,7,12,12b-octahydropyrido[2,1 -a]-(3-carboline-3-carboxylate precipitates and is recovered by simple filtration (35% yield).

NMR: $^1$H (CDCl$_3$): 1.30 (t, 3H); 1.95 (m, 2H); 2.35 (m, 2H); 2.6 (m, 1H); 2.85 (in, 2H); 3.4 (t, 1H); 3.84 (s, 3H); 4.24 (m, 2H); 4.8 (m, 1H); 5.15 (m, 1H); 6.85 (dd 9 and 2.4 Hz, 1H); 6.95 (d 2.4 Hz, 1H); 7.23 (d 9 Hz, 1H); 7.9 (broad s, 1H)

Mass spectrum: m/z: 342(M$^+$)(100), 297, 269, 214

Exact mass: calculated 342.1579 found 342.1577

EXAMPLE 36

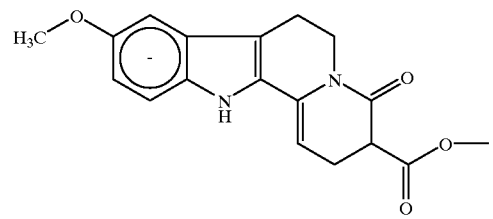

Formula: C$_{18}$H$_{18}$N$_2$O$_4$    M = 326.35 g.mol$^{-1}$
Structure:

1MCARBO7: methyl 9-methoxy-4-oxo-2,3,4,6,7,12-hexahydropyrido[2,1 -a]β-carboline-3-carboxylate Preparation:

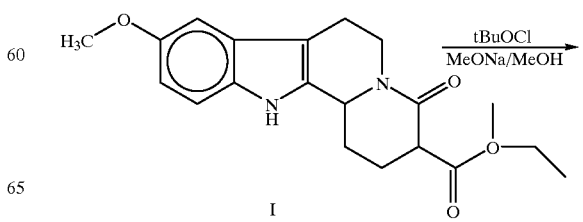

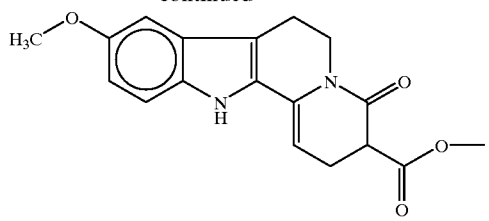

Triethylamine (0.25 mL) and tert-butyl hypochlorite (70 mg dissolved in 3 mL of dichloromethane) are successively added to a solution of carboline 1 (203 mg) in dichloromethane (25 mL), cooled to −10° C. After stirring for two hours, sodium methoxide is added (1 mL of a 1M solution in methanol). The medium is diluted with dichloromethane and washed with water. After drying (MgSO$_4$) and evaporation of the solvent, the crude product is chromatographed on silica gel. Methyl 9-methoxy-4-oxo-2,3,4,6,7,12-hexahydropyrido[2,1-a]-β-carboline-3-carboxylate is thus recovered.

NMR: $^1$H (CDCl$_3$): 2.92 (t, 2H); 3.76 (s, 3H); 3.85 (s, 3H); 4.12 (t, 2H); 5.47 (t, 1H); 6.88 (dd 3 and 9 Hz, 1H); 6.94 (d 3 Hz, 1H); 7.24 (d 9 Hz, 1H); 8.03 (broad s, 1H)

Mass spectrum: m/z: 326(M$^{+\cdot}$), 267(100), 133

Exact mass: calculated 326.1266 found 326.1275

EXAMPLE 37

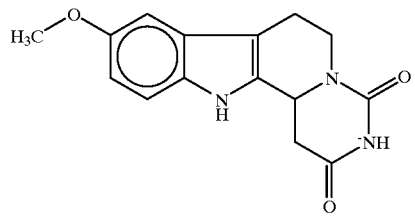

Formula: C$_{15}$H$_{15}$N$_3$O$_3$  M = 285.28 g.mol$^{-1}$
Structure:

CARBO22: 9-methoxy-1,2,3,4,6,7,12,12b-octahydropyrirnido[6,1-a]-βcarboline-2,4-dione Preparation:

Ethyl cyanoacetylcarbamate (156 mg) and palladium-on-charcoal (0.6 g) are successively added to 5-methoxytryptamine (119 mg) dissolved in acetic acid. The mixture is stirred under a hydrogen atmosphere for 72 h. The medium is then filtered and the palladium is washed with a chloroform/methanol mixture. After evaporation of the solvent, the crude product obtained, dissolved in toluene, is refluxed overnight. The 9-methoxy-1,2,3,4,6,7,12,12b-octahydropyrimido[6,1-a]-β-carboline-2,4-dione precipitates and is recovered by simple filtration (40% yield).

NMR: $^1$H (CDCl$_3$): 2.48 (m, 1H); 2.72 (m, 2H); 3.0 and 3.20 (m, 2H); 3.71 (s, 3H); 4.6 (m, 1H); 4.9 (m, 1H); 6.66 (d 8.7 Hz, 1H); 6.82 (s, 1H); 7.11 (d 8.7 Hz, 1H);

Mass spectrum: m/z: 285(M$^{+\cdot}$)(100), 199, 186

EXAMPLE 38

BACARBO7: 9-methoxy-2,3,4,6,7,12-hexahydropyrimido[6,1-a]-β-carboline-2,4-dione

Preparation:

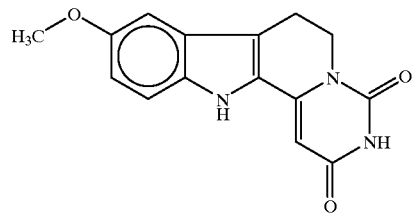

Formula: C$_{15}$H$_{13}$N$_3$O$_3$  M = 283.28 g.mol$^{-1}$
Structure:

BACARBO7: 9-methoxy-2,3,4,6,7,12-hexahydropyrimido[6,1-a]-β-carboline-2,4-dione

Preparation:

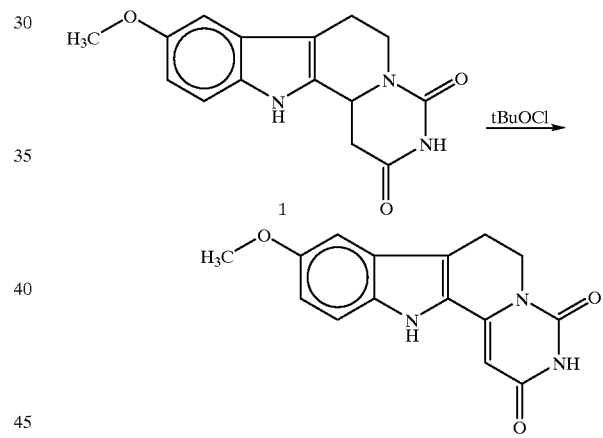

Triethylamine (0.25 mL) and tert-butyl hypochlorite (70 mg dissolved in 3 mL of dichloromnethane) are successively added to a solution of carboline 1 (78 mg) in dichloromethane (25 mL), cooled to -10° C. After reaction for two hours, the mediurn is diluted with dichloromethane and washed with water. Afher drying (MgSO$_4$) and evaporation of the solvent, the product is recrystallized from ethyl acetate. 9-Nqethoxy-2,3,4,6,7,12-hexahydropyrimido[6,1-a]-β-carboline-2,4-dione is thus recovered.

NMR: $^1$H (CDCl$_3$): 3.09 (t, 2H); 3.80 (s, 3H); 4.17 (t, 2H); 6.07 (s, 1H); 6.86 (dd 3 and 9 Hz, 1H); 6.97 (d 3 Hz, 1H); 7.31 (d 9 Hz, 1H);

Mass spectrum: m/z: 283M$^{30}$ ·), 197(100), 184

Exact mass: calculated 283.0956 found 283.0973

EXAMPLE 39

6ETCARBO7

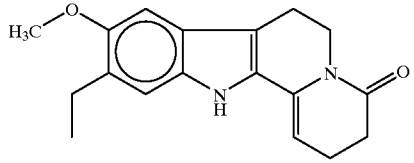

Formula: $C_{18}H_{20}N_2O_2$  M = 296.36 g.mol$^{-1}$
Structure:

6ETCARBO7: 9-methoxy-10-ethyl-2,3,4,6,7,12-hexahydroindolo[2,3-a]quinolizin-4-one Preparation:

Acrylic acid (0.23 mL) is added to a solution of 7-ethyl-6-methoxy-1-methyl-3,4-dihydro-β-carboline (740 mg, 3.05 mmol) in DMF (6 mL), followed by dropwise addition of diphenylphosphoryl azide dissolved in DMF (1.5 mL). The medium is left stirring for 6 h. Separation on silica gel allows the 9-methoxy-10-ethyl-2,3,4,6,7,12-hexahydroindolo[2,3-a]quinolizin4-one to be recovered (23% yield).

NMR: $^1$H (CDCl$_3$): 1.22 (t, 3H); 2.41 and 2.57 (2m, 4H); 2.67 (q, 2H); 2.83 (t, 2H); 3.84 (s, 3H); 4.04 (t, 2H); 5.51 (t, 1H); 6.85 (s, 1H); 7.07 (s, 1H); 8.86 (broad s, 1H)

Mass spectrum: m/z: 296(M$^+$)(100), 281, 267, 253

Exact mass: calculated 296.1524 found 296.1518

EXAMPLE 40

DECARBO7

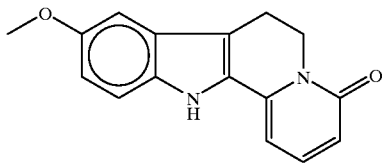

Formula: $C_{16}H_{14}N_2O_2$  M = 266.29 g.mol$^{-1}$
Structure:

DECARBO7: 9-methoxy-1,6,7,12-tetrahydroindolo[2,3-a]quinolizin-4-one

Preparation:

Activated manganese dioxide (400 mg) is added to a solution of 9-methoxy-2,3,4,6,7,12-hexahydroindolo[2,3-a]quinolizin-4-one (150 mg) in THF (5 ml). After refluxing for 2 h 30, the mixture is cooled and activated manganese dioxide (400 mg) is again added. The medium is refluxed for 2 h 30. After filtration and washing of the dioxide with an ethyl acetate/methanol mixture (98/2) and after separation on a preparative plate, 9-methoxy4,6,7,12-tetrahydroindolo[2,3-a]quinolizin-4-one is obtained (55% yield).

NMR: $^1$H (CDCl$_3$): 2.97 (t, 2H); 3.74 (s, 3H); 4.28 (t, 2H); 6.3 (d, 1H); 6.57 (d, 1H); 6.78 (d, 1H); 6.88 (s, 1H); 7.22 (d, 1H); 7.29 (t, 1H); 7.80 (broad s, 1H);

Mass spectrum: m/z: 266 (M-, 100), 265

Exact mass: calculated 266.1055 found 266.1050

EXAMPLE 41

DDCARBO7

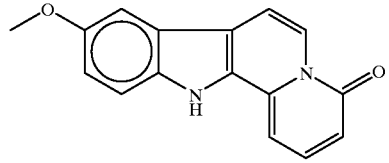

Formula: $C_{16}H_{12}N_2O_2$  M = 264.29 g.mol$^{-1}$
Structure:

DECARBO7: 9-methoxy-4,12-dihydroindolo[2,3-a]quinolizin-4-one

Preparation:

Activated manganese dioxide (400 mg) is added to a solution of 9-methoxy-2,3,4,6,7,12-hexahydroindolo[2,3-a]quinolizin-4-one (150 mg) in THF (5 ml). After refluxing for 2 h 30, the mixture is cooled and activated manganese dioxide (400 mg) is again added. The medium is refluxed for 24 h. After filtration ard washing of the dioxide with an ethyl acetate/methanol mixture (98/2), and after recrystallization from ethyl acetate, 9-methoxy4,12-dihydroindolo[2,3-a]quinolizin-4-one is obtained.

NMR: $^1$H (CDCl$_3$): 3.83 (s, 3H); 6.4 (d, 1H); 7.03 (d, 1H); 7.20 (d, 1H); 7.40 (m, 2H); 7.63 (m, 2H); 8.80 (broad s, 1H);

Mass spectrum: m/z: 264(M$^+$, 100), 236

Exact mass: calculated 264.0898 found 264.0906

EXAMPLE 42

CICARBO7

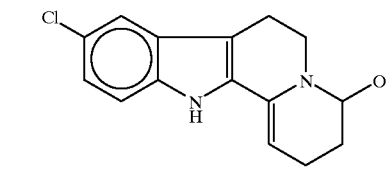

Formula: $C_{15}H_{13}N_2OCl$  M = 272.73 g.mol$^{-1}$
Structure:

CICARBO7: 9-chloro-2,3,4,6,7,112-hexahydroindolo[2,3-a]quinolizin-4-one

Preparation:

Acrylic acid (1.1 eq.) is added to a solution of 10-chloroharrnalan (1 mmol) in DlvlF (2 mL). Diphenylphosphoryl azide.(l eq.) dissolved in DMF (3 mL) is then added dropwise, followed by triethylamine (2.1 eq.). After stirring the mixture for 7 h at room temperature, the DMF is evaporated off and the crude product is chrornatographed on silica gel (EtOAc/pet. ether eluent). The 9-chloro-2,3,4,6,7,2-hexahydroindolo-[2,3-a]quinolizin4-one is thus recovered.

NMR: $^1$H (CDCl$_3$): 2.47 and 2.57 (2m, 4H); 2.84 (t, 2H); 4.10 (t, 2H); 5.87 (t, 1H); 7.07 (d 9 Hz, 1H); 7.33 (dd 9 and 3 Hz, 1H); 7.41 (d 3 Hz, 1H);

Mass spectrum: m/z: 272(M$^+$, 100), 257, 243

EXAMPLE 43

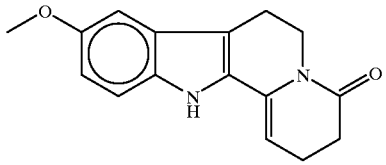

Formula: $C_{16}H_{18}N_2O_2$      M = 270.33 g.mol$^{-1}$
Structure:

DHCARBO7: 9-methoxy-1,2,3,4,6,7,12,12b-octahydropyrido[2,1-a]-β-carbolin-4-one

Preparation:

Catalytic hydrogenation of 9-methoxy-2,3,4,6,7,12-hexahydropyrido[2,1 -a]-β-carbolin-4-one with active palladium-on-charcoal in the presence of hydrogen and sodium bocarbonate gives 9-methoxy-1,2,3,4,6,7,12,12b-octahydropyrido[2,1-a]-β-carbolin-4-one quantitatively.

NMR: $^1$H (CDCl$_3$): 1.75–1.9 (m, 2H); 1.95 (m, 2H); 2.45 and 2.6 (m, 2H); 2.8 (m, 2H); 2.87 (m, 1H); 3.87 (s, 3H); 4.78 (m, 1H); 5.17 (m, H); 6.84 (dd 8.7 and 2.4 Hz, 1H); 6.96 (d 2.4 Hz, 1H); 7.23 (d 8.7 Hz, 11); 8.23 (broad s, 1H)

Mass spectrum: m/z: 270(M$^+$)(100), 199

EXAMPLE 44

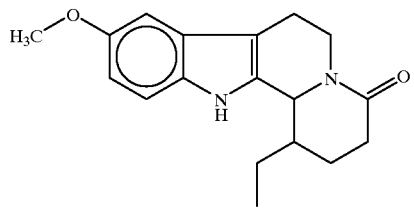

Formula: $C_{18}H_{22}N_2O_2$      M = 298.38 g.mol$^{-1}$
Structure:

ETDHCARBO7: 9-methoxy-1-ethyl-1,2,3,4,6,7,12,12b-octahydroindolo[2,3-a]quinolizin4-one Preparation:

Sodium bicarbonate (500 mg) and palladium-on-charcoal are successively added to a solution of 9-methoxy-1-ethyl-2,3,4,6,7,12-hexahydroindolo[2,3-a]quinolizin-4-one (500 mg) in ethanol. and the mixture is stirred overnight under a hydrogen atmosphere. After filtration and evaporation of the solvent, the crude product is recrystallized from ethyl acetate. 9-Methoxy-I-ethyl-1,2,3 ,4,6,7,12,12b-octahydroindolo[2,3-a]quinolizin-4-one is thus recovered (76%).

NMR: $^1$H (CDCl$_3$): 0.79 (t, 3H); 1.13 (2m, 2H); 1.95 (m, 2H); 2.20 (m, 1H); 2.45 (m, 2H); 2.77 (m, 2H); 3.87 (s, 3H); 4.88 (s, 1H); 5.09 (m, 1H); 6.78 (dd 2.4 and 8.7 Hz, 1H); 6.92 (d 2.4 Hz, 1H); 7.25 (d 8.7 Hz, 1H); 8.77 (broad s, 1H)

EXAMPLE 45

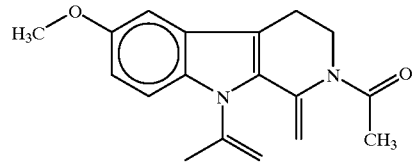

Formula: $C_{17}H_{18}N_2O_3$      M = 298.34 g.mol$^{-1}$
Structure:

1ACCARBO2: 1-(2-acetyl-6methoxy- I-methylene-2,3,4,9-tetrahydro-1H-β-carbolin-9-yl)-1-ethanone Preparation:

Sodium hydride (1.2 eq., 60% dispersion in oil) is added to a solution of 10-methoxy-harmalan (1 mmol) in DMF (10 mL), followed by acetic anhydride (1 mL). After evaporation of DMF, the crude product is chromatographed on silica gel (EtOAc/pet. ether eluent). 1-(2-Acetyl-6-methoxy-1-methylene-2,3 ,4,9-tetrahydro- 1H-β-carbolin-9-yl)-1-ethanone is thus recovered.

NMR: $^1$H (CDCl$_3$): 2.27 (s, 3H); 2.68 (s, 3H); 2.86 (t, 6 Hz, 2H); 3.85 (s, 3H); 4.09 (t, 3H); 5.28 (s, 1H); 5.35 (s, 1H); 6.85 (d 3 Hz, 1H); 6.97 (dd 3 and 9 Hz, 1H); 7.86 (d 9 Hz, 1H);

Mass spectrum: m/z: 298(M$^+$, 100), 256, 213

EXAMPLE 46

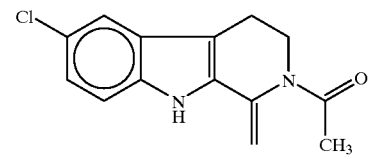

Formula: $C_{14}H_{13}N_2OCl$      M = 260.72 g.mol$^{-1}$
Structure:

CICARBO2: 1-(6-chloro-β-methylene-2,3,4,9-tetranydro-1H-β-carbolin-2-yl)-1-ethanone Preparation:

Acetic anhydride (1.1 eq.) is added to a solution of 10-chloroharnalan in pyridine. After evaporation, the crude product is chromatographed on silica gel (EtOAc/pet. ether eluent).The1-(6-chloro-1-methylene-2,3,4,9-tetrahydro-1H-β-carbolin-2-yl)-1-ethanone is thus recovered.

NMR: $^1$H (CDCl$_3$): 1.91 (s, 3H); 2.82 (t 6 Hz, 2H); 4.11 (broad s, 2H); 5.01 (broad s, 1H); 5.37 (s, 1H); 7.17 (d, 1H); 7.25 (d, 1H); 7.45 (s, 1H); 8.46 (broad s, 1H);

Mass spectrum: m/z: 262 and 260(M$^+$·1/3), 217 (100)

Exact mass: calculated 260.0716 found 260.072

EXAMPLE 47

CF3CARBO2

Formula: $C_{17}H_{15}N_2O_3F_3$    M = 352.31 g.mol$^{-1}$
Structure:

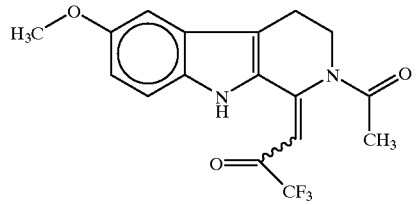

CF3CARBO2: 3-(2-acety-6-.methoxy-2 ,3,4,9-tetrahydro-1H-β-carbolin-1-ylidene)-1,1,1-trifluoroacetone Preparation:

Trifluoroacetic anhydride (0.25 mL) is added to a solution of 1-[6-methoxy-1-methylene-2,3,4,9-tetrahydro-]H-β-carbolin-2-yl)-1-ethanone (231 mg) in anhydrous dichloromethane (15 mL). After stirring (5 min., RT), the medium is neutralized by addition of aqueous ammonia solution (10 mL, 4% solution) and then diluted with dichloromethane. The organic solution obtained is washed with water and then dried over magnesium sulphate. After evaporation, the crude product is chromatographed on silica gel (EtOAc/pet. ether/MeOH). The 3-(2-acetyl-6-methoxy-2,3,4,9-tetrahydro-1H-β-carbolin- 1-ylidene)- 1,1,1-trifluoroacetone is thus recovered (150 mg, 40%).

NMR: $^1$H (CDCl3): 2.37 (s, 3H); 2.99 (t 6 Hz, 2H); 3.82 (s, 3H); 4.28 (t 6 Hz, 2H); 6.08 (s, 1H); 6.83 (d 2.1 Hz, 1H); 7.06 (dd 2.1 and 9 Hz, 1H); 7.33 (d 9 Hz, 1H);

Mass spectrum: m/z: 352(M$^+$), 309, 255(100), 241

Exact mass: calculated 352.1052 found 352.1035

EXAMPLE 48

ETCARBO2

Formula: $C_{17}H_{20}N_2O_3$    M = 284.35 g.mol$^{-1}$
Structure:

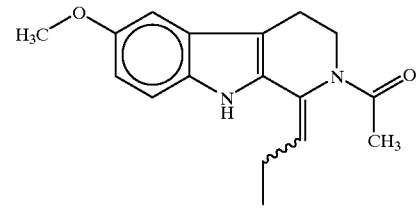

ETCARBO2: 1-(6-methoxy-1-(propylidene)-2,3,4,9-tetrahydro- 1H-P-carbolin-2-yl)-1-ethanone Preparation:

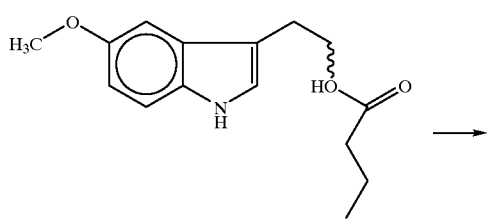

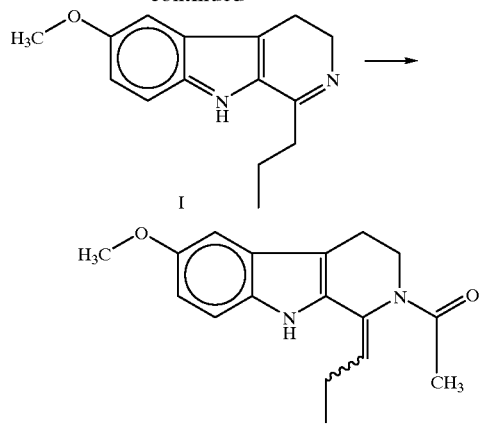

The carboline I is obtained by a Bischler-Napieralski reaction starting with N-butyryl-5-methoxytryptamine. Sodium acetate (360 mg) is added to a solution of the carboline I (360 mg) in acetic anhydride and the mixture is maintained at 50° C. overnight. The acetic anhydride is distilled off and the crude product is then chromatographed on silica gel (dichloromethane/MeOH eluent). A mixture of Z- and E-1-(6-methoxy-1-(propylidene)-2,3,4,9-tetrahydro-1 H-β-carbolin-2-yl)-1 -ethanone is thus recovered.

NMR: $^1$H (CDCl$_3$): 1.21 (t 6 Hz, 3H); 2.11 (2s, 3H); 2.52 (q 6 Hz, 2H); 2.81 (t 6 Hz, 2H); 3.81 (s, 3H); 4.09 (t 6 Hz, 2H); 5.38 (t, 0.75H); 5.60 (mi, 0.25H); 6.82 (m, 2H); 7.16 and 7.26 (2d 2.1 and 9 Hz, 1H); 8.56 and 8.8 (broad s, 1H);

Mass spectrum: m/z: 284(M$^{+\cdot}$ 100), 269, 255, 241, 227

EXAMPLE 49

6ACCARBO2

Formula: $C_{17}H_{18}N_2O_3$    M = 298.34 g.mol$^{-1}$
Structure:

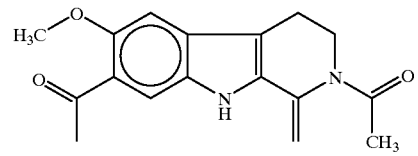

6ACCARBO2: 1-(2-acetyl-6methoxy-1-methylene-2,3,4,9-tetrahydro- 1H-β-carbolin-7-yl)-1-ethanone Preparation:

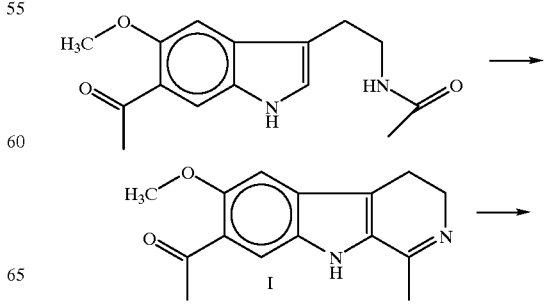

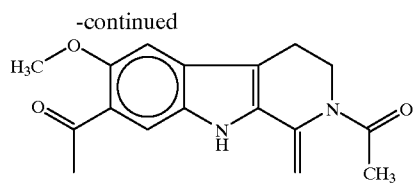

The carboline 1 is obtained by a Bischler-Napieralski reaction starting with 6-acetyl-melatonin. Acetic anhydride is added to a solution of the carboline 1 in pyridine. After removal of the acetic anhydride, the crude product is then chromatographed on silica gel (EtOAc/pet. ether eluent). 1-(2-Acetyl-6-methoxy-1-methylene-2,3,4,9-tetrahydro-1H-β-carbolin-7-yl)-1-ethanone is thus recovered.

NMR: $^1$H (CDCl$_3$): 2.3 (s, 3H); 2.71 (s, 3H); 2.84 (t, 2H); 3.95 (s, 3H); 4.12 (broad s, 2H); 5.1 (broad s, 1H); 5.37 (s, 1H); 6.19 (s, H); 7.99 (s, 1H); 9.68 (broad s, 1H);

Mass spectrum: m/z: 298(M$^+$), 283, 255(100)
Exact mass: calculated 298.1317 found 298.1303

EXAMPLE 50

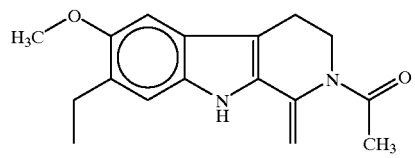

Formula: C$_{17}$H$_{20}$N$_2$O$_2$    M = 284.35 g.mol$^{-1}$
Structure:

6ETCARBO2: 1-(7-ethyl-6-methoxy-1-methiylene-2,3,4,9-tetrahydro-1H-β-carbolin-2-yl)1-ethanone
Preparation:

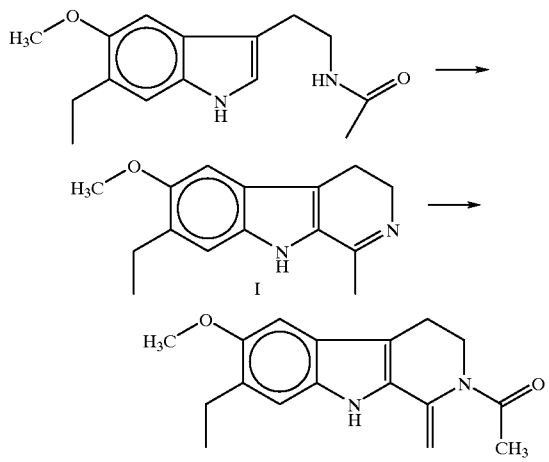

The carboline I is obtained by a Bischler-Napieralski reaction starting with 6-ethyl-melatonin. Acetic anhydride is added to a solution of the carboline obtained in pyridine. After removal of the acetic anhydride, the crude product is then chromatographed on silica gel (EtOAc/pet. ether eluent). 1-(7-Ethyl-6-methoxy- -methylene-2,3,4,9-tetrahydro-1H-β-carbolin-2-yl)-1-ethanone is thus recovered.

NMR: $^1$H (CDCl$_3$): 1.22 (t 6 Hz, 3H); 2.29 (2s, 3H); 2.72 (q 6 Hz, 2H); 2.84 (t 6 Hz, 2H); 3.87 (s, 3H); 4.2 (broad s, 2H1); 4.92 (broad s, 1H); 5.28 (s, 1H); 6.85 (s, 1H); 7.10 (s, 1H); 8.16 (broad s, 1H);

Mass spectrum: m/z: 284(M$^{30}$ ·), 241(100), 227
Exact mass: calculated 284.1524 found 284.1526

EXAMPLE 51

6CLCARBO2

Formula: C$_{15}$H$_{15}$N$_2$O$_2$    M = 290.74 g.mol$^{-1}$
Structure:

6ACCARBO2: 1-(7-chloro-β-6methoxy-1-methylene-2,3,4,9-tetrahydro-1H-β-carbolin-2-yl)-1-ethanone Preparation:

The intermediate carboline I is obtained by a Bischler-Napieralski reaction starting with 6-chloromelatonin. Acetic anhydride is added to a solution of the carboline I in pyridine. After removal of the acetic anhydride, the crude product is then chromatographed on silica gel (EtOAc/pet. ether eluent). 1-(7-Chloro-6-methoxy-1-methylene-2,3,4,9-tetrahydro- 1H-β-carbolin-2-yl)-1 -ethanone is thus recovered.

NMR: $^1$H (DMSO-d6): 2.16 (s, 3H), 2.70 (t, 2H); 3.80 (s, 3H); 3.95 (broad s, 2H); 5.0 (broad s, 1H); 5.57 (s, 1H); 6.89 (s, H); 7.83 (s, 1H); 8.5 (broad s, 1H);

EXAMPLE 52

1ACDHCARBO2

Formula: C$_{17}$H$_{20}$N$_2$O$_3$    M = 300.35 g.mol$^{-1}$
Structure:

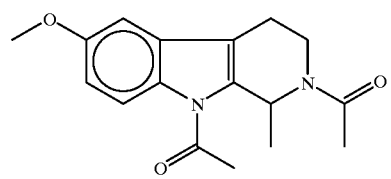

1ACDHCARBO2: 1-(2-acetyl-6methoxy-1-methyl-2,3,4,9-tetrahydro- 1H-βcarbolin-9-yl)-1-ethanone Preparation:

N,N-Diethylaminopyridine (530 mg) and pyridine (1.1 mL) are added to a solution of 1-(6-methoxy-1-methyl-2,3,4,9-tetrahydro-1H-β-carbolin-2-yl)-1-ethanone (933 mg) in toluene (100 mL) and acetic anhydride (6 mL). The mixture is refluxed for 48 h. After evaporation of the toluene, the crude product is taken up in water and then extracted with dichloromethane and, after separation on silica gel (chloroform/methanol eluent), the 1-(2-acetyl-6-methoxy-1-methyl-2,3,4,9-tetrahydro-1 H-β-carbolin-9-yl) 1-ethanone is obtained (22% yield).

NMR: $^1$H (CDCl$_3$): 1.48 and 1.55 (2d, 3H1); 2.19 (s, 3H); 2.78 (s, 3H); 2.74 (m, 2H); 3.01 and 3.6 (m, 1H); 3.85 (s, 3 H); 3.90 and 4.94 (m, 1H); 5.72 a,d 6.5 (2q, 1H); 6.9.1 (m, 2H); 7.55 and 7.61 (2d, 1H);

EXAMPLE 53

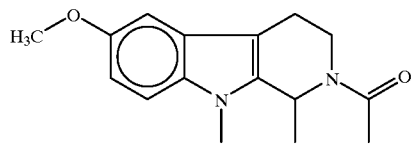

Formula: C$_{16}$H$_{20}$N$_2$O$_2$    M = 272.34 g.mol$^{-1}$
Structure:

1MIDHCARBO2: 1-(6-methoxy-1,9-dimethyl-2,3,4,9-tetrahydro-1H-β-carbolin-2-yl)-1-ethanone Preparation:

Method 1:

Potassiurn hydroxide pellets (8 g) arc added to a solution of 1-(6-mrethoxy-1-methyl-2,3,4,9-tetrahydro-1H-β-carbolin-2-yl)-1-ethanone (1.05 g) in DMSO (3 mL) and the solution is stirred for 5 min. Methyl iodide (1 mL) is then added and stirring is continued overnight. After addition of water, the product precipitates and is filcered off, taken up in dichloromethane and washed with hydrochloric acid solution (1 N) and then with water. The solvent is evaporated off, the produc; is recrystallized from ethyl acetate and 1-(6-methoxy-1,9-dimethyl-2,3,4,9-tetrahydro-1H-β-carbolin-2-yl)-1-ethanone is obtained (90%).

NMR: $^1$H (CDCl$_3$): 1.48 and 1.57 (2d, SH, CH$_3$); 2.21 (S, 3H, CH$_3$); 2.83 (m, 2H, CH$_2$); 3.55 and 3.93 (m, 2H, H-3); 3.65 (S, 3H, CH$_3$); 3.86 (S, 3H, CH$_3$); 5 and 5.84 (2q, 1H, CH); 6.87 (dd, 1H, H-7); 6.94 (d, 1H, H-5); 7.19 (d, 1H, H-8).

Mass spectrum: m/z: 272(M$^+$)(100), 257, 175

EXAMPLE 54

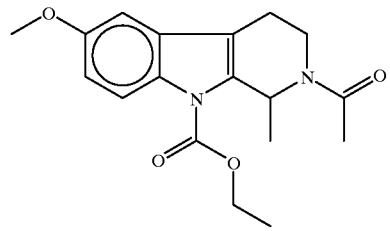

Formula: C$_{18}$H$_{22}$N$_2$O$_4$    M = 330.38 g.mol$^{-1}$
Structure:

CDHCARBO2: ethyl 2-acetyl-6-methoxy-1-methyl-2,3,4,9-tetrahydro-1H-β-carboline-9-carboxylate
Preparation:
Sodium hydroxide (3 g), tetrabutylammonium hydrogen sulphate (1.87 g) and ethyl chloroformate (2.2 mL) are successively added to a solution of 1-(6-methoxy-1-methyl-2,3,4,9-tetrahydro-1H-β-carbolin-2-yl)-1-ethanone (1.45 g) in dichloromethane (100 mL). The mixture is stirred at room temperature for 3 h. After separation on silica gel (chloroform/methanol eluent), the ethyl 2-acetyl-6-methoxy-1-methyl-2,3,4,9-tetrahydro-1H-β-carboline-9-carboxylate is obtained (70% yield).
NMR: $^1$H (CDCl$_3$): 1.55 (m, 6H); 2.29 (2s, 3H); 2.74 (m, 2H); 3.01 and 3.6 (2m, 1H); 3.85 (s, 3H); 3.94 and 4.93 (2m, 1H); 4.51 (q, 2H); 5.61 and 6.3 (2q, 1H); 6.88 (m, 2H); 7.96 and 8.04 (2d, 1H);
Mass spectrum: m/z: 330(M$^+$), 315(100), 273

EXAMPLE 55

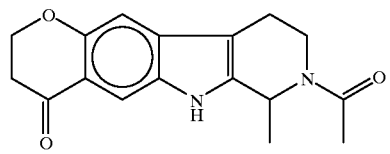

Formula: C$_{17}$H$_{18}$N$_2$O$_3$    M = 298.35 g.mol$^{-1}$
Structure:

CARBO23: 8-acetyl-7-methyl-2,3,4,6,7,8,9,10-octahydropyrano[2,3-h]-βcarbolin-4-one
Preparation:
3-Chloropropionyl chloride is added to aluminium chloride (4.34 g) in 1,2-dichloroethane (200 mL), followed by ethyl 6-methoxy-1-methyl-2,3,4,9-tetrahydro-1H-β-carboline-9-carboxylate (3 g as a solution in 1,2-dichloroethane). The mixture is stirred overnight at room temperature and then hydrolysed (100 mL of water). Afier separation of the phases by settling and evaporation of the solvent, the crude product is taken up in ethanol (20 mL) and potassium hydroxide solution (20 mL, 6N), and the resulting solution is stirred for 3 h. After evaporation of the ethanol, the crude product is extracted and then recrystallized from ethyl acetate. The 8-acetyl-7-methyl-2,3,4,6,7,8,9, 10-octahydropyrano[2,3-h]-β-carbolin-4-one is thus obtained (59% yield).
NMR: $^1$H (CDCl$_3$): 1.45 and 1.53 (2d, 3H); 2.17 (s, 3H); 2.74 (m, 4H); 3.43, 4 and 4.8 (m, 2H); 4.43 (t, 2H); 5.02 and 5.9 (2q, 1H); 6.89 (s, 1H); 7.91 (s, 1H);

EXAMPLE 56

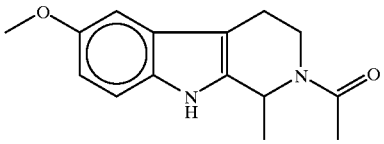

Formula: $C_{14}H_{16}N_2O_2$  M = 244.29 g.mol$^{-1}$
Structure:

DDHCABO2: 1-(6-methoxy-2,3,4,9-tetrahydro- 1H-β-carbolin-2-yl)- -ethanone

Preparation:

1-(6-Methoxy-2,3,4,9-tetrahydro- 1H-β-carbolin-2-yl)-1-ethanone is obtained quantitatively by acylation of 6-methoxy-1,2,3,4-tetrahydro-β-carboline with acetic anhydride in the presence of pyridine.

NMR: $^1$H (CDCl$_3$): 2.18 and 2.25 (2s, 3H); 2.78 and 2.89 (2t, 2H); 3.78 and 3.96 (2t, 2H); 3.86 (s, 3H); 4.64 and 4.78 (2s, 2H); 6.81 (m, 1H); 6.95 (m, 2H); 7.21 (m, 1 H);

Mass spectrum: m/z: 244(M$^{+\cdot}$)(100), 201, 185, 173

EXAMPLE 57

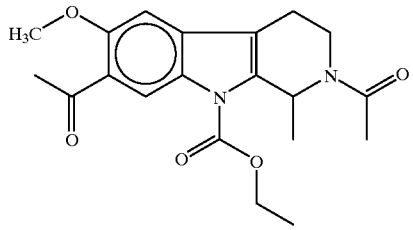

Formula: $C_{20}H_{24}N_2O_5$  M = 372.42 g.mol$^{-1}$
Structure:

C6ACDHCARBO2: ethyl 2,7-diacetyl-6-methoxy-1-netihyl-2,3,4,9-tetrahydro-1H-β-carboline-9-carboxylate Preparation:

Ethyl 2-acetyl-6-methoxy-1 -methyl-2,3,4,9-tetrahydro-1H-β-carboline-9-carboxylate (4.2 g) dissolved in 1,2-dichloroethane (150 mL) is added, at 0° C. over 15 min., to a mixture of aluminium chloride (9.2 g) and acetyl chloride (6 mL) in 1,2-dichloroethane (250 rnL). The mixture is stirred at 0° C. for 30 min. and then hydrolysed. The ethyl 2,7-diacetyl-6-methoxy-1 -methyl-2,3 ,4,9-tetrahydro-1H-β-carboline-9-carboxylate is recovered quantitatively.

NMR: $^1$H (CDCl$_3$): 1.55 (m, 6H); 2.29 (2s, 3H); 2.65 (s, 31H); 2.74 (m, 21);3 and 3.6 (2m, 1H); 3.74 (s, 3H); 3.94 and 4.93 (2m, 1H); 4.54 (q, 2H); 5.61 and 6.3 (2q, 1H); 6.85 and 6.89 (2s, 1H); 8.43 and 8.49 (2s, 1H);

EXAMPLE 58

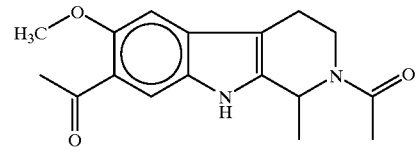

Formula: $C_{17}H_{20}N_2O_3$  M = 300.35 g.mol$^{-1}$
Structure:

6ACDHCARBO2: 1-(2-acctyl-6methoxy- l-methyl-2,3,4,9-tetrahydro-1H-β-carbolin-7-yl) 1-ethanone Preparation:

Ethyl 2,7-diacetyl-6-methoxy-1-methyl-2,3,4,9-tetrahydro-1H-β-carboline-9-carboxylate (1.3 g) dissolved in a mixture of ethanol (20 mL) and potassium hydroxide (20 mL, 6N) is stirred at room temperature for 2 h. After evaporation of the ethanol and extraction with ethyl acetate, the 1-(2-acetyl-6-methoxy-1-methyl-2,3,4,9-tetrahydro-1-β-carbolin-7-yl)-1-ethanone is recovered (82% yield).

EXAMPLE 59

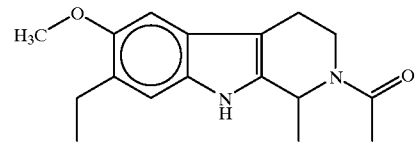

Formula: $C_{17}H_{22}N_2O_2$  M = 286.36 g.mol$^{-1}$
Structure:

6ETDHCARBO2: 1-(7-ethyl-6-mcthoxy-1-methyl-2,3,4,9-tetrahydro-1H-βcarbolin-2-yl)-1-ethanone Preparation:

Perchloric acid (2 drops) and active palladium-on-charcoal (130 mg) are added to a solution of 1 -(2-acetyl-6-methoxy-1 -methyl-2,3,4,9-tetrahydro- 1H-β-carbolin-7-yl)-1-ethanone (0.9 g) in ethyl acetate (150 mL). The mixture is stirred under a hydrogen atmosphere for 72 h. After filtration and evaporation of the solvent, the product is recrystallized from ethanol and 1-(7-ethyl-6-methoxy-1-methyl-2,3,4,9-tetrahydro-1H-β-carbolin-2-yl)-1-ethanone is obtained (80%).

NMR: $^1$H (CDCl$_3$): 1.18 (t, 3HI); 1.41 and 1.58 (2d, 3H1); 2.17 (s, 31H); 2.70 (m, 4H); 3.44 (m, 1H); 3.84 (s, 3H); 3.94 and 4.84 (2m, 1H); 5.0 and 5.63 (2q, 1H); 6.82 (s, 1H); 7.07 (s, 1H)

Mass spectrum: m/z: 286(M$^{+\cdot}$), 271(100)

EXAMPLE 60

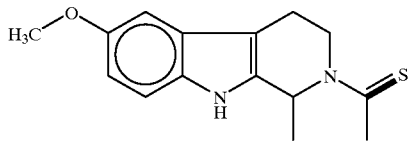

Formula: $C_{15}H_{18}N_2OS$   M = 274.38 g.mol$^{-1}$

Structure:

DHCARBO2S: 1-(6-methoxy-1-methyl-2,3,4,9-tetrahydro-1H-βcarbolin-2-yl)-1-ethane-thione Preparation:

Lawesson's reagent (520 mg) is added portionwise, at 110° C., to a solution of 1-(6-methoxy-1-methyl-2,3,4,9-tetrahydro- 1H-β-carbolin-2-yl)-1 -ethanone (500 mg) in anhydrous toluene (25 mL). After refluxing for 1 h and evaporation of the toluene, the product is chromatographed on silica gel (99/1 chlorofomvmethanol eluent) and the 1-(6-methoxy-1-methyl-2,3,4,9-tetrahydro- 1H-β-carbolin-2-yl)-1 -ethanethione is thus recovered (40% yield).

NMR: $^1$H (CDCl$_3$): 1.43 and 1.5 (2d, 3H); 2.63 (s, 3H); 2.45 (rn, 1H); 2.75 (m, 1H); 3.11 (m, 1H); 3.45 (m, 1H); 3.70 (s. 3H); 4.36 and 5.3 (2m, 1H)-5.8 and 6.6 (2q, 1H); 6.63 (m, 1H); 6.76 (d, 1H); 7.1 (d, 1H);

EXAMPLE 61

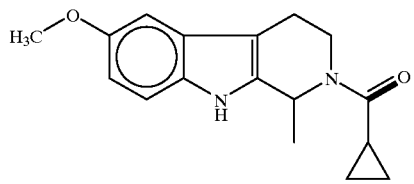

Formula: $C_{17}H_{20}N_2O_2$   M = 284.35 g.mol$^{-1}$

Structure:

DHCARBO11: cyclopropyl(6-mclhoxy-1-methyl-2,3,4,9-tetrahydro-1H-β-carbolin-2-yl)methanone Preparation:

Sodium bicarbonate (500 mg) and 10% palladium-on-charcoal are added to a solution of cyclopropyl (6-methoxy-1-methylene-2,3,4,9-tetrahydro-1H-β-carbolin-2-yl)-methanone (500 mg) in ethyl acetate (150 mL). The mixture is stirred overnight under a hydrogen atmosphere. After filtration and washing of the palladium with a chloroform/methanol solution, the product is recrystallized from ethyl acetate and the cyclopropyl(6-methoxy-1-methyl-2,3,4,9-tetrahydro- 1H-β-carbolin-2-yl)methanone is obtained (72% yield).

NMR: $^1$H (CDCl$_3$): 0.8–1.9 (m, 8H); 2.75 (m, 2H); 3.47 (t, 1H); 3.83 (s, 3H); 4.38 and 4.84 (m, 1H); 5.37 and 5.64 ($^2$q, 1H); 6.78 (dd 9 and 2 Hz, 1H); 6.90 (d 2 Hz, 1H); 7.20 (d 9 Hz, 1H);

Mass spectrum: m/z: 284(M$^+$·), 269(100)

EXAMPLE 62

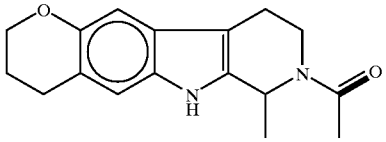

Formula: $C_{17}H_{20}N_2O_2$   M = 284.35 g.mol$^{-1}$

Structure:

PRDHCARBO2: 1-(7-methyl-2,3,4,6,7,8,9,10-octaliydropyrano[2,3-h]-β-cirbolin-8-yl)-)-ethanone.

Preparation:

Perchloric acid (1 drop) and 10% palladium-on-charcoal (30 mg) are added to a solution of 8-acetyl-7-methyl-2,3,4,6,7,8,9,1 0-octahydropyrano(2,3-1H-β-carbolin-4-one (155 mg) in ethyl acetate (60 mL). The mixture is stirred for 72 h under a hydrogen atmosphere. After filtration and washing of the palladium with a chloroform/methanol solution, the product is purified on silica gel (chloroform/methanol eluent) and the 1-(7-methyl-2,3,4,6,7,8,9,10-octahydropyrano[2,3-h]-β-carbolin-8-yl)-1 -ethanone is obtained (46% yield).

NMR: $^1$H (CDCl$_3$): 1.40 and 1.51 (2d, 3H); 2.01 (m, 219); 2.17 (s, 3H); 2.69 (m, 2H); 2.88 (t, 2H); 3.44 (m, 1H); 3.92 and 4.84 (m, 1H); 4.14 (t, 2H); 4.92 and 5.61 (2q, 1H); 6.82 (s, 1H); 6.94 (s, 1H).

Mass spectrum: m/z: 284(M$^+$·), 269, 227(100)

EXAMPLE 63

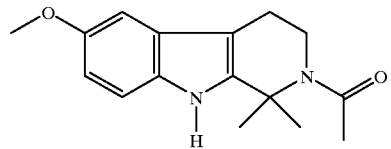

Formula: $C_{16}H_{20}N_2O_2$   M = 272.34 g.mol$^{-1}$

Structure:

MDHCARBO2: 1-(6-methoxy-1,1-dimethyl-2,3,4,9-tetrahydro-1-β-carbolin-2-yl)-1-ethanone Preparation:

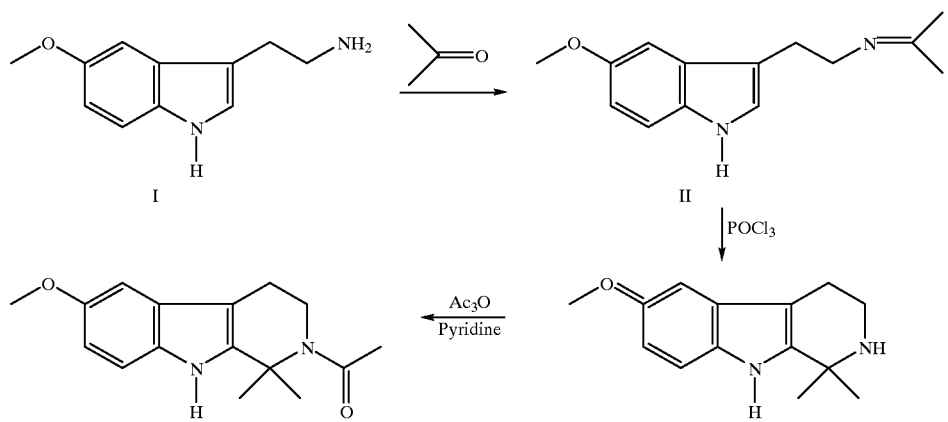

5-Methoxytryptamine 1 (1.14 g, 6 mmol) dissolved in acetone (50 mL) is stirred for one hour at room temperature. After evaporation of the acetone, the Schiff base II is obtained quantitatively. This base is heated to the reflux point of toluene for 14 hours in the presence of $POCl_3$ (2 eq.). After evaporation of the toluene, the residue is taken up in KOH solution (50 mL, 40% solution) and then extracted with ethyl acetate. The crude reaction product obtained is acylated with acetic anhydride in the presence of pyridine to give the 1-(6-methoxy-1,1-dimethyl-2,3,4,9-tetrahydro-1H-β-carbolin-2-yl)-1-ethanone (yield=40%).

NMR: $^1H$ (CDCl$_3$): 1.83 (s, 6H); 2.25 (s, 3H); 2.80 (t, 211); 3.68 (t, 2H); 3.87 (s, 3H); 6.81 (dd, 1H); 6.95 (d, 1H); 7.25 (d, 1H); 9.38 (broad s, 1H)

Mass spectrum: m/z: 272(M$^{+·}$), 257, 215(100)

EXAMPLE 64

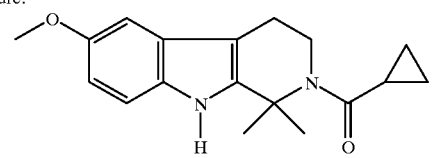

Formula: $C_{18}H_{22}N_2O_2$      M = 298.38 g.mol$^{-1}$
Structure:

MDHCARBO11: cyclopropyl(6-methoxy-1,1-dimethyl-2,3,4,9-tetrahydro-1H-βcarbolin-2-yl)methanone
Preparation:

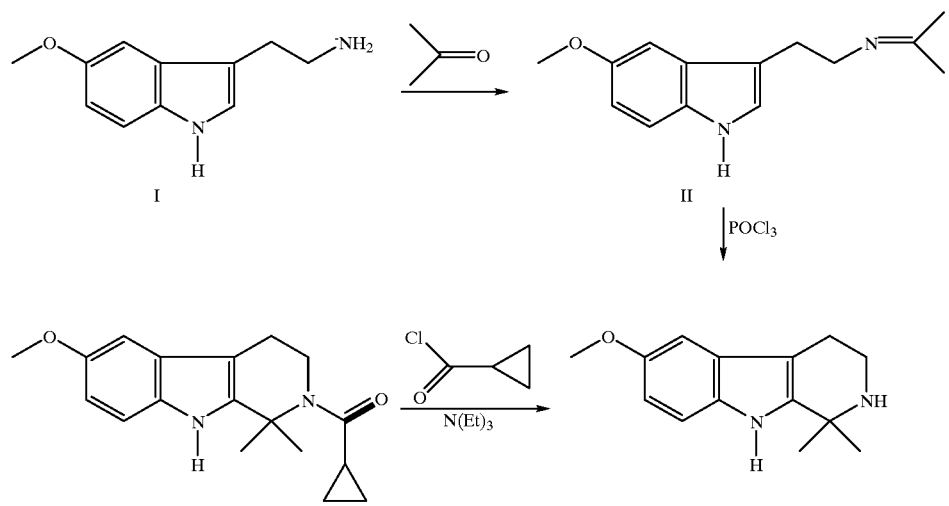

5-Methoxytryptamine I (1.14 g, 6 mmol) dissolved in acetone (50 mL) is stirred for one hour at room temperature. After evaporation of the acetone, the Schiff base II is obtained quantitatively. This base is heated to the reflux point of toluene for 14 hours in the presence of $POCl_3$ (2 eq.). After evaporation of the toluene, the residue is taken up in KOH solution (50 mL, 40% solution) and then extracted with ethyl acetate. Tie crude reaction product obtained is dissolved in arhydrous dichloromethane (50 mL) in the presence of triethylamine (1.1 eq.), after which cyclopropylcarbonyl chloride is added dropwise at 0° C. After one hour at 0° C. and then 30 min. at room temperature, water is added. After extraction with ethyl acetate, the crude product is chromatographed on silica gel (20/80 EtOAc/P.E.) and the cyclopropyl(6-methoxy-1,1-dimethyl-2,3,4,9-tetrahydro-1H-β-carbolin-2-yl)methanone is obtained (yield=20%).

NMR: $^1$H (CDCl$_3$): 0.79 (m, 2H); 1.00 (m, 2H); 1.81 (broad s, 7H); 2.83 (t, 2H); 3.86 (s, 3H); 3.93 (t, 2H); 6.83 (dd, 1H); 6.96 (d, 1H); 7.22 (d, 1H)

EXAMPLE 65

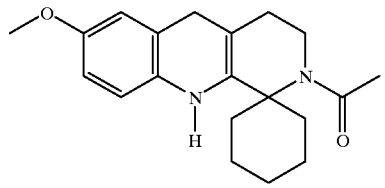

Formula: C$_{19}$H$_{24}$N$_2$O$_2$  M = 312.41 g.mol$^{-1}$

Structure:

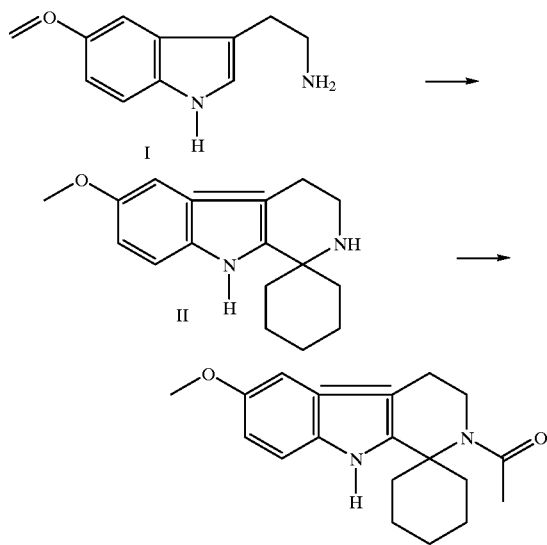

SCHCARBO2: 2'-acetyl-6'-methoxy-2', 3',4',9'-tetralydrospiro[cyclohexane-1,1'-1H-β-carboline]

Preparation:

Ethyl polyphosphate (EPP) (0.7 mL) is added to a solution of 5-methoxytryptamine I (1 g, 5.2 mmol) in cyclohexanone (10 mL, 96 eq.). The mixture is maintained between 95 and 100° C. for 11 hours. After cooling, concentrated hydrochloric acid (1.5 mL) is added. A precipitate fornms and is recovered by filtration and washed with ethyl acetate (10–15 mL). This paste is taken up in 40% potassium hydroxide solution (5 mL) and then extracted with ethyl acetate (3×150 mL). After evaporation, the carboline II is obtained. The crude reaction product obtained is acylated with acetic anhydride in the presence of pyridine to give the 2'-acetyl-6'-methoxy-2',3',4',9'-tetrahydrospiro[cyclo-hexane-1,1'H-β-carboline] (yield=70%).

NMR: $^1$H (CDCl$_3$): 1.2–1.8 (m, 10H); 2.01 (s, 3H); 2.78 (t, 2H); 3.27 (t, 2H); 3.87 (s, 3H); 6.81 (dd, 1H); 6.91 (d, 1H); 7.21 (d, 1H); 7.78 (broad s, 1H)

Mass spectrum: m/z: 312(M$^+$), 270, 241, 227(100), 214

EXAMPLE 66

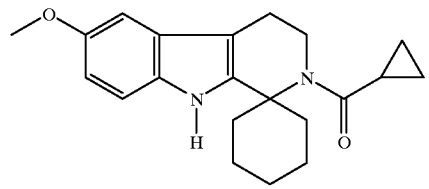

Formula: C$_{21}$H$_{26}$N$_2$O$_2$  M = 338.44 g.mol$^{-1}$

Structure:

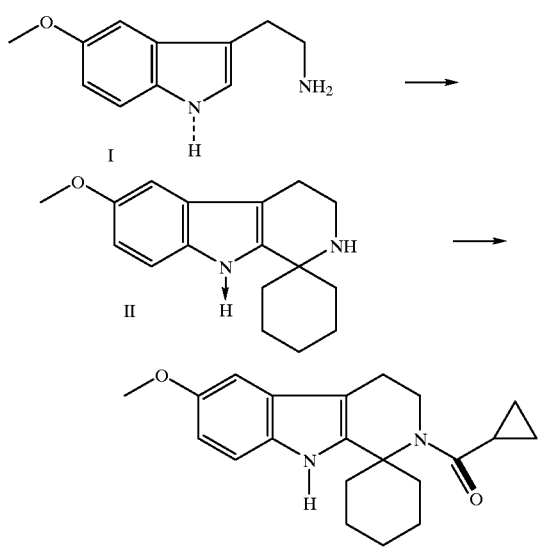

SCHCARBO11: 2'-cyclopropanecarbonyl-6'-methoxy-2', 3',4', 9'-tetrahydrospiro[cyclohexane-1,1'-1H-β-carboline]

Preparation:

Ethyl polyphosphate (EPP) (0.7 mL) is added to a solution of 5-metloxytryptamine I (1 g, 5.2 mmol) in cyclohexanone (10 mL, 96 eq.). The mixture is maintained between 95 and 100° C. for 11 hours. After cooling, concentrated hydrochloric acid (1.5 mL) is added. A precipitate forms and is recovered by filtration and washed with ethyl acetate (1.0–15 mL). This paste is taken up in 40% potassium hydroxide solution (5 mL) and then extracted with ethyl acetate (3×150 mL). After evaporation, the carboline II is obtained. The crude reaction product obtained is dissolved in anhydrous dichloromethane in the presence of triethylamine (1.1 eq.) and cyclopropylcarbonyl chloride is then added dropwise at 0° C. After one hour at 0° C. and then 5 hours at room temperature, water is added. After extraction with ethyl acetate, the crude product is flash-chromatographed on silica (20/80 EtOAc/P.E.) and 2'-cyclopropanecarbonyl-6'-methoxy-2',3',4',9'-tetrahydrospiro[cyclohexane-1,'-1H-β-carboline] is obtained (yield=30%).

NMR: $^1$H (CDCl$_3$): 0.8–1.8 (m, 15H); 2.83 (t, 2H); 3.84 (s, 3H); 4.03 (t, 2H); 6.77 (dd, 1H); 6.91 (d, 1H); 7.17 (dd, 1H)

EXAMPLE 67

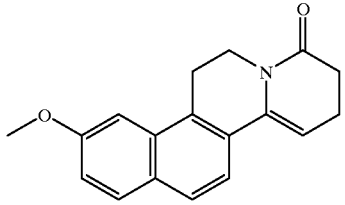

Formula: C$_{18}$H$_{17}$NO$_2$  M = 279.33 g.mol$^{-1}$
Structure:

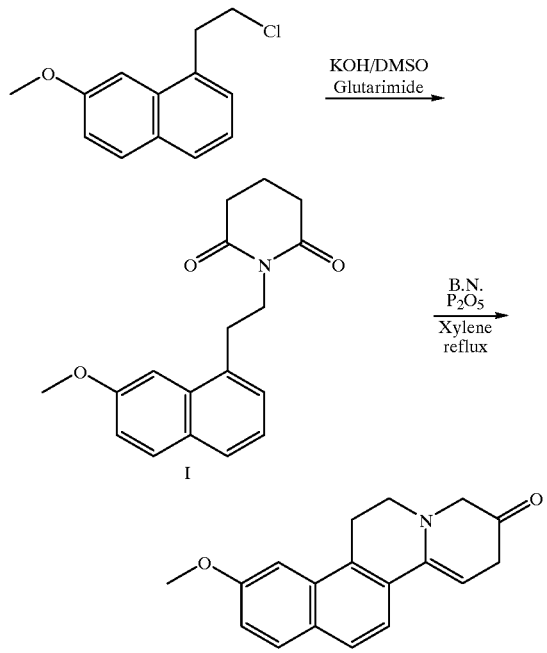

NAPH7: 3-methoxy-5,8,9,10-tetrahydro-6H-benzo[f]pyrido[2,1-a]isoquinolin-8-one

Preparation:

The glutarimide (398 mg, 3.52 mmol) is dissolved in DMSO (1 mL) with two KOH pellets. The mixture is stirred for 15 min. at room temperature. The chloro derivative dissolved in DMSO (1 mL) is then added. The mixture is heated, with stirring, at 100° C. for 28 h. After cooling, the mixture is diluted with a small amount of water and then extracted with ethyl acetate (x 4) and then with dichloromethane (x 1). The organic phase is washed with HCl solution (1 M) and then wvith water, after which it is dried over MgSO$_4$. After flash chromatography on silica (15/85 and then 50/50 EtOAc/P.E. eluent), the amide I is obtained (378 mg, yield=72%).

P$_2$O$_5$ (5.46 g, 38.4 mmol) is added to a refluxing solution of the amide 1 (450 mg, 1.5 mmol) in xylene (5 ml). After 16 h, the solution is filtered and the solid part is taken up in KOH solution (40%). The mixture is then extracted with EtOAc. After drying the organic phase over MgSO$_4$, the solvent is removed. After separation on a column of silica (98/2 CH$_2$Cl$_2$/MeOH eluent), 3-methoxy-5,8,9,10-tetrahydro-6H-benzo[f]pyrido[2,1-a]isoquinolin-8-one is obtained (20 mg).

NMR: $^1$H (CDCl$_3$): 2.50 (m, 2H); 2.61 (m, 2H); 3.17 (t, 2H); 3.95 (s, 3H); 4.03 (t, 2H); 5.97 (t, 1H); 7.16 (s, 1H); 6.85 (dd, 1H); 7.23 (d, 1H); 7.55 (d, 1H); 7.65 (d, 1H); 7.73 (d, 1H);

EXAMPLE 68

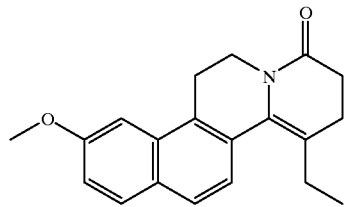

Formula: C$_{20}$H$_{21}$NO$_2$  M = 307.39 g.mol$^{-1}$
Structure:

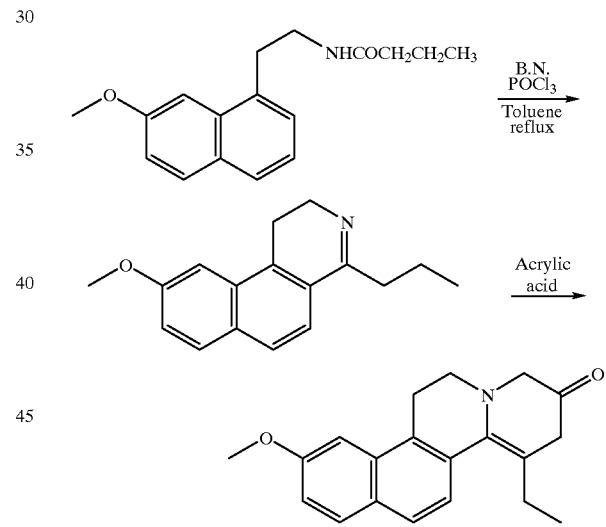

ETNAPH7: 11-ethyl-3-methoxy-5,8,9,10-tetrahydro-6H-benzo[f]pyrido[2,1-a]isoquinolin-8-one Preparation:

POCl$_3$ (4.6 mL) is added to a refluxing solution of the arnide (2.27 g, 11.1 mmol) in toluene (80 mL). After 3 h, the toluene is removed under reduced pressure. The residue is taken up in KOH solution (40%). The mixture is then extracted wvith EtOAc (x 3). After drying the organic phase over MgSO$_4$, the solvent is removed. The crude reactiorl product is dissolved in DMF (5 mL) and acrylic acid (0.94 mL, 1.2 eq.) is then added. Diphenylphosphoryl azide (2.7 mL, 1.1 ea.) dissolved in DOvF (3 mL) is then added dropwise, followed by triethylarninc (3.67 mL, 2.6 eq.). ETNAPH7 (329 mg) is obtained by recrystallization from a 20/80 EtOAc/P.E. mixture).

NMR: $^1$H (CDCl$_3$): 1.17 (t, 3H); 2.38 (m, 4H); 2.5S (t, 2H); 3.16 (t, 2H); 3.82 (t, 2H); 3.95 (s, 3H); 7.17 (dd, 1H); 7.29 (d, 1H); 7.33 (d, 1H); 7.66 (d, 1H); 7.76 (a, 1H)

EXAMPLE 69

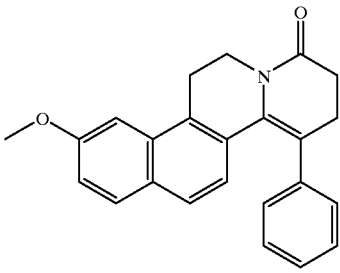

Formula: $C_{24}H_{21}NO_2$  M = 355.43 g.mol$^{-1}$
Structure:

PHNAPH7: 3-methoxy-11-phenyl-5,8,9,10-tetrahydro-6H-benzo[f]pyrido[2,1-a]isoquinolin-8-one Preparation:

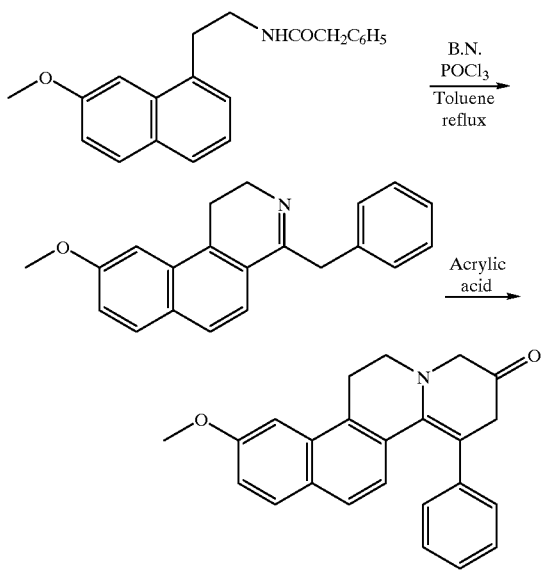

POCl$_3$ (1.4 mL) is added to a refluxing solution of the amide (600 mg) in toluene (100 mL). After 3 h, the toluene is removed under reduced pressure. The residue is taken up in KOH solution (40%). The mixture is then extracted with EtOAc (x 3). After drying the organic phase over MgSO$_4$, the solvent is removed. The crude reaction product is dissolved in DMF (4.5 mL) and acrylic acid (0.15 mL, 1.1 eq.) is then added. Diphenylphosphoryl azide (0.45 mL, 1.1 eq.) dissolved in DMF (1 mL) is then added dropwise, followed by triethylamine (0.5'mL, 2.1 eq.). The 3-methoxy-11-phenyl-5,8,9,10-tetrahydro-6H-benzo[f]pyrido[2,1-a]'isoquinolin-8-one is recovered (170 mg, yield=25%).

NMR: $^1$H (CDCl$_3$): 2.70 (m, 4H): 3.32 (t, 2H); 3.S8 (t, 2H); 3.94 (s, 31H); 6.74 to 7.60 (10H)

EXAMPLE 70

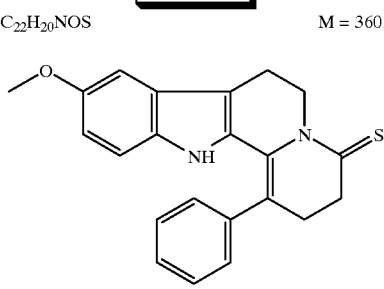

Formula: $C_{22}H_{20}NOS$  M = 360.47 g.mol$^{-1}$
Structure:

PHCARBO7S: 9-methoxy-1-phenyl-2,3,4,6,7,12-hiexahydropyrido[2,1-a][beta]-carboline-4-thione
Preparation:

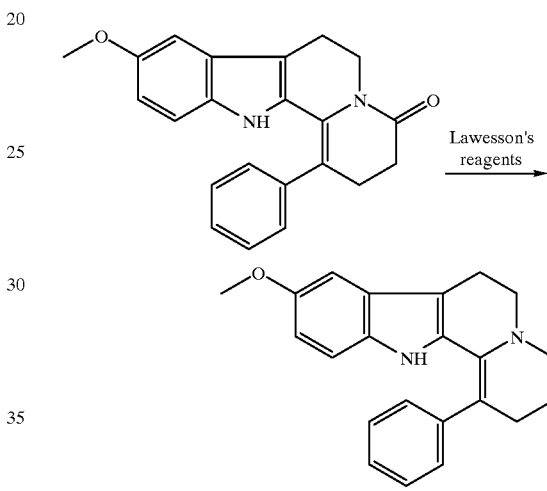

Lawesson's reagent (180 mg, 0.47 mmol) is added portionwise, at 110° C., to a solution of 9-methoxy-1-phenyl-2,3,4,6,7,12-hexahydroindolo[2,3-a]quinolizin-4-one (164 mg, 0.47 mnmol) in anhydrous toluene (10 mL). After refluxing for 30 min. and evaporation of the toluene, the product is chromatographed on silica gel (chloroform eluent) and the 9-methoxy-1-phenyl-2,3,4,6,7,12-hexahydroindolo[2,3-a]quinolizine-4-thione is thus recovered (130 mg, 76% yield).

NMR: $^1$H (CDCl$_3$): 1.32 (t, 3H); 2.32 (t, 2H), 2.65 (q, 2H); 2.98 (t, 2H); 3.08 (t, 2H); 3.89 (s, 3H); 4.80 (t, 2H); 6.91 (dd 2.4 and 8.7 Hz, 1H); 6.98 (d 2.4 Hz, 1H); 7.34 (d 8.7 Hz, 1H); 8.11 (broad s, 1H)

EXAMPLE 71

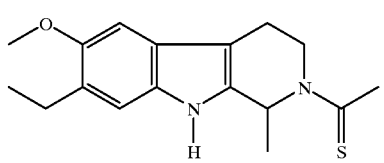

Formula: $C_{17}H_{22}N_2OS$  M = 302.43 g.mol$^{-1}$
Structure:

6ETDHCARBO2S: 1-(7-ethyl-6-methoxy-1-methyl-2,3,4,9-tetrahydro-1H-[beta]-carbolin-2-yl) 1-ethanethione Preparation:

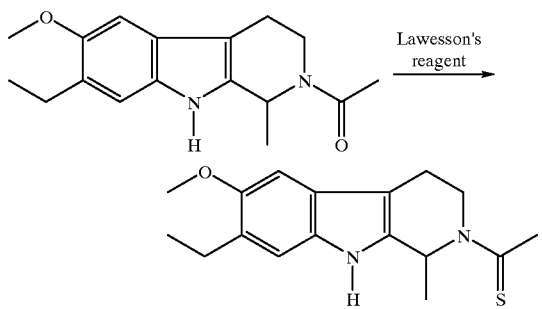

Lawesson's reagent (245 mg, 0.6 mmnol) is added portionwise, at 110° C., to a solution of 1-(7-ethyl-6-methoxy-1-methyl-2,3,4,9-tetrahydro- 1H-β-carbolin-2-yl)-1-ethanone (172 mg, 0.6 mmol) in anhydrous toluene (10 mL). After refluxing for 2 h and evaporation of the toluene, the product is chromatographed on silica gel (30/70 EtOAc/P.E. eluent) and the 1-(7-ethyl-6-methoxy-1-methyl-2,3,4,9-tetrahydro-1H-[beta]-carbolin-2-yl)-1-ethanethione is thus recovered (70 mg, 38% yield).

NMR: $^1$H (CDCl$_3$): 1.25 (t, 3H); 1.54 (d, 3H); 2.78 (m, 5H); 3.51 (m, 2H); 3.89 (s, 3H); 4.39 (d, 2H); 5.4 (q, 1H); 6.85 (s, 1H); 7.11 (s, 1H); 7.75 (broad s, 1H)

EXAMPLE 72

MESYLCARBO2: 1-methylene-2-mesyl-6-methoxy-1,2,3,4-tetrahydro-β-carboline
Preparation:

Formula: C$_{14}$H$_{16}$N$_2$O$_3$S      M = 292.35 g.mol$^{-1}$
Structure:

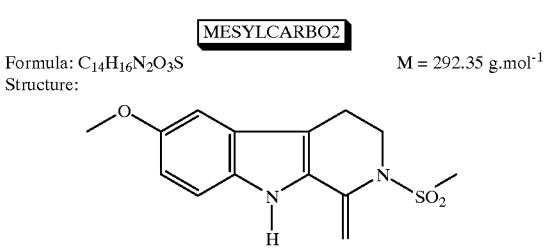

MESYLCARBO2: 1-methylene-2-mesyl-6-methoxy-1,2,3,4-tetrahydro-β-carboline
Preparation:

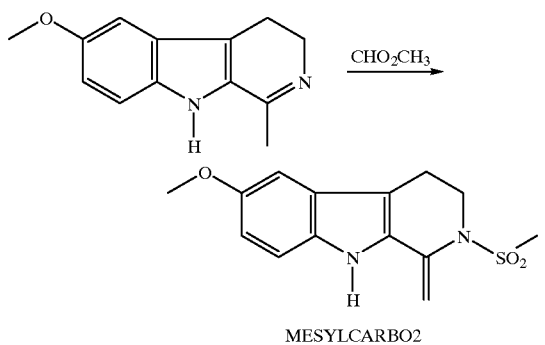

10-Methoxyharmalan (646 mg, 3 mmol) is dissolved in dry dichloromethane (40 ml). Triethylamine (1 ml, 7.2 mmol) and then, dropwise, mesyl chloride (0.25 ml, 3.2 mmol) are successively added with stirring at room temperature under a nitrogen atmosphere. The mixture is stirred for 4 hours at room temperature. Subsequently, after removal of the dichloromethane, the residue is subjected to flash chromatography on a silica column (AcOEt/PE, 50/50). 1-Methylene-2-mesyl-6-methoxy-1,2,3,4-tetrahydro-β-carboline is thus obtained (350 mg, Y=40%).

NMR: $^1$H (CDC'$_3$): 2.93 (m, 5H), 3.88 (s, 3H), 4.02 (t, 6 Hz, 2H), 5.28 (d, 2 Hz, 1H), 5.48 (d, 2 Hz, 1H), 6.93 (m, 2H), 7.27 (m, 1H)

Mass spectrum: m/z: 292 (M$^+$), 277, 213 (100), 198, 186

EXAMPLE 73

Formula: C$_{18}$H$_{18}$N$_2$OS      M = 310.41 g.mol$^{-1}$
Structure:

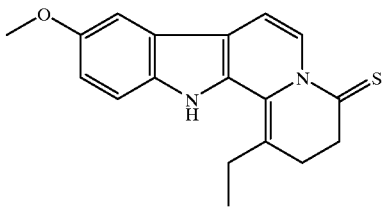

DEETCARBO7S: 9-methoxy-1-ethyl-2,3,4,12-tetrahydro-indolo[2,3-a]quinolizine-4-thione
Preparation:

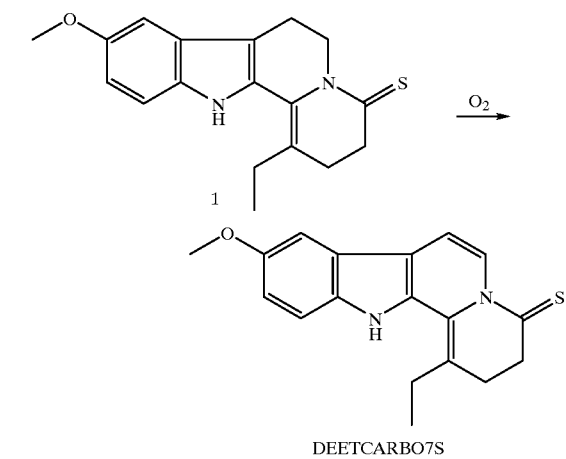

DEETCARBO7S

Potassium tert-butoxide (665 mg, 5.9 mmol) is added to a solution of 9-methoxy-1-ethyl-2,3,4,6,7,12-hexahydroindolo[2,3-a]quinolizine-4-thione (500 mg, 1.6 mmol) in DMF (42 ml). After placing the reaction assembly under vacuum, the mixture is stirred under normal oxygen pressure overnight. Water (15 ml) and concentrated hydrochloric acid (3 ml) are then successively added. The solution is stored in a refrigerator for 4 hours. After filtration, 9-methoxy-1-ethyl-2,3,4,12-tetrahydroindolo[2,3-a]quinolizine-4-thione is obtained (150 mg, Y=30%).

NMR: $^1$H (CDCl$_3$): 1.38 (t, 3H), 2.93 (q, 2H), 3.06 (t, 2H) 3.90 (s, 3H), 5.06 (t, 2H), 7.03 (d+s, 2H), 7.19 (d, 1H), 7.38 (d, 1H), 7.62 (d, 1H), 8.43 (broad s, 1H)

Mass spectrum: m/z: 310 (M$^+$), 295, 155

EXAMPLE 74

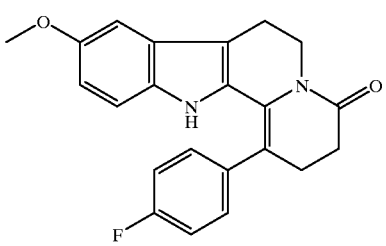

Formula: $C_{22}H_{19}N_2O_2F$    M = 362.40 g.mol$^{-1}$
Structure:

FPHCARO7: 9-methoxy-1-(p-fluorophenyl)-2,3,4,6,7,12-hexahydroindolo[2,3-a]quinolizine-4-one Preparation:

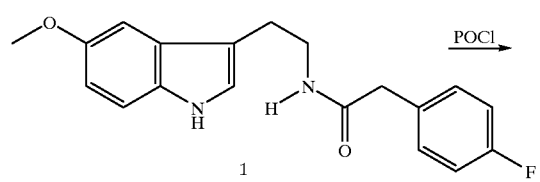

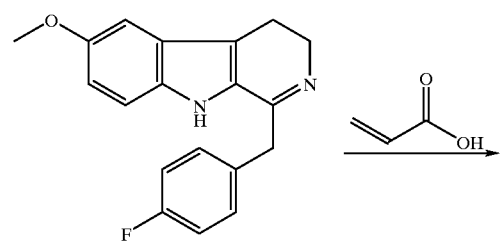

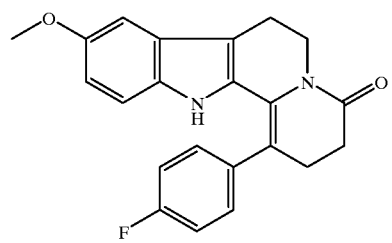

FPHCARBO7

A Bischler-Napieralski reaction, carried out on N-[2-(5-methoxy-1H-3-indolyl)ethyl]-2-(p-fluorophenyl)-acetamide 1 (1.15 g, 3.5 mmol), results in the carboline 2 (1.06 g), which is dissolved directly in anhydrous dimethylformamide (DMF) (10 ml).

This mixture is cooled to 0° C. and acrylic acid (0.24 ml, 3.5 mmol), diphenylphosphoryl azide ((PhO)$_2$P(O)N$_3$) (0.74 ml, 3.5 mmol) in solution in DMF (2 ml), dropwise, and triethylamine (1 ml, 7.8 mmol) are successively added. After separation on silica gel (chloroform), 9-methoxy-1-(p-fluorophenyl)-2,3,4,6,7,12-hexahydroindolo[2,3-a]quinolizin-4-one is recovered (750 mg, Y=58%)

NMR: $^1$H (CDCl$_3$): 2,71 (m, 4H), 2,89 (t, 2H), 3,82 (s, 3H), 4.19 (t, 2H), 6.77 (dd, 9 Hz and 3 Hz, 1H), 6.9–7.20 and 7.38 (3m, 7H)

Mass spectrum: m/z: 362 (M$^+$), 319, 253

EXAMPLE 75

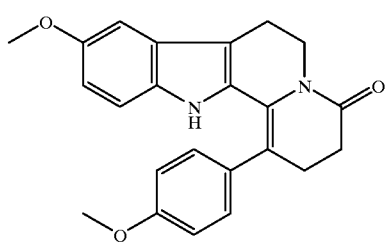

Formula: $C_{23}H_{22}N_2O_3$    M = 374.43 g.mol$^{-1}$
Structure:

ANCARBO7: 9-methoxy-1-(p-methoxryphenyl)-2,3,4,6,7,12-hexahydroindolo[2,3-a]quinolizin-4-one Preparation:

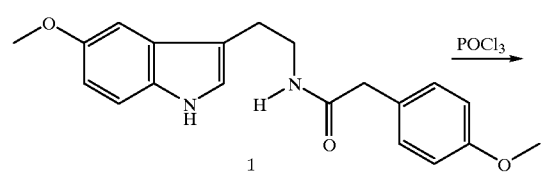

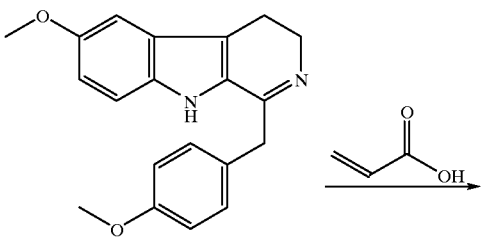

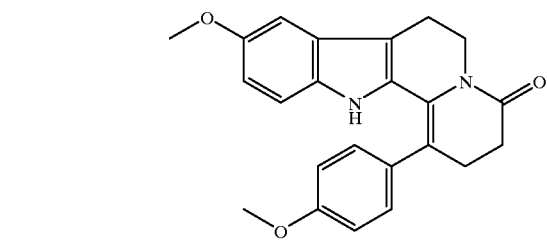

ANCARBO7

A Bischler-Napieralski reaction, carried out on N-[2-(5-methoxy-1H-3-indolyl)ethyl]-2-(p-methoxyphenyl)-acetamide 1 (800 mg, 2.1 mmol), results in the carboline 2, which is dissolved directly in anhydrous dimethylformamide (DMF) (10 ml).

This mixture is cooled to 0° C. and acrylic acid (0.15 ml, 2.2 mmol), diphenylphosphoryl azide ((PhO)$_2$P(O)N$_3$) (0.45 ml, 2 mmol) in solution in DMF (2 ml), dropwise, and triethylamine (0.53 ml, 4 mmol) are successively added. After separation on silica gel (chloroform), 9-methoxy-1-(p-methoxyphenyl)-2,3,4,6,7,12-hexahydroindolo[2,3-a]quinolizin-4-one is recovered (213 mg, Y=27%).

NMR: $^1$H (CDCl$_3$): 2.67 (m, 4H), 2.90 (t, 6 Hz, 2H), 3.83 (s, 3H), 3.91 (s, 3H), 4.20 (t, 6 Hz, 2H), 6.77, 6.88, 7.04 and 7.33 (m, 7H)

Mass spectrum: m/z: 374 (M$^+$ 100), 359, 253, 187

EXAMPLE 76

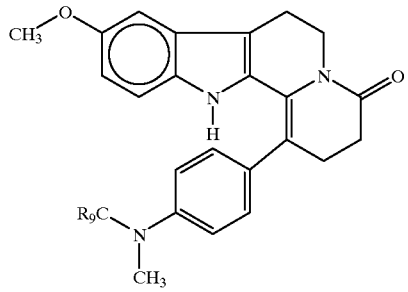

DMACARB07

Formula: $C_{24}H_{25}N_3O_2$      $M = 387.48$ g.mol$^{-1}$

Structure:

DMACARB07: 9-methoxy-1-(p-dimethylaminophenyl)-2,3,4,6,7,12-hexahydroindolo[2,3-a]quinolizin-4-one Preparation:

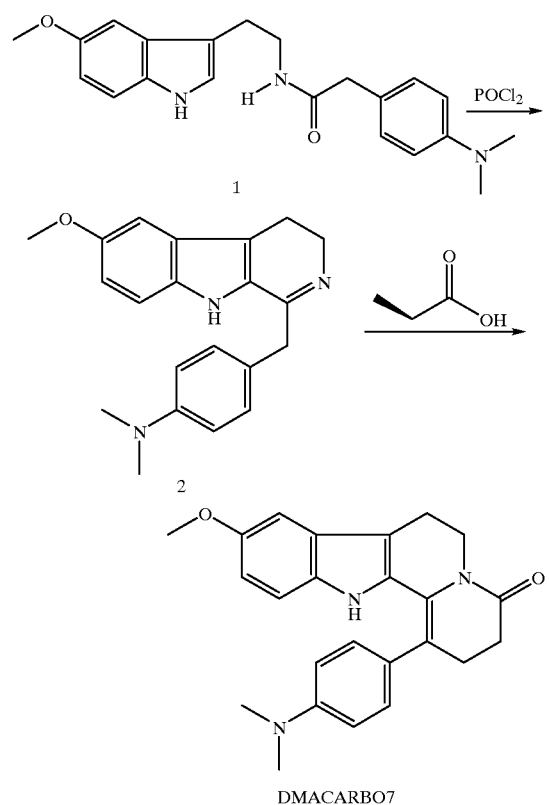

DMACARB07

A Bischler-Napieralski reaction, carried out on N-[2-(5-methoxy-1H-3-indolyl)ethyl]-2-(p-dimethylamino-phenyl)acetamide 1, results in the carboline 2, which is dissolved directly in anhydrous dimethylformamide (DMF).

This mixture is cooled to 0° C. and acrylic acid, diphenylphosphoryl azide ((PhO)$_2$P(O)N$_3$) in solution in DMF, dropwise, and triethylamine are successively added. After separation on silica gel (chloroform), 9-methoxy-1-(p-dimethylaminophenyl)-2,3,4,6,7,12-hexahydroindolo[2,3-a]quinolizin-4-one is recovered.

NMR: $^1$H (CDCl$_3$): 2.69 (m, 4H), 2.89 (t, 2H), 3.04 (s, 6H), 3.82 (s, 3H), 4.20 (t, 2H), 6.80 (m, 3H), 6.89 (m, 2H), 7.25 (d, 2H), 7.29 (broad s, 1H)

Mass spectrum: m/z: 387 (M$^{+\cdot}$), 194, 142, 134 (100)

EXAMPLE 77

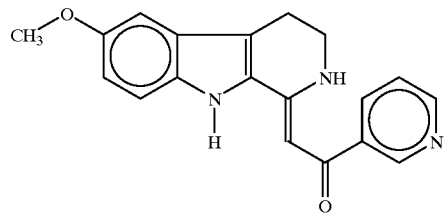

ENA3

Formula: $C_{19}H_{17}N_3O_2$      $M = 319.36$ g.mol$^{-1}$

Structure:

ENA3: 1-(3-pyridylcarbonyl)methylene-6-methoxy-1,2,3,4-tetrahydro-β-carboline

Preparation:

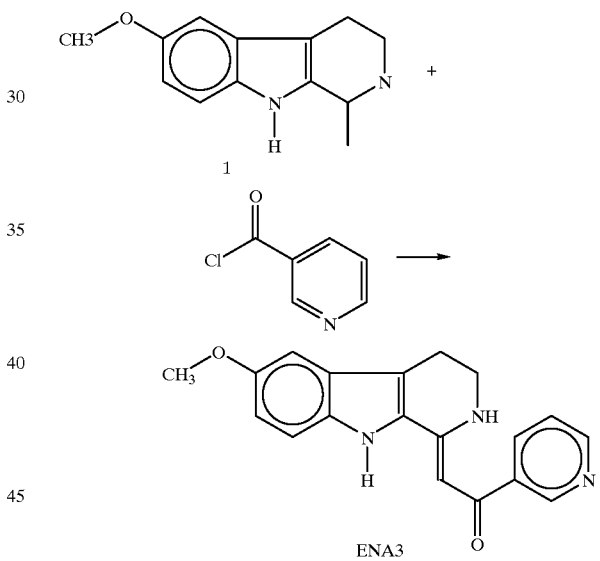

ENA3

The carboline 1 (152 mg) is dissolved in pyridine (1.5 ml). The mixture is heated to 60° C., the acid chloride (0.25 ml) is added and this mixture is maintained at this temperature for 18 h. After separation on a silica plate (chloroform/methanol, 98.5/1.5), 1-(3-pyridylcarbonyl)methylene-6-methoxy,-1;2,3,4-tetrahydro-β-carboline is recovered (20 mg).

NMR: $^1$H (CDCl$_3$): 3.00 (t, 2H), 3.85 (s, 3H), 4.28 (t, 2H) 5.02 (s, 1H), 6.89 (dd, J=3 Hz and 9 Hz, 1H), 6.94 (d, J=3 Hz, 1H), 7.17 (d, J=9 Hz, 1H), 7.33 (m, 1H), 7.90 (d, J=6 Hz, 1H), 8.64. (m, 2h), 9.2 (bs, NH)

Mass spectrum: m/z: 320 (M$^{+\cdot}$1), 319, 291 (100)

Exact mass: Calculated=319.1320 Measured=319.1331

EXAMPLE 78

PYRCARBO7

Formula: $C_{21}H_{19}N_3O_2$    M = 345.40 g.mol$^{-1}$

Structure:

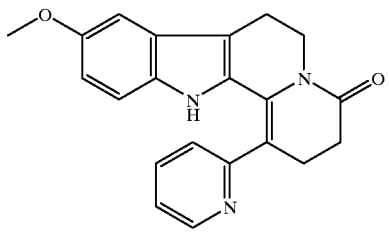

PYRCARBO7: 9-methoxy-1-(pyrid-2'-yl)-2,3,4,6,7,12-hexahydroindolo[2,3-a]quinolizin-4-one Preparation

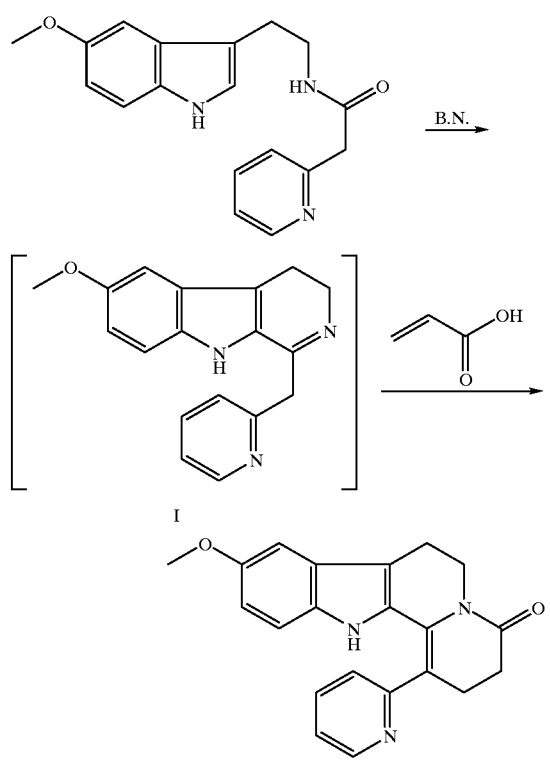

A Bischler-Napieralski reaction on the N1-(2-(5-methoxy-1H-3-indolyl)ethyl)-2-(pyrid-2'-yl)-acetamide (1.2 mg–3.9 mmol) leads to carboline I. To a solution of carboline I (760 mg–2.6 mmol) in the DNF (9 ml), acrylic acid is added (0.18 ml). Diphenylphosphorylazide (0.55 ml) is then added drip in solution in the DMF (3 ml), then the triethylamine (0.75 ml). After separation on silica gel (Chloroformn/methanol), 9-methoxy- 1-(pyrid-2'-yl)-2,3,4,6,7,12-hexahydroindolo[2,3-a]quinolizin-4-one (230 mg–17.5%) is recovered.

NMR: $^1$H (CDCl$_3$): 2.73 (m, 2H); 2.85 (m, 2H); 2.94 (t,2H); 3.18 (s, 3H); 4.24 (t, 211); 6.85 (dd, 2, 4 et 9 Hz, 1H); 6.93 (d 2, 4 Hz, 1H); 7.10 (d 9 Hz, 1H); 7.30 (dd, 1H); 7.45 (d, 1H); 7.80 (dd, 11); 8.75 (d, 1H).

Mass Spectrum: m/z: 345 (M$^+$100), 330, 316, 302

EXAMPLE 79

NPHCARBO7

Formula: $C_{22}H_{19}N_3O_4$    M = 389.41 g.mol$^{-1}$

Structure:

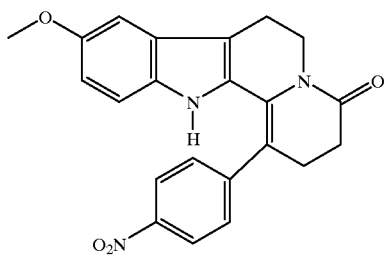

NPHCARBO7: 9-methoxy-1-β-nitrophenyl-2,3,4,6,7,12-hcxahydroindolo[2,3-a]quinolizin4one Preparation:

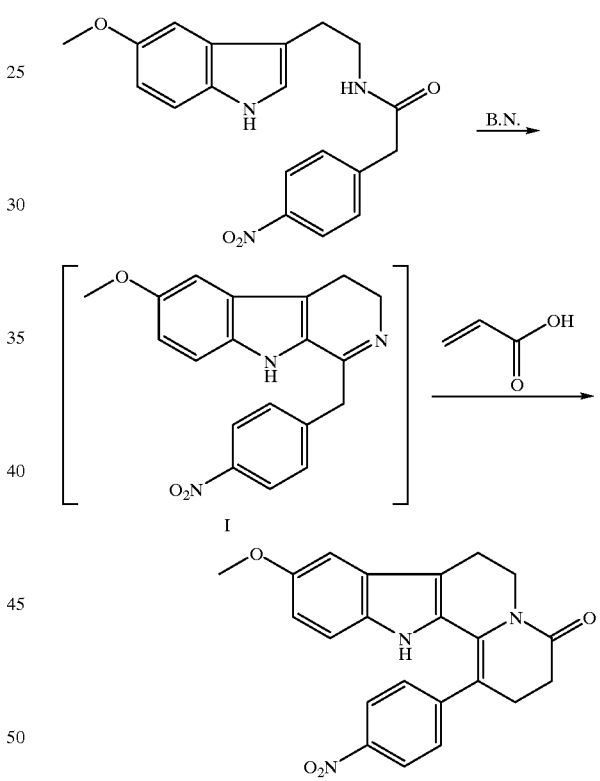

A Bischler-Napieralski reaction on the N1-(2-(5-methoxy-1H-3-indolyl)ethyl)-2-p-nitrophenyl-acetamide (360 mg–1 mmol) leads to carboline I. To a solution of carboline 1 in the DMF (10 ml), acrylic acid (0.07 ml) is added. Ddiphenylphosphorylazide (0.21 ml) is then added drip and then triethylamine (0.26 ml). After separation on silica gel (eluent AcOEt/EP—50/50), 9-methoxy-1-β-nitrophenyl -2,3,4,6,7, 12-hexahydroindolo[2,3a]quinolizin-4-one (163 mg–41%) is recovered.

NMR: $^1$H (CDCl$_3$): 2.75(m, 4H); 2.92 (t, 2H); 3.82 (s,3H), 4.17 (t, 2H); 6.80 (dd 3 and 9 Hz, 1H); 6.90 (d 3 Hz, 1H); 6.92 (d 9 Hz, 1H); 7.59 (d, 9 Hz, 1H); 8.32 (d, 9 Hz, 1H).

EXAMPLE 80

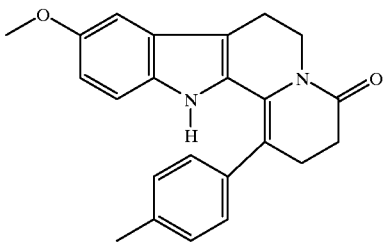

Formula: $C_{23}H_{22}N_2O_2$     $M = 358.43 \text{ g.mol}^{-1}$
Structure:

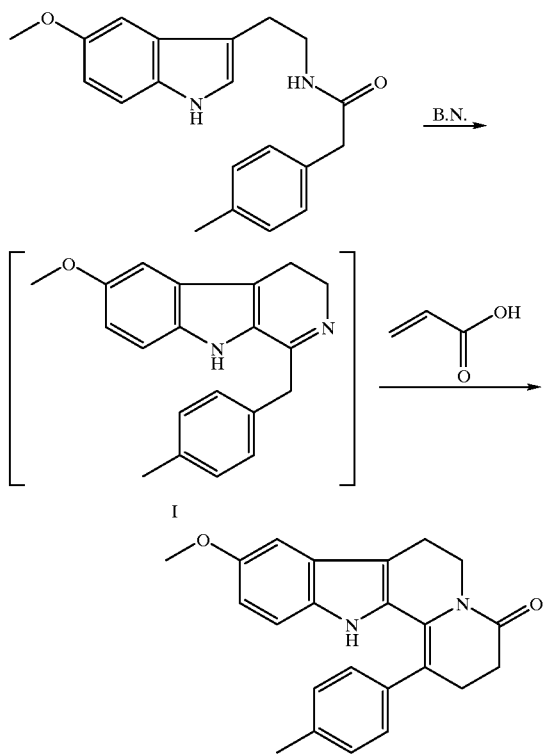

TOLCARBO7: 9-methoxy-1-β-tolyl-2,3,4,6,7,12-hexahydroindolo[2,3-a]quinolizin4one
Preparation:

A Bischler-Napieralski reaction on the N1-(2-(5-methoxy-1H-3-indolyl)ethyl)-2-p-tolyl-acetamide (2.12 mg-6.6 mmol) leads to carboline I. To a solution of carboline I in the DMF (15 ml), acrylic acid (0.46ml) is added. Diphenylphosphorylazide (1.4 ml) is then added drip and then triethylamine (1.75 ml). After separation on silica gel (eluent Chloroform/methanol), 9-methoxy-1-β-tolyl-2,3,4,6,7,12-hexahydroindolo[2,3a]quinolizin-4-one is recovered.

NMR: $^1$H (CDCl$_3$): 2.46 (s, 3H); 2.73 (m, 4H); 2.88 (t, 2H); 3.82 (s, 3H); 4.20 (t, 2H); 6.75 (dd 2 and 9 Hz, 1H); 6.84 (d 9 Hz, 1H); 6.88 (d 2 Hz, 1H); 7.03 (s broad, 1H); 7.30 (m, 4H).

BIOLOGICAL ACTIVITY

The hypnotic and sedative effects of the derivatives, according to the invention, prepared above (the test results of which are given in Table 1 below) were compared with those of three reference products, diazepam, pentobarbital sodium and melatonin, as well as with 2 psychostimulant compounds with hallucinogenic properties: 10-methoxyharmalan and harmaline, which are 3,4-dihydro-β-carbolines, in 10- to 14-day-old chicks of chair label JA657 strain. The animals are subjected to alternating programmes of lighting consisting of 12 h of darkness (20.00 h to 8.00 h) and 12 h of light (8.00 h to 20.00 h). The ambient temperature is 25° C. during the first week of rearing of the chicks and 22° C. from the second week onwards. During the day, the lighting is provided by a halogen lamp (300 W) placed 30 cm above the floor of the vivarium. During the tests, the live weights of the chicks ranged between 85 and 120 g. The tests are carried out between 14.00 and 15.00 h. The chicks are allotted, in groups of 3, in identical 30 cm×50 cm×30 cm vivariums. The test products are administered intramuscularly (1 M) into the pectoralis major muscle, as a solution in a 25/50/25 (v/vlv) ethanol/PEG400/water mixture, at the rate of 0.2 ml of solution per 100 g of live weight. The doses administered for the test products (novel compounds of the invention and reference substances) range from 0.25 lmol to 2 pmol per 100 g of live weight. The placebo corresponds to 0.2 ml of the 25/50/25 (v/v/v) ethanol/PEG400/water mixture.

The solutions of the test products in the 25/50/25 (v/v/v) ethanolVPEG400/water mixture were prepared at the time of use by successive dilution of a stock solution, obtained from 2.5 to 20 μM of accurately weighed product, to which were successively added 0.5 ml of pure ethanol and then 1 ml of PEG400, agitated by ultrasound and then made up to 2 ml with 0.5 ml of distilled water for an injectable preparation. Table 1 gives the results obtained after IM administration of doses of between 0.25 and 2 μmol of test products dissolved in 0.2 ml of the ethanol/PEG400/distilled water mixture (25/50/25 v/v/v), per 100 g of live weight. For each chick, the volume injected is adjusted, as a function of the actual 'live weight, to 0.2 ml per 100 g of live weight.

The parameters observed are the locomotor activity and the state of consciousness of the chicks for 2 h i.e. the equivalent of 6 theoretical awake/asleep cycles for a chick of this age. They are recorded by video camera for 90 minutes, the first 30 minutes being the time for adaptation to the device.

Five stages of consciousness were defined:
  stage 1: active consciousness;
  stage 2: animal laying down, head held alert with tonicity, eyes open;
  stage 3: slightly sleepy, animal drowsy: eyes closed with intermittent opening, immobile posture not modified by stimulation;
  stage 4: deep sleep laying down: relaxation of the neck, characteristic posture, head under the wing or hanging backwards;
  stage 5: sleeping standing up: eyes closed, immobile, head hanging down (catatonic).

These five stages correspond approximately to the stages of consciousness and sleep defined in the examination of the electroencephalographic plots in this species. The correspondence is as follows:
  deep sleep laying down: stage 4="slow wave sleep" (SWS)
  sleeping standing up="sleep-like state I" (SLSI).
The drowsy stage 3 might correspond to phases of paradoxal sleep, with agitation of the head, for example.

The chicks are observed by a trained observer with continuous video monitoring for at least 1 hour after the animals have woken up.

Two stimuli were used to confirm the observations of the behaviour of the chicks at regular intervals:

the noise made by tapping a plastic object on the glass of the vivarium, comparable to that of the beak of a chick on the glass, corresponds to a moderate stimulus. It is carried out at each period of observation (i.e. every 5 minutes);

provision of a metal feed tray filled with the usual feed, left in the vivarium for 2 minutes. This is a powerful stimulus which calls on vision, hearing and smell. It is carried out every 15 minutes, i.e. 6 times, at least, in each test.

Wakefulness is defined by the appearance of the elaborate conscious behaviour of searching for and consuming food or drink.

The sleep time (ST) is defined by the sum of the durations of the phases of light sleep (stage 3), deep sleep (stage 4) and sleeping standing up (stage 5). The sedation time, after waking up, corresponds to stage 2.

The falling-asleep time (FAT) is equal (to the nearest minute) to the time required to. pass from the state of active consciousness (stage 1) to a non-conscious state (stages 3, 4 and 5).

The hypnotic and sedative effects of the test products on the diurnal activity of 10- to 14-day-old chicks subjected to a programme of permanent lighting from birth for 48 h, and then to an alternate lighting programme of 12 h of daylight (8.00 h–20.00 h) and 12 h of darkness (20.00 h–8.00 h) up to the test date, are given in Table 1 below. The tests are carried out during the day between 14.00 h and 15.00 h.

For each test product, several series of measurements were taken on batches of 3 animals, each value indicated being the average in each batch of 3 chicks. When the number of batches is greater than or equal to 2, the figures indicated are the average limit values observed.

TABLE VII

| COMPOUND | DOSE (µM/100 g) | DOSE (mg/kg) | FAT (min.) | ST (min.) | Sedation time (min.) |
|---|---|---|---|---|---|
| Placebo | (20 batches) | | NA | 0 | 10–65 |
| Melatonin | 0.5 | 1.16 | NA | 0 | Not determined |
| | 1 | 2.32 | NA | 0 | 16–36 |
| | (5 batches) | | | | |
| | 2- | 4.64 | NA | 0 | 47–105 |
| | (5 batches) | | | | |
| Pentobarbital | 0.5 | 1.24 | NA | 0 | Not determined |
| | (3 batches) | | | | |
| | 1 | 2.48 | 13 | 36 | Not determined |
| Diazepam | 0.5 | 1.42 | 3–6 | 10–50 | Not determined |
| | (4 batches) | | | | |
| | 1 | 2.85 | 2–7 | 24–70 | 17–20 |
| | (10 batches) | | | | |
| | 2 | 5.69 | 2–5 | 81–100 | 14–15 |
| | (3 batches) | | | | |
| 10-methoxy- | 1.4 | 3 | NA | 0 | 0 |
| Harmalino harmalan | 1.4 | 3 | NA | 0 | 0 |
| 1 | 0.5 | 1.80 | NA | 0 | 35 |
| | 1 | 3.60 | 9 | 29 | 1 |
| 2 | 0.5 | 1.55 | 10 | <7 | 30 |
| | 1 | 3.10 | 7 | 7 | 43 |
| 3 | 2 | 4.85 | 5–5 | 25–60 | 32–63 |
| 4 | 0.5 | 1.28 | 4–8 | 2–48 | 12–38 |
| | (3 batches) | | | | |
| | 1 | 2.56 | 2–9 | 36–65 | 3–4 |
| | (8 batches) | | | | |
| | 2 | 5.12 | 4–11 | 40–70 | 22–25 |
| | (10 batches) | | | | |
| | 5 | 12.80 | 2–7 | 58–90 | 13–25 |
| | (4 batches) | | | | |
| 5 | 1 | 2.70 | 3–5 | 40–57 | 17–31 |
| 6 | 1 | 2.84 | 4–6 | 67–85 | 2–18 |

TABLE VII-continued

| COMPOUND | DOSE (µM/100 g) | DOSE (mg/kg) | FAT (min.) | ST (min.) | Sedation time (min.) |
|---|---|---|---|---|---|
| 7 | 2 | 5.65 | 5–8 | 37–80 | 12–47 |
| 8 | 2 | 6.37 | 10–10 | 20–30 | 65–70 |
| 9 | 1 | 2.86 | NA-10 | 0–<5 | 21–26 |
| 10 | 2 | 6.67 | 5–10 | 40–56 | 21–23 |
| 11 | 2 | 5.40 | 5–6 | 51–60 | 16–22 |
| 13 | 0.5 | 1.28 | NA | 0 | 8 |
| | 1 | 2.56 | 11 | 30 | 8 |
| 14 | 1 | 2.26 | NA | 0 | 12 |
| 15 | 2 | 5.40 | 9–10 | 18–33 | 7–14 |
| 16 | 2 | 5.35 | 11–11 | 30–56 | 4–10 |
| 17 | 2 | 5.35 | NA | 0 | 50–60 |
| 18 | 2 | 5.17 | 7–11 | 30–54 | 6–15 |
| 19 | 2 | 5.77 | 7–10 | 35–51 | 8–23 |
| 20 | 1 | 3.10 | 6–7 | 26–69 | 1–25 |
| 22 | 2 | 5.37 | 4–7 | 52–72 | 2–5 |
| 24 | 1 | 2.58 | NA-5 | 0–8 | 21–23 |
| 25 | 0.25 | 0.74 | 10 | 16 | 15 |
| | 0.50 | 1.48 | 9 | 18 | 17 |
| | 1 | 2.96 | 9–11 | 28–101 | 5–20 |
| | (4 batches) | | | | |
| 27 | 0.75 | 2.32 | 12 | 23 | 1 |
| 28 | 0.25 | 0.86 | 10 | 9 | 17 |
| | 0.50 | 1.72 | 12 | 11 | 8 |
| | 1 | 3.44 | 13–15 | 13–27 | 22–32 |
| | (4 batches) | | | | |
| 29 | 0.75 | 2.44 | 12 | 10 | 10 |
| 30 | 1 | 3.24 | 8 | 102 | 5 |
| 31 | 0.5 | 1.56 | 8 | 28 | 10 |
| | 1 | 3.12 | 5 | 35 | 30 |
| 32 | 1 | 2.82 | 5 | 59 | 3 |
| 33 | 2 | 5.69 | 30 | 43 | 2 |
| 34 | 2 | 6.24 | 4 | 42 | 17 |
| 36 | 2 | 6.53 | 4 | 36 | 15 |
| 38 | 2 | 5.67 | 8 | 57 | 29 |
| 39 | 1 | 2.96 | 5 | 30 | 33 |
| 40 | 2 | 5.32 | NA | 0 | 47 |
| 41 | 2 | 5.28 | NA | 0 | 46 |
| 42 | 2 | 5.45 | 5 | 13 | 58 |
| 43 | 2 | 5.41 | 13 | 41 | 17 |
| 44 | 2 | 5.97 | 15 | 15 | 37 |
| 46 | 2 | 5.21 | 8 | 8 | 20 |
| 49 | 2 | 5.97 | 5 | 29 | 25 |
| 50 | 2 | 5.69 | 9 | 7 | 44 |
| 51 | 2 | 5.81 | 6 | 37 | 71 |
| 52 | 2 | 6.00 | 13 | 14 | 34 |
| 53 | 2 | 5.44 | 15 | 14 | 33 |
| 54 | 2 | 6.60 | 15 | 12 | 33 |
| 59 | 0.5 | 1.43 | 10 | 20 | 19 |
| | 1 | 2.86 | 10 | 48 | 1 |
| 60 | 0.5 | 1.37 | 8 | 11 | 16 |
| | 1 | 2.74 | 7 | 23 | 12 |
| 62 | 1 | 2.84 | 10 | 21 | 21 |
| 63 | 2 | 5.44 | 15 | 55 | 0 |
| 67 | 1 | 2.79 | 10 | 51 | 10 |
| 68 | 1 | 3.07 | 11 | 43 | 16 |
| 70 | 0.5 | 1.80 | 9 | 20 | 8 |
| | 1 | 3.60 | 8 | 25 | 24 |
| 71 | 1 | 3.02 | 12 | 37 | 14 |

Key:
NA: not applicable, the animals remained conscious throughout the period of observation;
FAT: falling-asleep time, equal to the time required to pass from the state of active consciousness to a non-conscious state;
ST: sleep time, equal to the duration of the period of sleep from falling asleep to waking up;
Sedation time: after waking up, period of inactivity corresponding to stage 2 defined above.

In the conditions under which the test is carried out (times of administration, in the phase during which the animals receive light, between 14.00 h and 15.00 h) melatonil has no hypnotic activity.

By successively subjecting chicks to programmes of alternate and permanent lighting. wve have demonstrated experimentally that melatonin has no direct hypnotic activity which is intrinsic to its structure. Its hypnotic activity depends on the activity of the enzyme N-acetyl-transferase (NAT) in the pineal gland of the chick at the time of administration of the melatonin. The NAT enzyme is an acetylation enzyme. In the presence of the NAT enzyme in the pineal gland of the chick, the IM administration of melatonin induces a hypnotic effect of strong intensity (sleep time of between 250 and 300 minutes for a dose equal to 1 JIM of melatonin/100 g of live weight). Melatonin is thus the precursor of acetylated metabolites with direct hypnotic activity.

In contrast with melatonin, all of the derivatives of the invention described above have direct hypnotic and sedative activities, which are independent of the time of administration, i.e. of the level of N-acetyltransferase enzyme in the CNS.

The results obtained show, for the derivatives according to the invention, a hypnotic effect which is superior to that of the reference products (pentobarbital, melatonin) and equivalent or even superior to that of diazepam.

The derivatives according to the invention are thus particularly advantageous for the treatment of diseases associated with disorders of melatonin activity.

The present invention thus relates to the derivatives of general formula I, as defined above, for their use in therapy, especially for the treatment of depression and psychiatric disorders, in particular stress, anxiety, depression, insomnia, schizophrenia, psychosis and epilepsy, and also for the treatment of sleeping disorders associated with travelling ("jet lag"), neurodegenerative diseases of the central nervous system to combat Parkinson's disease or Alzheimer's disease, for the treatment of cancers, or alternatively as a contraceptive or as an analgesic.

The melatoninergic analogues according to the invention are also useful for the treatment of benign hyperplasia of the prostate, skin cancers, skin complaints such as psoriasis, acne, mycosis and glaucoma, as well as for increasing immune resistance.

They are also useful for preventing the symptoms of menopause, pre-menstrual syndromes, the effects of ageing and cot death.

They are also useful in veterinary application for controlling birth in ruminant animals.

The present invention thus also relates to the pharmaceutical compositions adapted for administration of the derivatives of general formula I, especially via the oral, parenteral or rectal route, in the form of capsules, tablets, gelatin capsules, drinkable solutions, injectable solutions, including delayed-action forms and sustained-release dressings for transder-mal administration of the active principle, nasal sprays, or topical formulations (cream, emulsion, etc.), comprising a derivative of general formula I according to the invention and at least one pharmaceutically acceptable excipient.

The pharmaceutical compositions according to the invention are advantageously dosed to deliver the active principle in a single "dosage intake". For oral administration, the effective unit doses are between 0.1 μg and 500 mg.

For intravenous administration, the effective unit doses are between 0.1 μg and 100 mg.

The melatoninergic analogues according to the invention are also useful in cosmetics, especially for protecting the skin against ageing, and also to combat hair loss.

The present invention thus also relates to a cosmetic composition comprising a derivative of general formula I according to the invention.

The cosmetic compositions according to the invention are formulated in an appropriate manner, for their topical application, especially in the form of ointments, creams, emulsions, salves, lotions, etc.

We claim:

1. A carboline derivative of Formula (Iα):

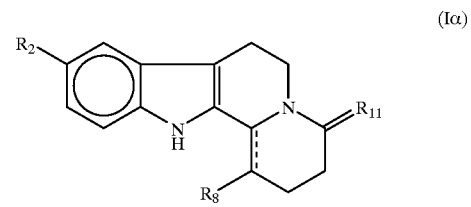

in which:

$R_2$ is a lower alkoxy radical;

$R_{11}$ is an oxygen or sulphur atom; and $R_8$ is a hydrogen atom, a hydroxyl, a lower alkyl, (lower) halogenoalkyl, a lower hydroxyalkyl, cycloalkyl, aryl, or lower aralkyl radical, or an unsaturated aliphatic chain, each optionally substituted with one or more halogens, an amino, nitro, lower alkyl, (lower) alkylamino, (lower) dialkylamino, arylamino, diarylamino, alkylcarbonyl, alkoxycarbonyl, lower alkoxy, (lower) aralkyl-carbonyl, alkoxyalkyl, formyl, (lower) alkyl-carbonyl, (lower) alkylcarbonyloxy, halo (lower) alkyl-carbonyl, halo (lower) alkyl-carbonyl, halo (lower) alkyl-carbonyloxy, (lower) alkyloxycarbonyl, carboxyl, halo, a substituted or unsubstituted carbonamide alkylsulfonyl, or an arylsulfonyl radical, or a (lower) halogenoalkylsulfonyl group.

2. The carboline derivative of claim 1, which is 9-methoxy-2,3,4,6,7,12-hexahydroindolo [2,3-a]quinolizin-4-one.

3. The carboline derivative of claim 1, which is 9-methoxy-1-ethyl-2,3,4,6,7,12-hexahydroindolo [2,3-a]quinolizin-4-one.

4. The carboline derivative of claim 1, which is 9-methoxy-1-hexyl-2,3,4,6,7,12-hexahydroindolo [2,3-a]quinolizin-4-one.

5. The carboline derivative of claim 1, which is 9-methoxy-1-isopropyl-2,3,4,6,7,12-hexahydroindolo [2,3-a]quinolizin-4-one.

6. The carboline derivative of claim 1, which is 9-methoxy-I-phenyl-2,3,4,6,7,12-hexahydroindolo [2,3-a]quinolizin-4-one.

7. The carboline derivative of claim 1, which is 1-carbethoxy-9-methoxy-2,3,4,6,7,12-hexahydroindolo [2,3-a]quinolizin-4-one.

8. The carboline derivative of claim 1, which is 9-methoxy-1,2,3,4,6,7,12,12b-octahydropyrido [2,1-a]-β-carbolin-4-one.

9. The carboline derivative of claim 1, which is 9-methoxy-1-ethyl-1,2,3,4,6,7,12,12b-octahydroindolo [2,3-a]quinolizin-4-one.

10. The carboline derivative of claim 1, which is 9-methoxy-1-phenyl-2,3,4,6,7,12-hexahydropyrido [2,1-a]-β-carbolin-4-thione.

11. The carboline derivative of claim 1, which is 9-methoxy-1-(p-fluorophenyl)-2,3,4,6,7,12-hexahydroindolo [2,3-a]quinolizin-4-one.

12. The carboline derivative of claim 1, which is 9-methoxy-1-(p-methoxyphenyl)-2,3,4,6,7,12-hexahydroindolo [2,3 -a]quinolizin-4-one.

13. The carboline derivative of claim 1, which is 9-methoxy-1-(p-dimethyaminophenyl)-2,3,4,6,7,12-hexahydroindolo [2,3-a]quinolizin-4-one.

14. The carboline derivative of claim 1, which is 9-methoxy- 1-ethyl,2,3,4,6,7,12-hexahydroindole[2,3a]quinolizin-4-thione.

15. The carboline derivative of claim 1, which is 9-methoxy-1-(pyrid-2'-yl)-2,3,4,6,7,12-hexahydroindolo[2,3a]quinolizin-4-one.

16. The carboline derivative of claim 1, which is 9-methoxy-1-ρ-nitrophenyl-2,3,4,6,7,12-hexahydroindolo[2,3-a]quinolizin-4-one.

17. The carboline derivative of claim 1, which is 9-methoxy-1-β-tolyl-2,3,4,6,7,12-hexahydroindolo [2,3-a]quinolizin-4-one.

18. A medicinal composition consisting essentially of the carboline derivative of claim 1 and a pharmaceutically acceptable carrier.

19. A method of inducing hypnotic activity in a subject, wherein said method comprises administering to the subject a hypnosis-inducing effective amount of the carboline derivative of claim 1.

20. A pharmaceutical composition comprising, as an active principal, an effective amount of at least one derivative of one of claims 1, 2, 3, 4, 5, 6, 7, 8, 9, 10, 11, 12, 13, 14, 15, 16, or 17.

21. A cosmetic composition consisting essentially of the carboline derivative of claim 1 and a cosmetically acceptable carrier.

22. A process for the preparation of a carboline derivative of Formula (Iα):

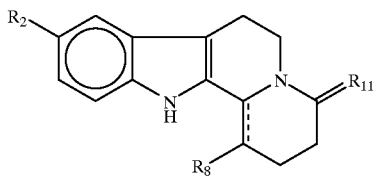

in which:
R$_2$ is a lower alkoxy radical;
R$_{11}$ is an oxygen; and
R$_8$ is as defined in claim 1;
wherein the method comprises:
1) carrying out a Bischler-Napieralski reaction with phosphorus pentoxide (P$_2$O$_5$) or phosphorus oxychloride (POCl$_3$) in a suitable solvent on a cyclic imide of the formula:

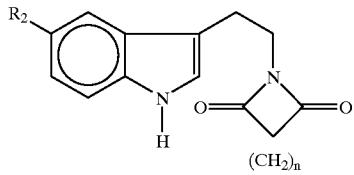

wherein R$_2$ is a lower alkoxy radical, and n is equal to 3; or 2) carrying out a reaction between a carboxylic acid and derivative of Formula (IIα):

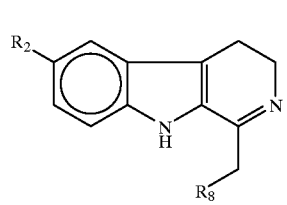

in which
R$_2$ is a lower alkoxy radical, and
R$_8$ is as defined in claim 1.

23. The process of claim 22, wherein the suitable solvent for the Bischler-Napieralski reaction is toluene or xylene.

24. The process of claim 22, wherein the carboxylic acid is acrylic acid.

25. The process of claim 22, wherein reaction 2) is performed in the presence of diphenylphosphorylazide.

26. A process for the preparation of carboline derivative of Formula (Iα):

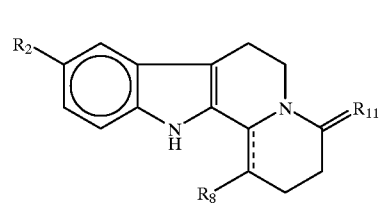

in which:
R$_2$ is a lower alkoxy radical;
R$_8$ is as defined in claim 1; and
R$_{11}$ is a sulphur atom;
wherein the method comprises reacting Lawesson's reagent with a carboline derivative of Formula (Iα):

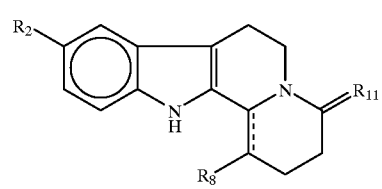

in which:
R$_2$ is a lower alkoxy radical;
R$_8$ is as defined in claim 1; and
R$_{11}$ is an oxygen atom.

* * * * *

UNITED STATES PATENT AND TRADEMARK OFFICE
CERTIFICATE OF CORRECTION

PATENT NO.: 6,048,868

DATED: April 11, 2000

INVENTOR(S): Jean-Bernard FOURTILLAN et al.

It is certified that an error appears in the above-identified patent and that said Letters Patent is hereby corrected as shown below:

In the claims:

Claim 1, col. 62, line 24, after "diarlyamino", insert – aralkylamino, arylalkylamino, (lower) haolgenoalkyloxy, arlycarbonyl,--.

Claim 6, col. 62, line 45, "I" should read "1".

Claim 11, col. 62, line 60, "p" should read --ρ--.

Claim 12, col. 62, line 63, "p" should read --ρ--.

Claim 13, col. 62, line 66, "p" should read --ρ--.

Claim 17, col. 63, line 11, "β" should read --ρ--.

Signed and Sealed this

Sixth Day of March, 2001

*Attest:*

NICHOLAS P. GODICI

*Attesting Officer*  *Acting Director of the United States Patent and Trademark Office*